(12) United States Patent
Nakajima et al.

(10) Patent No.: US 9,328,118 B2
(45) Date of Patent: May 3, 2016

(54) NITROGEN-CONTAINING BICYCLIC AROMATIC HETEROCYCLIC COMPOUND

(71) Applicant: ASTELLAS PHARMA INC., Chuo-ku (JP)

(72) Inventors: Yutaka Nakajima, Tokyo (JP); Sunao Imada, Tokyo (JP); Yuji Takasuna, Tokyo (JP); Naohiro Aoyama, Tokyo (JP); Takahiro Nigawara, Tokyo (JP); Shohei Shirakami, Tokyo (JP); Fumiyuki Shirai, Tokyo (JP); Junji Sato, Tokyo (JP); Keita Nakanishi, Tokyo (JP); Kaori Kubo, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 14/394,373

(22) PCT Filed: Apr. 17, 2013

(86) PCT No.: PCT/JP2013/061348
§ 371 (c)(1),
(2) Date: Oct. 14, 2014

(87) PCT Pub. No.: WO2013/157562
PCT Pub. Date: Oct. 24, 2013

(65) Prior Publication Data
US 2015/0126488 A1 May 7, 2015

(30) Foreign Application Priority Data

Apr. 17, 2012 (JP) .................................. 2012-094278
Mar. 14, 2013 (JP) .................................. 2013-051487

(51) Int. Cl.
*C07D 473/00* (2006.01)
*C07D 487/04* (2006.01)

(52) U.S. Cl.
CPC ............ *C07D 487/04* (2013.01); *C07D 473/00* (2013.01)

(58) Field of Classification Search
CPC ............................. C07D 487/04; C07D 473/00
See application file for complete search history.

(56) References Cited

U.S. PATENT DOCUMENTS

| | | | |
|---|---|---|---|
| 7,932,251 | B2 | 4/2011 | Cai et al. |
| 8,026,236 | B2 | 9/2011 | Robinson et al. |
| 2005/0203107 | A1 | 9/2005 | Bailey et al. |
| 2007/0179138 | A1 | 8/2007 | Cai et al. |
| 2008/0125426 | A1 | 5/2008 | Bailey et al. |
| 2010/0105652 | A1 | 4/2010 | Coteron-Lopez et al. |
| 2012/0283239 | A1 | 11/2012 | Cai et al. |

FOREIGN PATENT DOCUMENTS

| | | |
|---|---|---|
| EP | 1 757 584 | 2/2007 |
| JP | 2005-533804 | 11/2005 |
| JP | 2008-501764 | 1/2008 |
| JP | 2009-508912 | 3/2009 |
| JP | 2009-523717 | 6/2009 |
| JP | 2010-520254 | 6/2010 |
| JP | 2010-533675 | 10/2010 |
| WO | 04/000843 A1 | 12/2003 |
| WO | 2005/121106 A1 | 12/2005 |
| WO | 2007/039470 A1 | 4/2007 |
| WO | 2007/080191 A1 | 7/2007 |
| WO | 2008/107368 A1 | 9/2008 |
| WO | 2009/010491 A1 | 1/2009 |
| WO | 2010/081859 A1 | 7/2010 |
| WO | 2011/086125 A1 | 7/2011 |

OTHER PUBLICATIONS

NIH. Types of Allergic Diseases. pp. 1-4. 2015. <http://www.niaid.nih.gov/topics/allergicDiseases/Pages/allergic-diseases-types.aspx>.*
Medline Plus. Autoimmune Disorders.pp. 1-5. 2013. <http://www.nlm.nih.gov/medlineplus/ency/article/000816.htm>).*
Yasuda, Yoshiyuki. Adavanced Drug Delivery Reviews 57 (2005) 973-993.*
International Search Report issued May 21, 2013, in PCT/JP2013/061348, filed Apr. 17, 2013.
Mark Baugh, et al., "Therapeutic dosing of an orally active, selective cathepsin S inhibitor suppresses disease in models of autoimmunity", Journal of Autoimmunity, vol. 36, No. 3-4, 2011, pp. 201-209.
Jiaqiang Cai, et al., "4-(3-Trifluoromethylphenyl)-pyrimidine-2-carbonitrile as cathepsin S inhibitors: N3, not N1 is critically important", Bioorganic & Medicinal Chemistry Letters, vol. 20, No. 15, 2010, pp. 4507-4510.
Wullie Arbuckle, et al., "1*H*-Imidazo[4,5-*c*]pyridine-4-carbonitrile as cathepsin S inhibitors: Separation of desired cellular activity from undesired tissue accumulation through optimization of basic nitrogen p$k_a$", Bioorganic & Medicinal Chemistry Letters, vol. 21, No. 3, 2011, pp. 932-935.
Jiaqiang Cai, et al., "2-Phenyl-9*H*-purine-6-carbonitrile derivatives as selective cathepsin S inhibitors", Bioorganic & Medicinal Chemistry Letters, vol. 20, No. 15, 2010, pp. 4447-4450.
Jiaqiang Cai, et al., "6-Phenyl-1*H*-imidazo[4,5-*c*]pyridine-4-carbonitrile as cathepsin S inhibitors", Bioorganic & Medicinal Chemistry Letters, vol. 20, No. 15, 2010, pp. 4350-4354.
Extended European Search Report in Application No. 13777902.1 issued Sep. 25, 2015 (with corrected p. 3 of International Search Report previously considered May 21, 2015).
Office Action issued on Aug. 17, 2015 in Eurasian Patent Application No. 201491876 (with English Translation).

* cited by examiner

*Primary Examiner* — Golam M M Shameem
*Assistant Examiner* — Laura Daniel
(74) *Attorney, Agent, or Firm* — Oblon, McClelland, Maier & Neustadt, L.L.P.

(57) ABSTRACT

[Problem] On the basis of a cathepsin S inhibitory effect, an excellent agent for treating or preventing autoimmune disease, allergic disease, graft rejection of an organ, bone marrow or tissue, systemic lupus erythematosus, or the like is provided.
[Means for Solution] It was found that a nitrogen-containing bicyclic heterocyclic compound has the excellent cathepsin S inhibitory effect, thereby completing the invention. The compound of the present invention has the cathepsin S inhibitory effect, and can be used as an agent for preventing and/or treating autoimmune disease, allergic disease, graft rejection of an organ, bone marrow or tissue, systemic lupus erythematosus, or the like.

9 Claims, No Drawings

NITROGEN-CONTAINING BICYCLIC AROMATIC HETEROCYCLIC COMPOUND

CROSS REFERENCES TO RELATED APPLICATIONS

This application is a 371 Application of International Patent Application No. PCT/JP2013/061348, filed on Apr. 17, 2013, and claims priority to Japanese Patent Application No. 2012-094278, filed on Apr. 17, 2012, and Japanese Patent Application No. 2013-051487, filed on Mar. 14, 2013.

TECHNICAL FIELD

The present invention relates to a pharmaceutical composition, for example, a nitrogen-containing bicyclic aromatic heterocyclic compound useful as an active ingredient of a pharmaceutical composition for preventing and/or treating autoimmune disease, allergic disease, graft rejection of an organ, bone marrow or tissue, or systemic lupus erythematosus (SLE).

BACKGROUND ART

Cathepsin S is mainly a lysosomal cysteine protease that is expressed on antigen-presenting cells such as dendritic cells, macrophages, and B-cells, and plays a role in the degradation of an invariant chain bonded when major histocompatibility gene complex class II (MHC class II) molecules are generated. MHC class II molecules are bonded to self-peptide or non-self peptide taken from the outside of a cell, and by presenting the non-self peptide or pathogenic self-peptide to CD4 positive T cells, secretion of various cytokines is induced. It is confirmed that by inhibiting cathepsin S or making cathepsin S deficient, loading of antigenic peptide to MHC class II molecules are inhibited, and antigen presentation to CD4 positive T cells is suppressed, and by these, an immune response with respect to a foreign antigen is decreased (Nakagawa et al, Immunity, 1999, Vol. 10, No. 2, pp. 207-217).

In this respect, an inhibitor of cathepsin S can be useful as an agent for preventing and/or treating inflammation and immune disease such as rheumatoid arthritis, multiple sclerosis, SLE, psoriasis and Crohn's disease, and as an agent for preventing and/or treating graft rejection.

It have been reported that the compounds represented by the following formulas (A) (Patent Documents 1 and 2), (B) (Patent Document 3), (C) (Patent Document 4), and (D) (Patent Document 5) exhibit cathepsin S inhibition, and are useful as an agent for treating inflammations such as rheumatismimmune disorders and the like. It have been reported that the compound represented by the following formula (E) exhibits cathepsin S inhibition, and is useful as an agent for treating inflammations such as rheumatismimmune disorders and the like (Patent Document 6).

[Chem. 1]

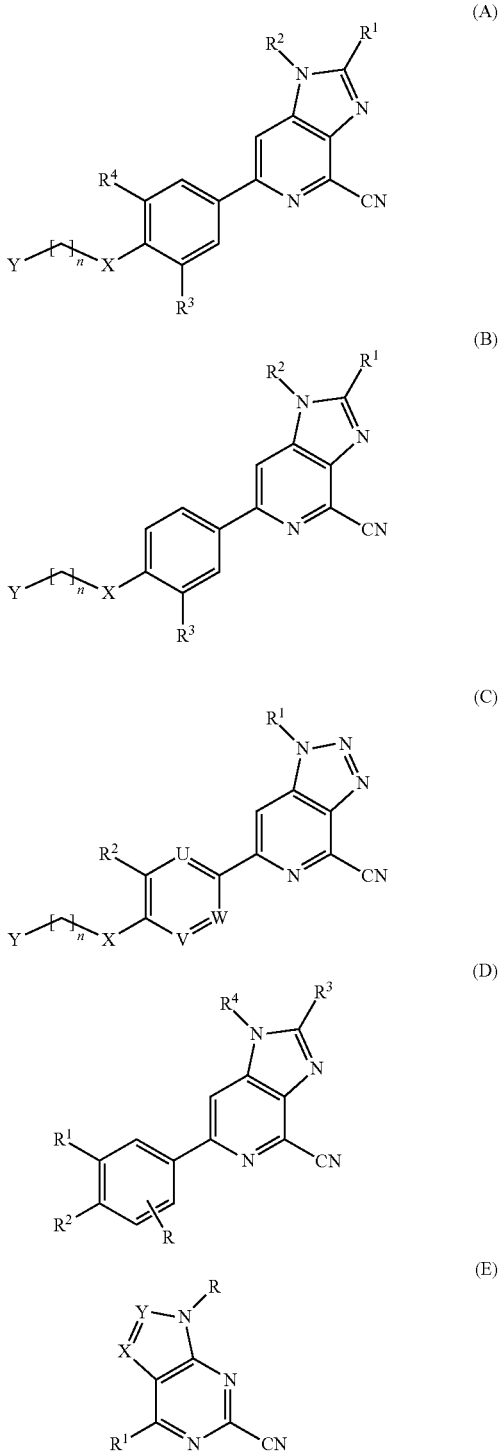

(Refer to this publication for the symbols in the formulas (A) to (D). In the formula (E), R is aryl or hetero aryl which may be substituted with a halogen or the like, H, $C_{1-6}$ alkyl, or $C_{3-6}$ cycloalkyl, Y is N, CH, or the like, $R^1$ is $Y(CH_2)_pR^7$, Y in $Y(CH_2)_pR^7$ is O or $NR^8$, and $R^7$ is a 5 to 6-membered saturated heterocycle.)

RELATED ART

Patent Document

[Patent Document 1] Pamphlet of International Publication No. 2009/010491
[Patent Document 2] Pamphlet of U.S. Patent Application Publication No. 2009/0099172
[Patent Document 3] Pamphlet of International Publication No. 2010/081859
[Patent Document 4] Pamphlet of International Publication No. 2011/086125
[Patent Document 5] Pamphlet of International Publication No. 2007/080191
[Patent Document 6] Pamphlet of International Publication No. 2004/000843

DISCLOSURE OF INVENTION

Problems to be Solved by the Invention

A pharmaceutical composition, for example, a nitrogen-containing bicyclic aromatic heterocyclic compound useful as an active ingredient of a pharmaceutical composition for preventing and/or treating autoimmune disease, allergic disease, graft rejection of an organ, bone marrow or tissue, or SLE is provided.

Means for Solving the Problems

As a result of intensive studies on a compound having the cathepsin S inhibitory effect, the present inventors found that a nitrogen-containing bicyclic aromatic heterocyclic compound has the cathepsin S inhibitory effect, thereby completing the invention.

That is, the present invention relates to the compound of the formula (I) or a salt thereof, and a pharmaceutical composition containing the compound of the formula (I) or a salt thereof, and a pharmaceutically acceptable excipient.

[1] A compound of the formula (I) or a salt thereof:

[Chem. 2]

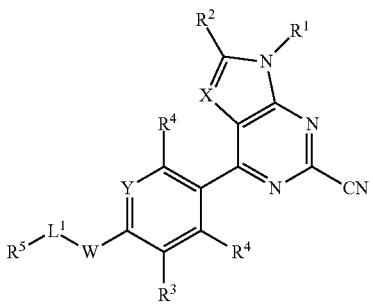

(I)

(In the formula,
X is CH or N;
Y is CH, C-halogen, or N;
W is —O— or —S(O)$_n$—;
L$^1$ is a bond, -lower alkylene-, —O-lower alkylene-, —NH-lower alkylene-, or —C(O)-lower alkylene-;
R$^1$ is i) lower alkyl which may be substituted with one or more substituents selected from the group consisting of a halogen, —OH, —O-lower alkyl, —NH$_2$, —NH-(lower alkyl), —N(lower alkyl)$_2$, —C(O)—NH$_2$, —C(O)—NH-lower alkyl, —C(O)—N(lower alkyl)$_2$, —C(O)—NH-nonaromatic heterocycle which may be substituted, —C(O)—N(lower alkyl))-nonaromatic heterocycle which may be substituted, a nonaromatic heterocycle which may be substituted, and —C(O)-nonaromatic heterocycle which may be substituted;
ii) nonaromatic heterocycle which may be substituted; or
iii) H;
R$^2$ is lower alkyl which may be substituted with a halogen, a halogen, or H;
R$^3$ is lower alkyl which may be substituted with a halogen, a halogen, or —CN;
R$^4$'s are the same as or different from each other and R$^4$ is lower alkyl which may be substituted with a halogen, a halogen, —OH, —CN, or H;
R$^5$ is lower alkyl which may be substituted with a substituent selected from the group consisting of —OH, a halogen, —NH$_2$, —NH-(lower alkyl), and —N(lower alkyl)$_2$, —O-(lower alkyl which may be substituted with a halogen), C$_{3-8}$ cycloalkyl which may be substituted, an aromatic heterocycle which may be substituted, or a nonaromatic heterocycle which may be substituted; and
n(s) is(are) the same as or different from each other, and n is an integer of 0 to 2.)

[2] The compound or a salt thereof according to [1],
wherein X is N;
R$^1$ is lower alkyl which may be substituted with one or more substituents selected from the group consisting of a halogen, —OH, —O-lower alkyl, and a nonaromatic heterocycle; in which the nonaromatic heterocycle may be substituted with lower alkyl;
R$^5$ is a nonaromatic heterocycle which may be substituted with a substituent selected from a D2 group; in which the D2 group is
(1) a halogen;
(2) cycloalkyl which may be substituted with lower alkyl;
(3) an aromatic heterocycle which may be substituted with lower alkyl;
(4) a nonaromatic heterocycle which may be substituted with lower alkyl;
(5) —OH, —CN, or —NO$_2$;
(6) —C(O)—N(R$^0$)$_2$ or —C(O)—N(lower alkyl)-nonaromatic heterocycle; and
(7) —C(O)-lower alkylene-OH;
—C(O)-(lower alkyl which may be substituted with one or more substituents selected from Z$^2$ or nonaromatic heterocycle which may be substituted with one or more substituents selected from the group consisting of a halogen, —OH, —CN, —O-lower alkyl, cycloalkyl, and a nonaromatic heterocycle); or
—C(O)-lower alkylene-(lower alkyl which may be substituted with one or more substituents selected from Z$^2$ or non-aromatic heterocycle which may be substituted with one or more substituents selected from the group consisting of a halogen, —OH, —CN, —O— lower alkyl, cycloalkyl, and a nonaromatic heterocycle); and
(8) lower alkyl or —O-lower alkyl which may be respectively substituted with one or more substituents selected from the group consisting of substituents according to the above-described (1) to (7);
R$^0$'s are the same as or different from each other, and R$^0$ is H or lower alkyl; and
Z$^2$ is the group consisting of —OH—, —O-lower alkyl, and a halogen.

[3] The compound or a salt thereof according to [2],
wherein W is —O— or —S—;
L¹ is -lower alkylene-, —O-lower alkylene-, —NH-lower alkylene-, or —C(O)-lower alkylene-;
R¹ is lower alkyl, and the lower alkyl may be substituted with tetrahydrofuranyl;
R² is H;
R³ is a halogeno-lower alkyl or —CN;
R⁴ is H; and
R⁵ is a nitrogen-containing heterocycloalkyl which may be substituted with a substituent selected from the D2 group.

[4] The compound or a salt thereof according to [3], wherein W is —O—.

[5] The compound or a salt thereof according to [4], wherein R⁵ is a group selected from the group consisting of azetidinyl, pyrrolidinyl, piperidinyl, and octahydroindolizinyl; in which
each of azetidinyl, pyrrolidinyl, piperidinyl, and octahydroindolizinyl may be substituted with a substituent selected from the D2 group.

[6] The compound or a salt thereof according to [5], which is represented by the formula (II):

[Chem. 3]

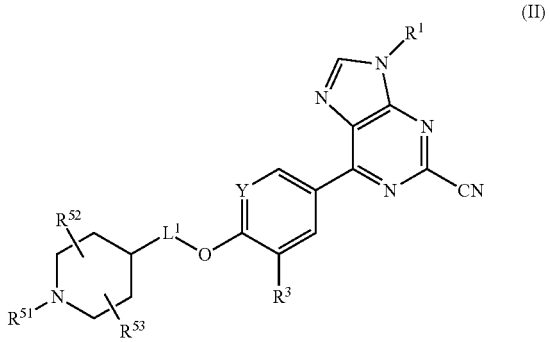

(In the formula,
R⁵¹ is H, lower alkyl, halogen-lower alkyl, cycloalkyl, -lower alkylene-OH, -lower alkylene-CN, -lower alkylene—C(O)—N(R⁰)₂, -lower alkylene-C(O)-cyclic amino, —C(O)-heterocycloalkyl, —C(O)—N(R⁰)₂, —C(O)-lower alkylene-OH, or -lower alkylene-(aromatic heterocycle which may be substituted with lower alkyl); in which
the heterocycloalkyl may be substituted with lower alkyl, —OH, or heteocycloalkyl;
the cyclic amino may be substituted with a halogen or —CN; and
R⁵² and R⁵³ are the same as or different from each other, and each of R⁵² and R⁵³ is H or lower alkyl.)

[7] The compound or a salt thereof according to [6], wherein R¹ is a methyl.

[8] The compound or a salt thereof according to [7], wherein L¹ is -lower alkylene-.

[9] The compound or a salt thereof according to [8], wherein Y is N.

[10] The compound or a salt thereof according to [9], wherein R³ is a trifluoromethyl.

[11] The compound or a salt thereof according to [10], wherein R⁵¹ is H, lower alkyl, -lower alkylene-C(O)—N(R⁰)₂, or —C(O)-(heterocycloalkyl which may be substituted with lower alkyl); and
each of R⁵² and R⁵³ is H.

[12] The compound or a salt thereof according to [11], wherein R⁵¹ is lower alkyl.

[13] The compound or a salt thereof according to [6], which is selected from the following group consisting of:
9-methyl-6-{6-[2-(piperidin-4-yl)ethoxy]-5-(trifluoromethyl)pyridin-3-yl}-9H-purine-2-carbonitrile;
6-{6-[2-(1-ethylpiperidin-4-yl)ethoxy]-5-(trifluoromethyl)pyridin-3-yl}-9-methyl-9H-purine-2-carbonitrile;
9-methyl-6-[6-{2-[1-(1-methyl-L-prolyl)piperidin-4-yl]ethoxy}-5-(trifluoromethyl)pyridin-3-yl]-9H-purine-2-carbonitrile;
6-{4-[2-(1-ethylpiperidin-4-yl)ethoxy]-3-(trifluoromethyl)phenyl}-9-(tetrahydrofuran-3-ylmethyl)-9H-purine-2-carbonitrile; and
6-{6-[2-(1-cyclobutylpiperidin-4-yl)ethoxy]-5-(trifluoromethyl)pyridin-3-yl}-9-methyl-9H-purine-2-carbonitrile.

[14] A pharmaceutical composition, containing:
the compound or a salt thereof according to [1]; and
a pharmaceutically acceptable excipient.

[15] A pharmaceutical composition for preventing or treating autoimmune disease, allergic disease, graft rejection of an organ, bone marrow or tissue, SLE, or lupus nephritis, comprising:
the compound or a salt thereof according to [1].

[16] Use of the compound or a salt thereof according to [1] for the manufacture of a pharmaceutical composition for preventing or treating autoimmune disease, allergic disease, graft rejection of an organ, bone marrow or tissue, SLE, or lupus nephritis.

[17] Use of the compound or a salt thereof according to [1] for preventing or treating autoimmune disease, allergic disease, graft rejection of an organ, bone marrow or tissue, SLE, or lupus nephritis.

[18] The compound or a salt thereof according to [1] for preventing or treating autoimmune disease, allergic disease, graft rejection of an organ, bone marrow or tissue, SLE, or lupus nephritis.

[19] A method for preventing or treating autoimmune disease, allergic disease, graft rejection of an organ, bone marrow or tissue, SLE, or lupus nephritis, comprising:
administering to a subject an effective amount of the compound or a salt thereof according to [1].

In addition, the present invention relates to a pharmaceutical composition for preventing and/or treating autoimmune disease as an aspect, allergic disease as another aspect, graft rejection of an organ, bone marrow or tissue as still another aspect, SLE as still another aspect, or lupus nephritis as further still another aspect, containing a compound of the formula (I) or a salt thereof. Moreover, the pharmaceutical composition contains an agent for preventing and/or treating autoimmune disease as an aspect, allergic disease as another aspect, graft rejection of an organ, bone marrow or tissue as still another aspect, SLE as still another aspect, or lupus nephritis as further still another aspect, containing a compound of the formula (I) or a salt thereof.

In addition, the present invention relates to use of the compound of the formula (I) or a salt thereof for the manufacture of a pharmaceutical composition for preventing and/or treating autoimmune disease, allergic disease, graft rejection of an organ, bone marrow or tissue, SLE, or lupus nephritis, the compound of the formula (I) or a salt thereof for use in preventing and/or treating autoimmune disease, allergic disease, graft rejection of an organ, bone marrow or tissue, SLE, or lupus nephritis, and a method for preventing and/or treating autoimmune disease, allergic disease, graft rejection of an organ, bone marrow or tissue, SLE, or lupus nephritis, comprising administering to a subject an effective amount of the compound of the formula (I) or a salt thereof.

Moreover, the "subject" is a human or animals in need of such prevention or treatment, and in an embodiment, the subject is a human in need of such prevention or treatment.

Moreover, unless otherwise described, in a case where the symbols in a chemical formula in the specification is also used in other chemical formulas, the same symbol indicates the same meaning.

EFFECTS OF THE INVENTION

Moreover, the compound of the formula (I) or a salt thereof has a cathepsin S inhibitory effect, and can be used as an agent for preventing and/or treating autoimmune disease as an aspect, allergic disease as another aspect, graft rejection of an organ, bone marrow or tissue as still another aspect, SLE as still another aspect, or lupus nephritis as further still another aspect.

EMBODIMENTS FOR CARRYING OUT THE INVENTION

Hereinafter, the present invention will be described in detail.

In the present specification, "lower alkyl" is a linear or branched alkyl having 1 to 6 carbon atoms (hereinafter, referred to as $C_{1-6}$), and examples thereof include methyl, ethyl, n-propyl, isopropyl, n-butyl, isobutyl, sec-butyl, tert-butyl, n-pentyl and n-hexyl. The lower alkyl is $C_{1-4}$ alkyl as another aspect, is methyl, ethyl, isopropyl, isobutyl or tert-butyl as still another aspect, is methyl or ethyl as still another aspect, is methyl as still another aspect, and is ethyl as further still another aspect.

"Lower alkylene" is a linear or branched $C_{1-6}$ alkylene, and examples thereof include methylene, ethylene, trimethylene, tetramethylene, pentamethylene, hexamethylene, propylene, methylmethylene, ethylethylene, 1,2-dimethylethylene, 2,2-dimethylethylene and 1,1,2,2-tetramethylethylene. The lower alkylene is $C_{1-4}$ alkylene as another aspect, is methylene, ethylene or trimethylene as still another aspect, is methylene or ethylene as still another aspect, is methylene as still another aspect, and is ethylene as further still another aspect.

"Halogen" is F, Cl, Br or I. The halogen is F as another aspect, and is Cl as still another aspect.

"Halogeno-lower alkyl" is lower alkyl substituted with one or more halogens. As another aspect, the halogeno-lower alkyl is lower alkyl substituted with 1 to 5 halogens, and as still another aspect, the halogeno-lower alkyl is trifluoromethyl.

"Cycloalkyl" is a $C_{3-10}$ saturated hydrocarbon cyclic group, which may have a bridge. Examples thereof include cyclopropyl, cyclobutyl, cyclopentyl, cyclohexyl, cycloheptyl, cyclooctyl and adamantyl. The cycloalkyl is $C_{3-8}$ cycloalkyl as another aspect, is $C_{3-6}$ cycloalkyl as still another aspect, is cyclopropyl as still another aspect, is cyclobutyl as still another aspect, and is adamantly as further still another aspect.

An "aromatic hererocyclic" group means a cyclic group selected from (i) 5 to 6-membered monocyclic aromatic heterocycle containing 1 to 4 hetero atoms selected from oxygen, sulfur and nitrogen, and (ii) a bicyclic or tricyclic heterocycle containing 1 to 5 hetero atoms selected from oxygen, sulfur and nitrogen, which is formed by the monocyclic aromatic heterocycle being fused with one or two rings selected from the group consisting of a monocyclic aromatic heterocycle and a benzene ring. Oxide or dioxide may be formed by the oxidation of sulfur or nitrogen which is a ring atom. Specific examples thereof include pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, furyl, indolyl, isoindolyl, benzimidazolyl, indazolyl, quinolyl, isoquinolinyl, quinazolinyl, quinoxalinyl, phthalazinyl, benzothiazolyl, benzisothiazolyl, benzothiadiazolyl, benzoxazolyl, benzisoxazolyl, benzofuranyl, benzothienyl, benzotriazolyl, carbazolyl, imidazopyridyl, imidazopyrimidinyl, imidazopyridazinyl, pyrazolopyrimidinyl and 1,8-naphthyridinyl. The aromatic hererocycle group is a 5 to 6-membered monocyclic aromatic heterocyclic group as another aspect, is pyridyl as still another aspect, and is imidazolyl as further still another aspect.

A "nonaromatic hererocyclic" group means a 3 to 15-membered monocyclic to tricyclic saturated heterocyclic group containing 1 to 4 hetero atoms selected from oxygen, sulfur and nitrogen, and as another aspect, a 4 to 10-membered monocyclic to tricyclic saturated heterocyclic group. Oxide or dioxide may be formed by the oxidation of sulfur or nitrogen which is a ring atom. A part of bond of a ring may be bridged. Specific examples thereof include azetidinyl, pyrrolidinyl, piperidinyl, piperazinyl, azepanyl, morpholinyl, thiomorpholinyl, tetrahydropyridinyl, tetrahydropyrimidinyl, oxetanyl, tetrahydrofuranyl, tetrahydropyranyl, dioxolanyl, dioxanyl, tetrahydrothiopyranyl, azabicyclo[3.2.1]octyl and octahydroindolizinyl. The nonaromatic hererocyclic group is a 4 to 10-membered monocyclic to tricyclic saturated heterocyclic group as another aspect, is a 4 to 8-membered monocyclic saturated heterocyclic group as still another aspect, is pyrrolidinyl, piperidinyl or piperazinyl as still another aspect, and is piperidinyl as further still another aspect.

A "heterocycloalkyl" group means a heterocyclic group in which bonds between ring atoms in the above-described "nonaromatic heterocyclic" group are only single bonds, and carbon atoms constituting the ring have bonding sites. Specific examples thereof include azetidin-3-yl, pyrrolidin-2-yl, pyrrolidin-3-yl, piperidin-3-yl, piperidin-4-yl, 3-azabicyclo [3.2.1]oct-8-yl, 8-azabicyclo[3.2.1]oct-3-yl, octahydroindolizin-7-yl, oxetane-3-yl, tetrahydrofuran-2-yl, tetrahydrofuran-3-yl, tetrahydropyran-3-yl, and tetrahydropyran-4-yl. As another aspect, the heterocycloalkyl group is oxetan-3-yl, tetrahydrofuran-2-yl, tetrahydrofuran-3-yl, tetrahydropyran-3-yl, or tetrahydropyran-4-yl.

A "nitrogen-containing heterocycloalkyl" group means a group having a nitrogen atom in the above-described "heterocycloalkyl", in which carbon atoms constituting the ring have bonding sites. Specific examples thereof include azetidin-3-yl, pyrrolidin-2-yl, pyrrolidin-3-yl, piperidin-3-yl, piperidin-4-yl, 3-azabicyclo[3.2.1]oct-8-yl, 8-azabicyclo[3.2.1]oct-3-yl, and octahydroindolizin-7-yl. The nitrogen-containing heterocycloalkyl group is pyrrolidin-3-yl, piperidin-3-yl, piperidin-4-yl or octahydroindolizin-7-yl as another aspect, is pyrrolidin-2-yl or pyrrolidin-3-yl as still another aspect, is piperidin-4-yl as still another aspect, and is octahydroindolizin-7-yl as further still another aspect.

A "cyclic amino" group means a group having a nitrogen atom in the above-described "nonaromatic hererocycle", in which nitrogen atoms constituting the ring have bonding sites. Specific examples thereof include azetidin-1-yl, pyrrolidin-1-yl, piperidin-1-yl, azepan-1-yl, oxazolidin-3-yl, thiazolidin-3-yl, isoxazolidin-2-yl, isothiazolidin-2-yl, piperazin-1-yl, morpholin-4-yl, thiomorpholin-4-yl, 1,1-dioxidethiomorpholin-4-yl, indolin-1-yl, isoindolin-2-yl, and 1,2,3,4-tetrahydroquinolin-1-yl. As another aspect, the cyclic amino group is azetidin-1-yl, pyrrolidin-1-yl, piperidin-1-yl, piperazin-1-yl or morpholin-4-yl, and as still another aspect, is piperidin-1-yl.

In the present specification, for example, in a case where $L^1$ is —O-lower alkylene-, O is bonded to $R^5$, and lower alkylene is bonded to W.

In the present specification, "may be substituted" means that it does not have any substituent, or has 1 to 5 substituents. Moreover, in a case of having a plurality of substituents, these substituents may be the same as or different from each other.

As acceptable substituents of "—C(O)—NH-nonaromatic heterocycle which may be substituted, —C(O)—N(lower alkyl)-nonaromatic heterocycle which may be substituted, a nonaromatic heterocycle which may be substituted, and —C(O)-nonaromatic heterocycle which may be substituted" in $R^1$ in the formula (I), or "a nonaromatic heterocycle" in "a nonaromatic heterocycle which may be substituted", groups shown as the following D1 group can be exemplified.

The D1 group is
(1) a halogen,
(2) —OH, —CN, or —NO$_2$,
(3) nonaromatic heterocycle, and
(4) lower alkyl or —O-lower alkyl which may be respectively substituted with one or more substituents selected from the group consisting of substituents according to the above-described (1) to (3).

Another aspect of the D1 group is
(1) a halogen, and
(2) lower alkyl.

As acceptable substituents of "nonaromatic heterocycle which may be substituted" described in $R^5$ in the formula (I), groups shown as the following D2 group can be exemplified.

The D2 group is
(1) a halogen,
(2) cycloalkyl which may be substituted with lower alkyl,
(3) an aromatic heterocycle which may be substituted with lower alkyl,
(4) a nonaromatic heterocycle which may be substituted with lower alkyl,
(5) —OH, —CN, or —NO$_2$,
(6) —C(O)—N($R^0$)$_2$ or —C(O)—N(lower alkyl)-nonaromatic heterocycle, and
(7) —C(O)-lower alkylene-OH,
—C(O)-(lower alkyl which may be substituted with one or more substituents selected from $Z^2$ or nonaromatic heterocycle which may be substituted with one or more substituents selected from the group consisting of a halogen, —OH, —CN, —O-lower alkyl, cycloalkyl and a nonaromatic heterocycle), or
—C(O)-lower alkylene-(lower alkyl which may be substituted with one or more substituents selected from $Z^2$ or nonaromatic heterocycle which may be substituted with one or more substituents selected from the group consisting of a halogen, —OH, —CN, —O— lower alkyl, cycloalkyl and a nonaromatic heterocycle), and
(8) lower alkyl or —O-lower alkyl which may be respectively substituted with one or more substituents selected from the group consisting of substituents according to the above-described (1) to (7).

Here, $R^0$'s are the same as or different from each other, and $R^0$ is H or lower alkyl, and $Z^2$ is a group consisting of —OH—, —O-lower alkyl, and a halogen.

Another aspect of the D2 group is
(1) a halogen,
(2) cycloalkyl which may be substituted with lower alkyl,
(3) an aromatic heterocycle which may be substituted with lower alkyl,
(4) a nonaromatic heterocycle which may be substituted with lower alkyl,
(5) —OH, —CN, or —NO$_2$,
(6) —C(O)—NH$_2$, —C(O)—N(lower alkyl)$_2$, or —C(O)—N(lower alkyl)-nonaromatic heterocycle, and
(7) —C(O)-lower alkylene-OH, —C(O)-(lower alkyl which may be substituted with one or more substituents selected from $Z^2$ or nonaromatic heterocycle which may be substituted with one or more substituents selected from the group consisting of a halogen, —OH, —CN, —O-lower alkyl, and cycloalkyl), or —C(O)-lower alkylene-(lower alkyl which may be substituted with one or more substituents selected from $Z^2$ or nonaromatic heterocycle which may be substituted with one or more substituents selected from the group consisting of a halogen, —OH, —CN, —O-lower alkyl, and cycloalkyl), and
(8) lower alkyl or —O-lower alkyl which may be respectively substituted with one or more substituents selected from the group consisting of substituents according to the above-described (1) to (7).

Another aspect of the D2 group is
(1) a halogen,
(2) cycloalkyl,
(3) an aromatic heterocycle which may be substituted with lower alkyl,
(4) nonaromatic heterocycle,
(5) oxo,
(6) —OH,
(7) —CN,
(8) —C(O)—N(lower alkyl)$_2$,
(9) —C(O)-lower alkylene-OH, and
(10) —C(O)-(nonaromatic heterocycle which may be substituted with one or more substituents selected from the group consisting of lower alkyl, a halogen, —OH and —CN), and
(11) lower alkyl which may be substituted with one or more substituents selected from the group consisting of substituents according to the above-described (1) to (10).

Another aspect of the D2 group is
(1) a halogen,
(2) cycloalkyl,
(3) an aromatic heterocycle which may be substituted with lower alkyl,
(4) nonaromatic heterocycle,
(5) —OH,
(6) —CN,
(7) —C(O)—N(lower alkyl)$_2$,
(8) —C(O)-lower alkylene-OH, and
(9) —C(O)-(nonaromatic heterocycle which may be substituted with one or more substituents selected from the group consisting of lower alkyl, a halogen, —OH and —CN), and
(10) lower alkyl which may be substituted with one or more substituents selected from the group consisting of substituents according to the above-described (1) to (9).

Another aspect of the D2 group is
(1) cycloalkyl,
(2) —OH,
(3) —C(O)—N(lower alkyl)$_2$, and
(4) —C(O)-(nonaromatic heterocycle which may be substituted with one or more substituents selected from the group consisting of lower alkyl, a halogen, —OH and —CN), and
(5) lower alkyl which may be substituted with one or more substituents selected from the group consisting of substituents according to the above-described (1) to (4).

Another aspect of the D2 group is
(1) —OH,
(2) —C(O)—N(lower alkyl)$_2$, and
(3) —C(O)-(nonaromatic heterocycle which may be substituted with one or more substituents selected from the group consisting of lower alkyl and —OH), and
(4) lower alkyl which may be substituted with one or more substituents selected from the group consisting of substituents according to the above-described (1) to (3).

Another aspect of the D2 group is
(1) lower alkyl,
(2) -lower alkylene-OH,
(3) -lower alkylene-C(O)—N(lower alkyl)$_2$, and
(4) —C(O)-(nonaromatic heterocycle which may be substituted with lower alkyl).

As acceptable substituents of "C$_{3-8}$ cycloalkyl which may be substituted" or "aromatic heterocycle which may be substituted" in R$^5$ in the formula (I), groups shown as the following D3 group can be exemplified.

The D3 group is
(1) a halogen,
(2) —OH, —CN, or —NO$_2$, and
(3) lower alkyl or —O-lower alkyl which may be respectively substituted with one or more substituents selected from the group consisting of substituents according to the above-described (1) to (2).

Another aspect of the D3 group is
(1) lower alkyl, and
(2) a halogen.

Aspect of the present invention is shown below. "A compound" in this section means "a compound or a salt thereof".

(1) A compound of the formula (I), in which X is CH. As another aspect, a compound in which X is N.

(2) A compound of the formula (I), in which Y is CH. As another aspect, a compound in which Y is N.

(3) A compound of the formula (I), in which W is —O— or —S—. As another aspect, a compound in which W is —O—.

(4) A compound of the formula (I), in which L$^1$ is -lower alkylene-, —O-lower alkylene-, or —C(O)-lower alkylene.

As another aspect, a compound in which L$^1$ is -lower alkylene- or —O-lower alkylene-.

As still another aspect, a compound in which L$^1$ is -lower alkylene-.

(5) A compound of the formula (I), in which R$^1$ is lower alkyl which may be substituted with a substituent selected from the group consisting of —OH, —O-lower alkyl, and a nonaromatic heterocycle, in which the nonaromatic heterocycle may be substituted with lower alkyl.

As another aspect, a compound in which R$^1$ is lower alkyl which may be substituted with —OH or —O-lower alkyl.

As still another aspect, a compound in which R$^1$ is lower alkyl which may be substituted with tetrahydrofuran.

As still another aspect, a compound in which R$^1$ is lower alkyl.

As further still another aspect, a compound in which R$^1$ is methyl.

(6) A compound of the formula (I), in which R$^2$ is lower alkylene which may be substituted with a halogen or H.

As another aspect, a compound in which R$^2$ is lower alkyl which may be substituted with a halogen.

As still another aspect, a compound in which R$^2$ is H.

(7) A compound of the formula (I), in which R$^3$ is halogeno-lower alkyl or —CN.

As another aspect, a compound in which R$^3$ is halogeno-lower alkyl.

As still another aspect, a compound in which R$^3$ is trifluoromethyl.

(8) A compound of the formula (I), in which R$^4$'s are the same as or different from each other, and R$^4$ is H or a halogen. As another aspect, a compound in which all R$^4$ are H's.

(9) A compound of the formula (I), in which R$^5$ is lower alkyl which may be substituted with —N(lower alkyl)$_2$, an aromatic heterocycle which may be substituted, or a nonaromatic heterocycle which may be substituted.

As another aspect, a compound in which R$^5$ is lower alkyl which may be substituted with —N(lower alkyl)$_2$, or a nonaromatic heterocycle which may be substituted.

As still another aspect, a compound in which R$^5$ is a nonaromatic heterocycle which may be substituted.

As still another aspect, a compound in which R$^5$ is nitrogen-containing heterocycloalkyl which may be substituted.

As still another aspect, a compound in which R$^5$ is azetidinyl which may be substituted, pyrrolidinyl which may be substituted, piperidinyl which may be substituted, or octahydroindolizinyl which may be substituted.

As still another aspect, a compound in which R$^5$ is piperidinyl which may be substituted.

(10) A compound of the formula (I), in which R$^5$ is

[Chem. 4]

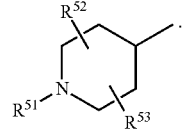

(10-1) A compound according to (10), in which R$^{51}$ is H, lower alkyl, halogeno-lower alkyl, cycloalkyl, -lower alkylene-OH, or -lower alkylene-CN.

As another aspect, a compound according to (10), in which R$^{51}$ is H, -lower alkylene-C(O)—N(R$^0$)$_2$, or —C(O)-(heterocycloalkyl which may be substituted with lower alkyl, —OH or heterocycloalkyl).

As still another aspect, a compound according to (10), in which R$^{51}$ is H, lower alkyl, -lower alkylene-C(O)—N(R$^0$)$_2$, or —C(O)-(heterocycloalkyl which may be substituted with lower alkyl).

As still another aspect, a compound according to (10), in which R$^{51}$ is lower alkyl.

As further still another aspect, a compound according to (10), in which R$^{51}$ is H.

(10-2) a compound according to (10), in which each of R$^{52}$ and R$^{53}$ is H.

(11) A compound of the formula (I), in which arbitrary two or more among aspects described in the above-described (1) to (10-2) are combined.

Still another aspect of the present invention is shown below.

A compound of the formula (1) or a salt thereof in which X is N, Y is N, W is —O—, L$^1$ is -lower alkylene-, R$^1$ is methyl, R$^2$ is H, R$^3$ is trifluoromethyl, all R$^4$ are H's, R$^5$ is

[Chem. 5]

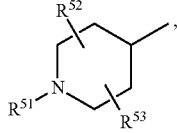

R$^{51}$ is a lower alkyl, and each of R$^{52}$ and R$^{53}$ is H.

Still another aspect of the present invention is shown below.

A compound of the formula (I) or a salt thereof in which X is CH; R$^1$ is lower alkyl which may be substituted with one or more substituents selected from the group consisting of a halogen, —OH, —O-lower alkyl, and a nonaromatic heterocycle; in which the nonaromatic heterocycle may be substituted with lower alkyl; and $R^5$ is a nonaromatic heterocycle which may be substituted with a substituent selected from the D2 group.

Examples of a specific compound contained in the compound of the formula (I) or a salt thereof include the following compounds.

9-methyl-6-{6-[2-(piperidin-4-yl)ethoxy]-5-(trifluoromethyl)pyridin-3-yl}-9H-purine-2-carbonitrile,
6-{6-[2-(1-ethylpiperidin-4-yl)ethoxy]-5-(trifluoromethyl)pyridin-3-yl}-9-methyl-9H-purine-2-carbonitrile,
9-methyl-6-[6-{2-[1-(1-methyl-L-prolyl)piperidin-4-yl]ethoxy}-5-(trifluoromethyl)pyridin-3-yl]-9H-purine-2-carbonitrile,
6-{4-[2-(1-ethylpiperidin-4-yl)ethoxy]-3-(trifluoromethyl)phenyl}-9-(tetrahydrofuran-3-ylmethyl)-9H-purine-2-carbonitrile, and
6-{6-[2-(1-cyclobutylpiperidin-4-yl)ethoxy]-5-(trifluoromethyl)pyridin-3-yl}-9-methyl-9H-purine-2-carbonitrile,
and salts thereof.

Examples of another specific compound contained in the compound of the formula (I) or a salt thereof include the following compounds.

2-[4-(2-{4-[2-cyano-7-(2-hydroxyethyl)-7H-pyrrolo[2,3-d]pyrimidin-4-yl]-2-(trifluoromethyl)phenoxy}ethyl)piperidin-1-yl]-N,N-dimethylacetamide,
4-{6-[2-(1-ethylpiperidin-4-yl)ethoxy]-5-(trifluoromethyl)pyridin-3-yl}-7-methyl-7H-pyrrolo[2,3-d]pyrimidine-2-carbonitrile,
4-{4-[2-(1-ethylpiperidin-4-yl)ethoxy]-3-(trifluoromethyl)phenyl}-7-(2-hydroxyethyl)-7H-pyrrolo[2,3-d]pyrimidine-2-carbonitrile,
7-methyl-4-[6-(2-{[(3R)-1-(1-methyl-D-prolyl)pyrrolidin-3-yl]oxy}ethoxy)-5-(trifluoromethyl)pyridin-3-yl]-7H-pyrrolo[2,3-d]pyrimidine-2-carbonitrile, and
4-{6-[(1-{[1-(2-hydroxy-2-methylpropyl)piperidin-4-yl]carbonyl}piperidin-4-yl)methoxy]-5-(trifluoromethyl)pyridin-3-yl}-7-methyl-7H-pyrrolo[2,3-d]pyrimidine-2-carbonitrile,
and salts thereof.

In the compound of the formula (I), tautomers or geometric isomers may be present depending on the types of substituents. In the present specification, the compound of the formula (I) is described as only one form of isomers, however the present invention also includes other isomers, and also includes a separated isomer or a mixture thereof.

In addition, the compound of the formula (I) may have an asymmetric carbon atom or axial asymmetry, and an optical isomer based on this may be present. The present invention also includes a separated optical isomer of the compound of the formula (I) or a mixture thereof.

Furthermore, the present invention also includes a pharmaceutically acceptable prodrug of the compound of the formula (I). The pharmaceutically acceptable prodrug is a compound having a group which can be converted into an amino group, a hydroxyl group, or a carboxyl group by solvolysis or under physiological conditions. As the group forming the prodrug, groups described in Prog. Med., 1985, Vol. 5, pp. 2157-2161, and "Pharmaceutical Research and Development, Drug Design" (Hirokawa Publishing Company), 1990, Vol. 7, pp. 163-198 are exemplified.

In addition, a salt of the compound of the formula (I) is a pharmaceutically acceptable salt of the compound of the formula (I), and an acid addition salt or a salt with a base may be formed depending on the types of substituents. Specifically, acid addition salts of inorganic acids such as hydrochloric acid, hydrobromic acid, hydroiodic acid, sulfuric acid, nitric acid, and phosphoric acid, and organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methane sulfonic acid, ethane sulfonic acid, benzene sulfonic acid, p-toluene sulfonic acid, aspartic acid, and glutamic acid, salts of inorganic bases such as sodium, potassium, magnesium, calcium, and aluminum, and organic bases such as methylamine, ethylamine, ethanolamine, lysine, and ornithine, salts of various amino acids such as acetylleucine and the like and amino acid derivatives, and ammonium salt are exemplified.

Furthermore, the present invention also includes various hydrates or solvates of the compound of the formula (I) or a salt thereof, and crystal polymorphism substances. In addition, the present invention also includes a compound labeled with various radioactive or non-radioactive isotopes.

(Preparation Method)

The compound of the formula (I) and a salt thereof can be prepared by applying various known synthetic methods using the characteristics based on the basic structure thereof or the types of substituents. At that time, it may be effective in a preparing technology that the functional group is substituted with a suitable protective group (group which can be easily converted into the functional group) at the stage from a starting material to an intermediate depending on the types of functional groups. As such a protective group, the protective groups described in "Greene's Protective Groups in Organic Synthesis (4th edition, 2006)" written by P. G. M. Wuts and T. W. Greene can be exemplified, and these may be suitably selected and used depending on the reaction conditions. In such a method, the protective group is introduced, a reaction is performed, and the protective group is removed, if necessary. By doing this, it is possible to obtain a desired compound.

In addition, the prodrug of the compound of the formula (I) can be prepared by further performing the reaction by introducing a specific group at the stage from a starting material to an intermediate in the same manner as that of the above-described protective group, or using the obtained compound of the formula (I). The reaction can be performed by applying methods known to those skilled in the art such as general esterification, amidation, or dehydration.

Hereinafter, representative preparation methods of the compound of the formula (I) will be described. Each preparation method can also be performed with reference to references described in the description. Moreover, the preparation method of the present invention is not limited to examples described below.

(First Preparation Method)

[Chem. 6]

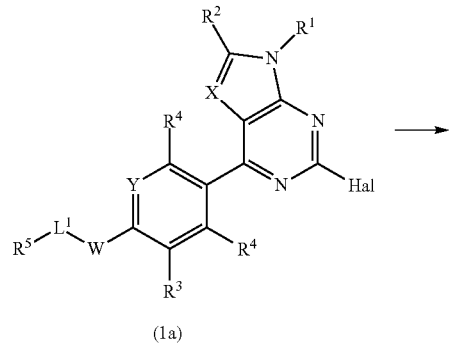

(1a)

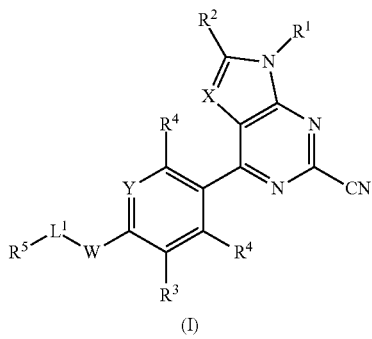

(I)

(In the formula, Hal represents a halogen. The same shall apply hereinafter.)

A compound (I) of the present invention can be obtained by subjecting a compound (1a) to a cyanation reaction.

In this reaction, the compound (1a) and a predetermined cyanation reagent are used in equivalent amounts, or either thereof in an excess amount, and the mixture thereof is stirred usually for 0.1 hours to 5 days under heating to reflux from room temperature, in a solvent which is inert to the reaction or in the absence of a solvent, in the presence of a predetermined catalyst. Examples of the solvent used in this reaction, which are not particularly limited, include aromatic hydrocarbons such as benzene, toluene and xylene, ethers such as diethylether, tetrahydrofuran, dioxane and dimethoxyethane, halogenated hydrocarbons such as dichloromethane, 1,2-dichloroethane and chloroform, N-methylpyrrolidone, N,N-dimethylformamide, N,N-dimethylacetamide, dimethyl sulfoxide, ethyl acetate, acetonitrile and a mixture thereof. Examples of the cyanation reagent include zinc cyanide. Examples of the predetermined catalyst include palladium (II) trifluoroacetate and tetrakis(triphenylphosphine)palladium (0). It is in some cases advantageous for smooth progress of the reaction to perform the reaction in the presence of phosphines such as triphenylphosphine or 2-(di-tert-butylphosphino)biphenyl.

(Second Preparation Method)

[Chem. 7]

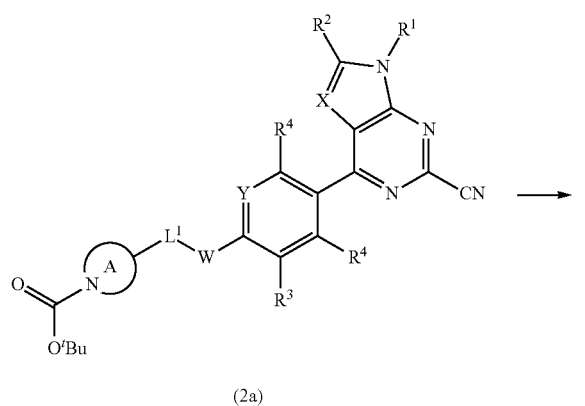

(2a)

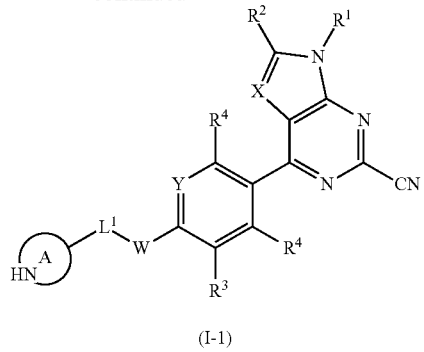

(I-1)

(In the formula, A represents nitrogen-containing heterocycloalkyl which may be substituted. The same shall apply hereinafter.)

A compound (I-1) of the present invention can be obtained by subjecting a compound (2a) to a Boc-elimination reaction.

In this reaction, the compound (2a) and an ethyl acetate solution of hydrogen chloride are used in equivalent amounts, or either thereof in an excess amount, and the mixture thereof is stirred usually for 0.1 hours to 5 days under heating to reflux from room temperature, in a solvent which is inert to the reaction or in the absence of a solvent. Examples of the solvent used in this reaction, which are not particularly limited, include aromatic hydrocarbons such as benzene, toluene and xylene, ethers such as diethylether, tetrahydrofuran, dioxane and dimethoxyethane, halogenated hydrocarbons such as dichloromethane, 1,2-dichloroethane and chloroform, N-methylpyrrolidone, N,N-dimethylformamide, N,N-dimethylacetamide, dimethyl sulfoxide, ethyl acetate, acetonitrile and a mixture thereof. In this reaction, a dioxane solution of hydrogen chloride, trifluoroacetic acid, or the like other than the ethyl acetate solution of hydrogen chloride can be used.

(Third Preparation Method)

[Chem. 8]

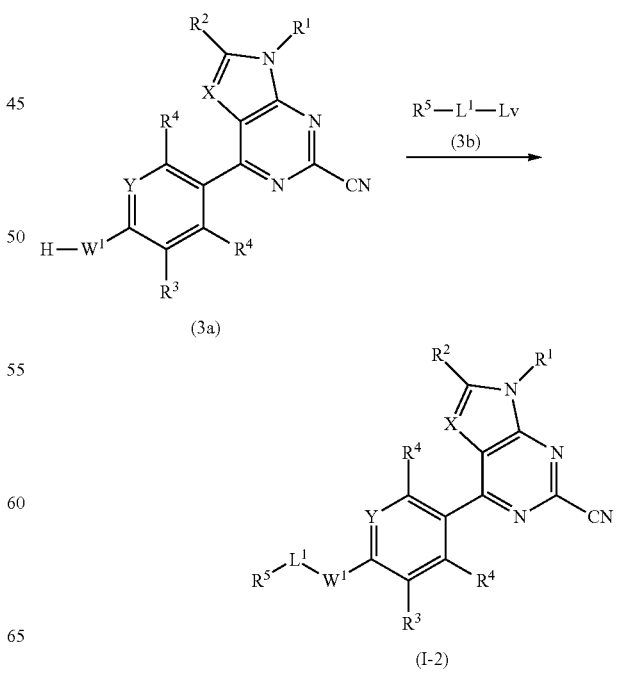

(In the formula, Lv represents a leaving group, and $W^1$ represents —O— or —S—. The same shall apply hereinafter.)

A compound (I-2) of the present invention can be obtained by subjecting a compound (3a) and a compound (3b) to an alkylation reaction. Here, examples of the leaving group include a halogen, a methanesulfonyloxy group and a p-toluenesulfonyloxy group.

In this reaction, the compound (3a) and the compound (3b) are used in equivalent amounts, or either thereof in an excess amount, and the mixture thereof is stirred usually for 0.1 hours to 5 days under heating to reflux from room temperature, in a solvent which is inert to the reaction or in the absence of a solvent, in the presence of a predetermined basic reagent. Examples of the solvent used in this reaction, which are not particularly limited, include aromatic hydrocarbons such as benzene, toluene and xylene, ethers such as diethylether, tetrahydrofuran, dioxane and dimethoxyethane, halogenated hydrocarbons such as dichloromethane, 1,2-dichloroethane and chloroform, N-methylpyrrolidone, N,N-dimethylformamide, N,N-dimethylacetamide, dimethyl sulfoxide, ethyl acetate, acetonitrile, and a mixture thereof. Examples of the basic reagent include organic bases such as triethylamine, N,N-diisopropyl ethylamine and N-methylmorpholine, or inorganic bases such as potassium carbonate, sodium carbonate, potassium hydroxide and sodium hydride. In addition, it is in some cases advantageous for smooth progress of the reaction to perform the reaction in the presence of potassium iodide or the like.

[References]

"Organic Functional Group Preparations" written by S. R. Sandler and W. Karo, 2nd edition, Vol. 1, Academic Press Inc., 1991

"Courses in Experimental Chemistry" (5th edition) edited by The Chemical Society of Japan, Vol. 14 (2005) (Maruzen Co., Ltd.)

(Fourth Preparation Method)

[Chem. 9]

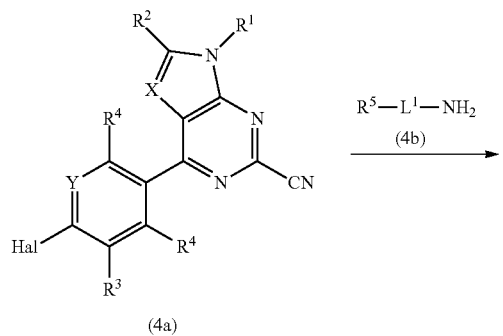

A compound (I-3) of the present invention can be obtained by subjecting a compound (4a) and a compound (4b) to an ipso substitution reaction.

In this reaction, the compound (4a) and the compound (4b) are used in equivalent amounts, or either thereof in an excess amount, and the mixture thereof is stirred usually for 0.1 hours to 5 days under heating to reflux from room temperature, in a solvent which is inert to the reaction or in the absence of a solvent, in the presence of a predetermined basic reagent. Examples of the solvent used in this reaction, which are not particularly limited, include aromatic hydrocarbons such as benzene, toluene and xylene, ethers such as diethylether, tetrahydrofuran, dioxane and dimethoxyethane, halogenated hydrocarbons such as dichloromethane, 1,2-dichloroethane and chloroform, N-methylpyrrolidone, N,N-dimethylformamide, N,N-dimethylacetamide, dimethyl sulfoxide, ethyl acetate, acetonitrile, and a mixture thereof. Examples of the basic reagent include organic bases such as triethylamine, N,N-diisopropyl ethylamine and N-methylmorpholine, or inorganic bases such as potassium carbonate, sodium carbonate, potassium hydroxide and sodium hydride. In addition, it is in some cases advantageous for smooth progress of the reaction to heat the reaction mixture by microwave irradiation.

Various substituents on the groups $R^1$ and $R^5$ in the compound of the formula (I) can be easily converted to other functional groups using the compound of the formula (I) as a starting material by using a reaction described in Examples described below, a reaction apparent to those skilled in the art, or modified methods thereof. For example, processes that those skilled in the art can usually employed such as reduction, halogenation, deprotection, hydrolysis, amidation, amination, oxidation, ureation, reductive amination, acylation, O-alkylation, N-alkylation, reductive alkylation, and epoxidation can be performed in arbitrary combination thereof.

(Preparation of Starting Compound)

In the preparation methods above, a starting compound can be prepared by using, for example, the methods below, the methods described in Preparation Examples as described later, known methods, or modified methods thereof.

(Starting Material Synthesis 1)

[Chem. 10]

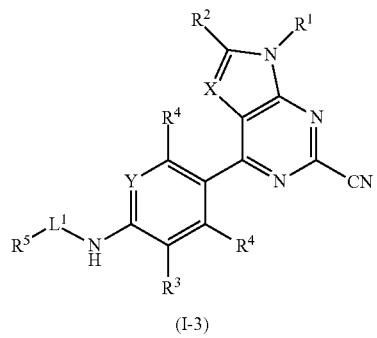

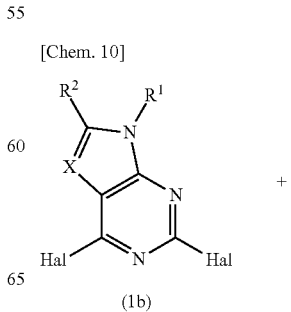

(Starting Material Synthesis 2)

[Chem. 11]

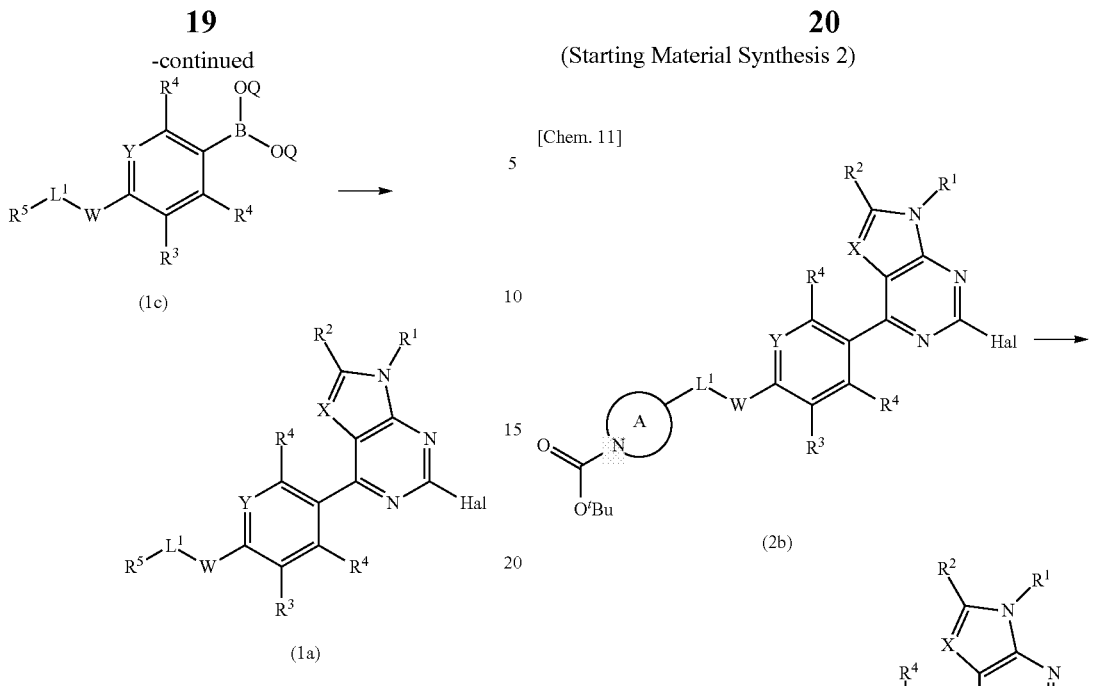

(In the formula, Hal's are the same as or different from each other, and Hal represents a halogen. Q's are the same as or different from each other, and Q represents H, lower alkyl, or lower alkylene in which two Q are combined to be one.)

The preparation method is a method of preparing a starting compound (1a) in the first preparation method.

A starting compound (1a) can be obtained by subjecting a compound (1b) and a compound (1c) to a coupling reaction.

In this reaction, the compound (1b) and the compound (1c) are used in equivalent amounts, or either thereof in an excess amount, and the mixture thereof is stirred usually for 0.1 hours to 5 days under heating to reflux from room temperature, in a solvent which is inert to the reaction, in the presence of a basic reagent and a palladium catalyst. This reaction is preferably performed in an inert gas atmosphere. Examples of the solvent used in this reaction, which are not particularly limited, include aromatic hydrocarbons such as benzene, toluene and xylene, ethers such as diethylether, tetrahydrofuran, dioxane and dimethoxyethane, halogenated hydrocarbons such as dichloromethane, 1,2-dichloroethane and chloroform, alcohols such as methanol, ethanol, 2-propanol and butanol, N,N-dimethylformamide, dimethyl sulfoxide, water, and a mixed solvent thereof. Preferred examples of the base include inorganic bases such as potassium carbonate, sodium carbonate, cesium carbonate, potassium acetate and potassium hydroxide. Preferred examples of the palladium catalyst include tetrakis(triphenylphosphine)palladium, dichlorobis(triphenylphosphine)palladium, and [1,1'-bis(diphenylphosphino)ferrocene]palladium chloride. In addition, it is in some cases advantageous for smooth progress of the reaction to heat the reaction mixture by microwave irradiation.

[References]

"Metal-Catalyzed Cross-Coupling Reactions" edited by A. d. Meijere and F. Diederich, 1st edition, VCH Publishers Inc., 1997

"Courses in Experimental Chemistry" (5th edition) edited by The Chemical Society of Japan, Vol. 13 (2005) (Maruzen Co., Ltd.)

The preparation method is a method of preparing a starting compound (2a) in the second preparation method.

The starting compound (2a) can be obtained by subjecting a compound (2b) to a cyanation reaction.

This reaction can be performed in the same manner as in the first preparation method. The compound (2b) is the compound (1a) which is nitrogen-containing heterocycloalkyl in which $R^5$ is protected by Boc.

(Starting Material Synthesis 3)

[Chem. 12]

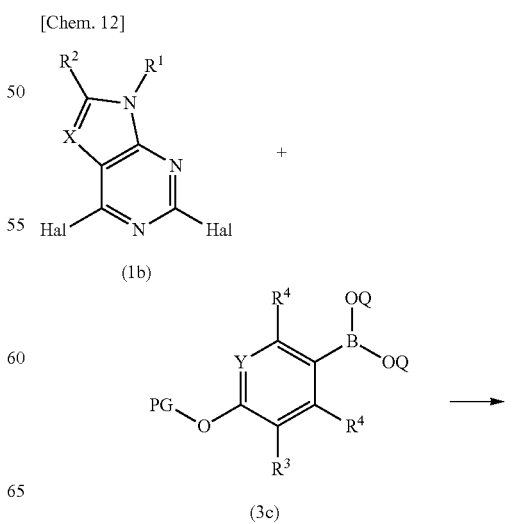

21

-continued

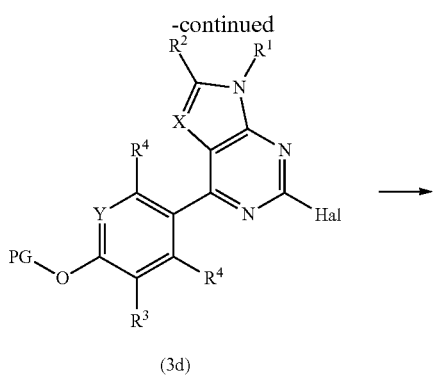

(3d)

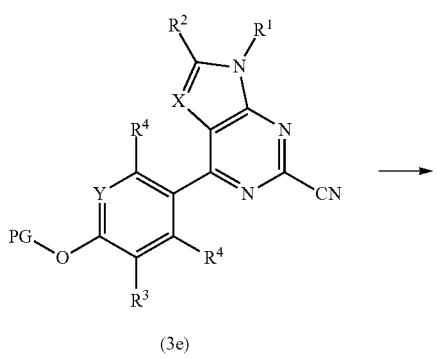

(3e)

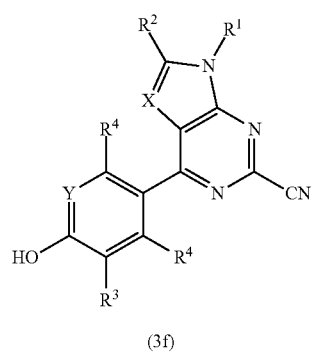

(3f)

(In the formula, PG represents a protective group.)

The preparation method is a method of preparing a compound (3f) in which $W^1$ in the starting compound (3a) in the third preparation method is —O—.

A compound (3d) can be obtained by subjecting the compound (1b) and a compound (3c) to a coupling reaction. Examples of the protective group include a p-methoxybenzyl group and the like. This reaction can be performed in the same manner as in the starting material synthesis 1.

A compound (3e) can be obtained by subjecting the compound (3d) to a cyanation reaction. This reaction can be performed in the same manner as in the first preparation method.

The compound (3f) can be obtained by deprotecting the compound (3e).

22

(Starting Material Synthesis 4)

[Chem. 13]

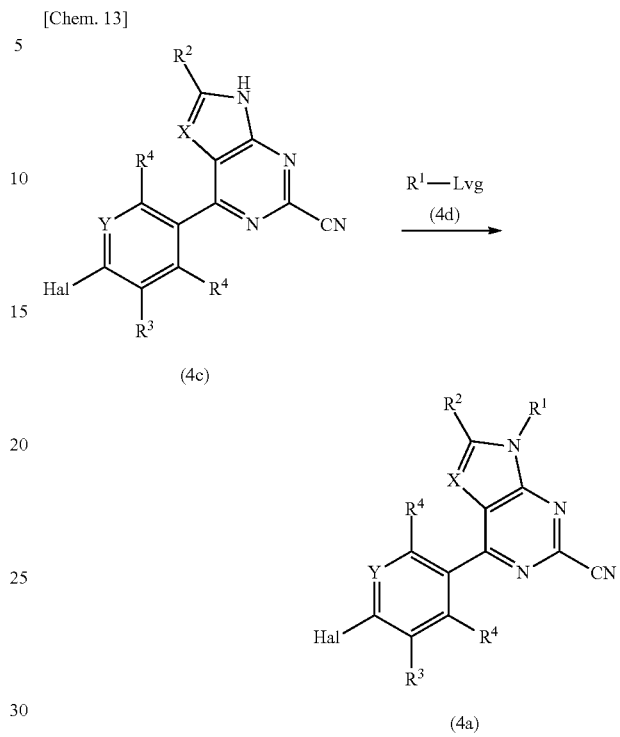

(In the formula, Lvg represents Lv or —OH.)

The preparation method is a method of preparing a starting compound (4a) in the fourth preparation method.

In a case where Lvg is Lv, the starting compound (4a) can be obtained by subjecting a compound (4c) and a compound (4d) to alkylation. This reaction can be performed in the same manner as in the third preparation method.

In a case where Lvg is —OH, the starting compound (4a) can be obtained by subjecting the compound (4c) and the compound (4d) to a Mitsunobu reaction. In this reaction, the compound (4c) and the compound (4d) are used in equivalent amounts, or either thereof in an excess amount, and the mixture thereof is stirred usually for 0.1 hours to 5 days under heating to reflux from room temperature, in a solvent which is inert to the reaction or in the absence of a solvent, in the presence of a predetermined organic phosphine, and ester or amide of azodicarboxylic acid. Examples of the solvent used in this reaction, which are not particularly limited, include aromatic hydrocarbons such as benzene, toluene and xylene, ethers such as diethylether, tetrahydrofuran, dioxane and dimethoxyethane, halogenated hydrocarbons such as dichloromethane, 1,2-dichloroethane, and chloroform, N-methylpyrrolidone, N,N-dimethylformamide, N,N-dimethylacetamide, dimethyl sulfoxide, ethyl acetate, acetonitrile, and a mixture thereof. Examples of the organic phosphine include triphenylphosphine and tributylphosphine. Examples of the ester or amide of azodicarboxylic acid include diethyl azodicarboxylate, bis(2-methoxyethyl) azodicarboxylate and 1,1'-(azodicarbonyl)dipiperidine.

The compound of the formula (I) is isolated and purified as a free compound, a salt thereof, a hydrate, a solvate, or a crystal polymorphism substance. The salt of the compound of the formula (I) can be prepared by a common salt formation reaction.

Isolation and purification are carried out by applying usual chemical operations such as extraction, fractional crystallization, and various types of fractional chromatography.

Various isomers can be prepared by selecting a suitable starting compound, or can be separated using a difference in physicochemical properties among the isomers. For example, optical isomers are obtained by general optical resolution methods (for example, fractional crystallization leading to a diastereomeric salt with an optically active base or an acid, or chromatography using a chiral column) of a racemic mixture, and can also be prepared from a suitable optically active starting compound.

The pharmacological activity of the compound of the formula (I) was confirmed by the tests shown below.

Test Example 1 Measurement of a In Vitro Human Cathepsin S Inhibitory Activity

5 µL of a human cathepsin S enzyme (R&D1183-CY-010) was added to a 96-well plate so as to be 20 ng/well. Next, 10-fold dilution of the test compound (a 10 mM DMSO solution) was serially performed with a buffer solution for assay (a solution of 50 mM sodium methoxide, 250 mM sodium chloride and 5 mM dithiothreitol (DTT), adjusted to pH=4.5 with 1 N hydrochloric acid) six times such that the final concentration becomes 0.1 nM to 10 µM then, 20 µL of each of the solutions was added to the wells (the final DMSO concentration was 0.1%), and 25 µL of synthetic substrate VVR-AMC (3211-V manufactured by PEPTIDE INSTITUTE, INC.) was added thereto such that the final concentration becomes 40 µM, thereby starting a enzyme reaction. A fluorescence intensity (an excitation wavelength: 380 nm and a fluorescent wavelength: 460 nm) was measured at 37° C. for 10 minutes immediately after the start of the reaction using a fluorescence spectrophotometer (SPECTRA MAX GEMINI, manufactured by Molecular Devices Corporation), and the reaction rate at the time (5 minutes or 10 minutes) when linearity was observed was determined at each concentration of the test compound. A reaction rate at the time of not adding an enzyme in which the test compound was not added and a reaction rate at the time of adding an enzyme in which the test compound was not added were set to 100% inhibition and 0% inhibition, respectively, then, an inhibition rate at each concentration was determined, and $IC_{50}$ values were calculated by a linear regression method. The results are shown in Table 1. In the Table, Ex represents Example compound No., and Data 1 represents an $IC_{50}$ value (nM) of the human cathepsin S inhibitory activity.

TABLE 1

| Ex | Data1 |
| --- | --- |
| 2 | 2.3 |
| 3 | 2.6 |
| 5 | 4.2 |
| 6 | 3.4 |
| 7 | 6.2 |
| 8 | 1.6 |
| 10 | 2.7 |
| 11 | 1.9 |
| 12 | 2.7 |
| 13 | 2.7 |
| 14 | 2.3 |
| 15 | 3.4 |
| 16 | 4.7 |
| 19 | 1.7 |
| 20 | 3.8 |
| 21 | 1.9 |
| 23 | 1.9 |
| 24 | 0.76 |
| 25 | 1.6 |
| 26 | 1.2 |
| 27 | 1.9 |
| 28 | 1.4 |
| 29 | 3.5 |
| 30 | 4.7 |
| 31 | 2.7 |
| 32 | 2.3 |
| 33 | 6.1 |
| 34 | 1.7 |
| 35 | 2.1 |
| 36 | 8.9 |
| 37 | 3.6 |
| 38 | 4.5 |
| 39 | 1.0 |
| 40 | 3.1 |
| 41 | 4.8 |
| 42 | 2.9 |
| 44 | 3.6 |
| 45 | 2.6 |
| 47 | 2.1 |
| 50 | 2.7 |
| 51 | 3.4 |
| 52 | 2.6 |
| 54 | 3.9 |
| 56 | 3.3 |
| 58 | 2.6 |
| 65 | 3.1 |
| 66 | 2.9 |
| 68 | 2.2 |
| 70 | 2.2 |
| 71 | 2.0 |
| 72 | 1.6 |
| 73 | 2.0 |
| 74 | 2.2 |
| 75 | 2.5 |
| 76 | 3.0 |
| 77 | 2.7 |
| 78 | 2.6 |
| 79 | 1.4 |
| 80 | 3.5 |
| 81 | 3.2 |
| 82 | 4.5 |
| 83 | 3.1 |
| 84 | 1.3 |
| 85 | 3.3 |
| 86 | 1.9 |
| 87 | 2.7 |
| 88 | 2.4 |
| 89 | 3.1 |
| 90 | 3.0 |
| 91 | 2.1 |
| 92 | 2.0 |
| 93 | 2.1 |
| 94 | 3.6 |
| 95 | 2.3 |
| 96 | 4.0 |
| 97 | 3.8 |
| 101 | 2.8 |
| 102 | 2.0 |
| 103 | 3.7 |
| 104 | 7.8 |
| 105 | 2.2 |
| 106 | 2.8 |
| 107 | 3.1 |
| 108 | 3.2 |
| 109 | 2.4 |
| 110 | 2.3 |
| 111 | 4.3 |
| 112 | 8.9 |
| 113 | 1.9 |
| 114 | 2.9 |
| 115 | 3.3 |
| 116 | 2.5 |
| 117 | 2.3 |
| 118 | 2.3 |
| 119 | 2.7 |
| 120 | 2.1 |
| 121 | 2.4 |

TABLE 1-continued

| Ex | Data1 |
|---|---|
| 122 | 1.7 |
| 135 | 2.1 |
| 136 | 1.5 |
| 137 | 1.0 |
| 138 | 2.7 |
| 139 | 2.1 |
| 140 | 2.1 |
| 141 | 2.0 |
| 142 | 1.5 |
| 143 | 1.5 |
| 144 | 2.8 |
| 145 | 1.0 |
| 146 | 3.2 |
| 147 | 2.4 |
| 148 | 2.8 |
| 149 | 2.7 |
| 150 | 1.7 |
| 152 | 2.2 |
| 153 | 1.6 |
| 154 | 2.4 |
| 155 | 1.5 |
| 156 | 2.4 |
| 157 | 2.1 |
| 158 | 2.4 |
| 159 | 2.7 |
| 160 | 2.4 |

Test Example 2 Evaluation of In Vitro MHC Class II Expression Inhibitory Effect Using Mouse Spleen Cells (Cell Evaluation System)

In antigen-presenting cells, the inhibition of cathepsin S inhibits the expression of MHC class II molecules. As a result, antibody production is inhibited, and decrease in an immune response occurs. For an increased expression of MI-IC class II in B cells, the inhibitory effect of the compound represented by formula (I) was examined.

First, spleen cells collected from C57BL/6 mice were seeded in a 96-well plate so as to be a $1 \times 10^5$ cells/well, then, 5-fold dilution of 10 mM DMSO solution of the test compound was serially performed with RPMI 1640 medium (including 10% fetal bovine serum (FCS), $5 \times 10^{-5}$ M 2-mercaptoethanol, 50 IU/mL penicillin and 50 μg/mL streptomycin) nine times such that the final concentration becomes 0.026 nM to 10 μM, and the resultant products were added thereto (the final DMSO concentration was 0.1%). At the same time, LPS (Sigma L4005) was added to the wells such that the final concentration becomes 2 μg/mL, and culture was performed at 37° C. for 48 hours in 5% $CO_2$. After culturing, the cells were stained at 4° C. for 20 minutes with PE-labeled streptavidin (BD BIOSCIENCE 554061) and biotin-labeled YAe antibody (EBIOSCIENCE 13-5741-85) together with FITC-labeled anti-mouse B220 antibody (BD BIOSCIENCE 553088), and an expression level (fluorescence intensity of YAe-biotin/streptavidin-PE) of MHC class II to which Ea peptide in B220 positive B cells was bonded was measured using a flow cytometry system (Guava EasyCyte Plus System, manufactured by Millipore Corporation). A value at the time of unstimulation of LPS in which the test compound was not added and a value at the time of stimulation of LPS in which the test compound was not added were set to 100% inhibition and 0% inhibition, respectively, then, an inhibition rate at each concentration was determined, and $IC_{50}$ values were calculated by a linear regression method. The results are shown in Table 2. In the Table, Ex represents Example compound No., and Data 2 represents an $IC_{50}$ value (nM).

TABLE 2

| Ex | Data2 |
|---|---|
| 2 | 1.2 |
| 3 | 1.0 |
| 6 | 0.69 |
| 15 | 2.1 |
| 19 | 0.7 |
| 21 | 1.0 |
| 23 | 3.0 |
| 24 | 0.80 |
| 26 | 0.61 |
| 27 | 1.3 |
| 28 | 0.81 |
| 29 | 0.66 |
| 30 | 0.97 |
| 39 | 0.61 |
| 40 | 0.85 |
| 41 | 1.1 |
| 47 | 2.0 |
| 52 | 1.8 |
| 54 | 0.94 |
| 58 | 2.0 |
| 66 | 2.1 |
| 70 | 0.76 |
| 71 | 1.3 |
| 72 | 0.73 |
| 77 | 1.5 |
| 79 | 2.5 |
| 88 | 2.3 |
| 105 | 0.91 |
| 106 | 3.2 |
| 110 | 0.91 |
| 116 | 1.8 |
| 120 | 1.0 |
| 122 | 0.87 |
| 135 | 0.89 |
| 141 | 0.65 |
| 158 | 0.62 |

From the results of the above Test 2, it was confirmed that some compounds of the formula (I) inhibit the MHC class II increased expression in B cells.

Test Example 3 Evaluation of Ex Vivo MHC Class II Expression Inhibitory Effect Using Mouse Peripheral Blood The expression inhibitory effect of MHC class II molecules was evaluated in an ex vivo system.

The test compound was orally administered into C57BL/6mice, and the inhibitory effect with respect to the increased expression of MHC class II in B cells in peripheral blood after oral administration was examined. That is, 10 mL/kg of the test compound dissolved in a vehicle (30% propylene glycol solvent (propylene glycol:cured castor oil (HCO40):Tween 80=4:2:1)/HCl (2 equivalents with respect to the test compound)/water) was orally administered (dose: 0.1 mg/kg, 0.3 mg/kg, 1 mg/kg, or 3 mg/kg) to a C57BL/6mice, and the peripheral blood was collected after 3 hours. 10 μL of RPMI 1640 medium (including $5 \times 10^{-5}$ M of 2-mercaptoethanol, 50 IU/mL of penicillin, and 50 μg/mL of streptomycin) or 10 μL of LPS adjusted with the medium such that the final concentration becomes 100 μg/mL was added to 90 μL of the peripheral blood, and culture was performed at 37° C. for 15 hours in 5% $CO_2$. After culturing, the cells were stained at 4° C. for 30 minutes with FITC-labeled anti-mouse I-A/I-E antibody (BD BIOSCIENCE 553623) and PE-labeled B220 antibody (BD BIOSCIENCE 553090), and hemolysis and fixation were performed at 37° C. for 10 minutes using a buffer (BD BIOSCIENCE Phosflow Lyse/Fix Buffer 558049). After washing, using a flow cytometry system (FACSCanto II, manufactured by BD BIOSCIENCE), an expression level of MHC class II on a B220 positive B cell surface was measured by using a fluorescence intensity of FITC (hereinafter, referred to as MFI) as an indicator. The difference between a MFI at the time of stimulation of LPS and a MFI at the time of unstimulation of LPS was set to a ΔMFI, a ΔMFI of a mouse in which 10 mL/kg of only vehicle was administered was set to 1, and the inhibition rate of ΔMFI by the test compound administration was calculated.

From the results of the above Test 3, the compound of Example 28 exhibited 40±1.4% inhibition (0.3 mg/kg, p<0.001), the compound of Example 39 exhibited 61±1.2% inhibition (1 mg/kg, p<0.001), and the compound of Example 158 exhibited 59±1.5% inhibition (0.3 mg/kg, p<0.001), and thus, the increased expression of MHC class II was significantly inhibited. That is, it was confirmed that some compounds of the formula (I) inhibit the increased expression of MHC class II in peripheral blood B cells.

Test Example 4 Evaluation of Antibody Production Inhibitory Effect in Mouse OVA-Induced Antibody Production Model Evaluation of an antibody production inhibitory effect in vivo was performed.

The BALB/c male mice were sensitized by intraperitoneal administration of 200 μL of an emulsion consisting of 100 μg of ovalbumin (OVA) (SIGMA A5503) and 100 μL of a complete Freund's adjuvant (CFA) (DIFCO 231131) (Day 0), and a week after that, the mice were sensitized by intraperitoneal administration of 200 μL of an emulsion consisting of 50 μg of OVA and 100 μL of an incomplete Freund's adjuvant (IFA) (DIFCO 263910) (Day 7). The test compound dissolved in a vehicle (30% propylene glycol solvent (propylene glycol: HCO40:Tween 80=4:2:1)/HCl (2 equivalents with respect to the test compound)/water) was orally administered (dose: 0.3 mg/kg, 1 mg/kg, or 3 mg/kg) at 10 mL/kg/day from Day 0 to Day 14, and an OVA specific IgG antibody titer in blood plasma at Day 14 was evaluated. Measurement of antibody titer was carried out using a blood plasma sample which was diluted 40,000 times by an ELISA method, and the antibody titer was represented as a ratio with respect to control blood plasma. An antibody titer of a mouse to which the vehicle was orally administered at 10 mL/kg/day from Day 0 to Day 14 was set to 0% inhibition, an antibody titer of a normal mouse to which the vehicle was orally administered at 10 mL/kg/day from Day 0 to Day 14 and which was not sensitized with OVA was set to 100% inhibition, and the inhibition rate at the time of the test compound administration was calculated.

From the results of the above Test 4, the compound of Example 2 exhibited 61±10% inhibition (1 mg/kg, p=0.02), the compound of Example 28 exhibited 83±2% inhibition (1 mg/kg, p<0.001), and the compound of Example 39 exhibited 74±8% inhibition (0.3 mg/kg, p<0.001), and thus, the antibody production was significantly inhibited. That is, it was confirmed that some compounds of the formula (I) inhibit the antibody production.

Test Example 5 Evaluation of SLE Onset Inhibitory Effect in Spontaneous Model Using NZB/W F1 Mouse NZB/W F1 mice are used as a model of SLE that spontaneously develops a condition close to humans (Helyer et al, Proceedings of the university otago medical school (New Zealand), 1961, Vol. 39, p. 3; Advances in Immunology, 1985, Vol. 37, p. 269-390; Perry et al, Journal of Biomedicine and Biotechnology, 2011, Article ID 271694, Review Article).

NZB/W F1 female mice were grouped on the basis of a urine protein level at the time of 20 weeks old, an anti-dsDNA antibody titer (IgG, IgM), an expression level of MHC class II in peripheral blood B cells, and a body weight. At this time, an individual having greater than 100 mg/dL of urine protein was excluded. After 20 weeks old, the test compound was orally administered once a day, urine collection and blood collection were performed every 4 weeks thereafter, and time-dependent transitions of urine protein, an anti-dsDNA antibody titer, and an expression level of MHC class II in peripheral blood B cells were evaluated. The evaluation ended at the time when urine protein-increased individual in the vehicle administration group reached the majority (at the time of 41 weeks old).

From the results of the above Test 5, at the time of 41 weeks old, urine protein of individuals of 6 cases among 8 cases in the vehicle administration group was 1,000 mg/dL or more. In the compound administration group (dose: 0.3 mg/kg) of Example 39, urine protein of all individuals of 10 cases was 100 mg/dL or less. Therefore, it was confirmed that the compound of Example 39 included in the formula (I) inhibits an increase of urine protein, and maintains kidney functions.

In addition, in the above Test 5, an anti-dsDNA IgG antibody titer at the time of 41 weeks old was measured by the ELISA method. The average of an anti-dsDNA IgG antibody titer of the vehicle administration group 6 cases was 69,375±20,607 (mU/mL). In the compound administration group (dose: 0.3 mg/kg) of Example 39, the average of an anti-dsDNA IgG antibody titer of 10 cases was 9,263±1,700 (mU/mL). Therefore, it was confirmed that the compound of Example 39 included in the formula (I) inhibits an increase of an anti-dsDNA antibody titer.

Furthermore, a pathology evaluation of kidney tissue in the above Test 5 was performed. A formalin-fixed paraffin-embedded section of kidney tissue was prepared, then, a specimen was prepared by periodic acid-methenamine-silver (PAM) staining, and the specimen was observed with a microscope. In accordance with histological classification of lupus nephritis by WHO, a histopathological image was classified into Class I (normal glomerulus), Class II (mesangium lesion), Class III (focal segmental glomerulonephritis), Class IV (diffuse glomerulonephritis), and Class VI (progressive sclerosing lupus nephritis).

From the results of the above Test 5, it was confirmed that the compound of Example 39 included in the formula (I) can be used for preventing and/or treating SLE.

From the above results, the compound of the formula (I) or salts thereof can be used for preventing and/or treating autoimmune disease, allergic disease, graft rejection of an organ, bone marrow or tissue, SLE, or lupus nephritis.

As an aspect of the graft rejection of an organ, bone marrow or tissue, antibody-related type rejection in which B cells are involved and T cell-related type rejection in which T cells are involved can be exemplified. As another aspect, antibody-related type rejection in which B cells are involved can be exemplified. As an aspect of the autoimmune disease, rheumatoid arthritis, psoriasis, ulcerative colitis, Crohn's disease, systemic lupus erythematosus, Sjogren's syndrome, multiple sclerosis, and the like can be exemplified. As an aspect of the allergic disease, asthma, atopic dermatitis, and the like can be exemplified. As an aspect of SLE, lupus nephritis, central nervous system lupus, and the like can be exemplified. As an aspect of the lupus nephritis, nephrotic syndrome, renal failure, and the like can be exemplified.

A pharmaceutical composition which contains one or two or more kinds of the compound of the formula (I) or a salt thereof as an active ingredient can be prepared by methods which are commonly used using excipients commonly used in the art, that is, pharmaceutical excipients or pharmaceutical carriers.

Administration may be any form of an oral administration by a tablet, a pill, a capsule, a granule, powder or a liquid medicine, or a parenteral administration by intraarticular, intravenous or intramuscular injections, a suppository, an eye drop, an eye ointment, a transdermal solution, an ointment, a transdermal patch, a transmucosal solution, a transmucosal patch or an inhalant.

As a solid composition for the oral administration, a tablet, powder, a granule or the like can be used. In such a solid composition, one or two or more kinds of active ingredients are mixed with at least one of inert excipients. According to commonly used methods in the related art, the composition may contain an inert additive, for example, a lubricant, a disintegrant, a stabilizer or a solubilizer. The tablet or pill, if necessary, may be coated with a film of sugar, or a stomach-soluble or enteric-soluble substance.

A liquid composition for oral administration contains an emulsion, a solution preparation, a suspension, a syrup or an elixir which is a pharmaceutically acceptable, and contains a generally used inert diluent, for example, purified water or ethanol. In addition to the inert diluent, the liquid composition may contain adjuvants such as a solubilizing agent, a wetting agent and a suspension, a sweetener, a flavor, a fragrance or a preservative.

The injection for parenteral administration contains a sterile aqueous or non-aqueous solution preparation, a suspension or an emulsion. As the aqueous solvent, for example, distilled water for injection or physiological saline are included. As the non-aqueous solvent, for example, alcohols such as ethanol are included. Such a composition may further include an isotonic agent, a preservative, a wetting agent, an emulsifier, a dispersant, a stabilizer or a solubilizer. For example, these are sterilized by a filtration through a bacteria-catching filter, mixing of a germicide, or irradiation. In addition, these also can be used by preparing a sterile solid composition, and before using, dissolving or suspending the composition in sterile water or a sterile solvent for injection.

As an external preparation, an ointment, a plaster, a cream, a jelly, a poultice, a spray, a lotion, an eye drop and an eye ointment are contained. A generally used ointment base, lotion base, aqueous or non-aqueous liquid medicine, suspension and emulsion are contained.

The transmucosal agent such as an inhalent and a personal agent can be used in a solid, liquid or semi-solid form, and can be prepared according to methods known in the related art. For example, a known excipient, a pH adjuster, a preservative, a surfactant, a lubricant, a stabilizer and a thickener may be suitably added. In administration, it is possible to use a device for a suitable inhalation or insufflation. For example, using a known device such as a metered dose inhaler or a nebulizer, administration can be performed as a compound alone or a powder of a prescribed mixture, or as a solution or a suspension in combination with a carrier which is pharmaceutically acceptable. A dry powder inhaler may be an inhaler for single or multiple administrations, and it is possible to use dry powder or a powder-containing capsule. Alternatively, a suitable propellant, for example, a form of a pressurized aerosol spray using a suitable gas such as chlorofluoroalkane, hydrofluoroalkane or carbon dioxide may be used.

In a case of a normal oral administration, a suitable daily dose is about 0.001 mg/kg to 100 mg/kg of body weight, preferably 0.1 mg/kg to 30 mg/kg, and more preferably 0.1 mg/kg to 10 mg/kg, and this dose is administered once or 2 to 4 times. In a case of an intravenous administration, a daily dose is suitably about 0.0001 mg/kg to 10 mg/kg of body weight, and this dose is administered once or several times per day. In addition, as the transmucosal agent, about 0.001 mg/kg to 100 mg/kg of body weight is administered once or several times per day. The dose is suitably determined according to individual cases in consideration of symptoms, age and gender.

The dose differs depending on the types of an administration route, a dosage form, an administration site, an excipient and an additive, and the pharmaceutical composition of the present invention contains one or more kinds of the compound of the formula (I) or a salt thereof in which the active ingredient is 0.01% by weight to 100% by weight, and 0.01% by weight to 50% by weight as a certain aspect.

The compound of the formula (I) or a salt thereof can be used in combination with various therapeutic agents or preventive agents for which it is believed that the compound of the formula (I) or a salt thereof described above shows effectiveness. In the combined use, co-administration or separate administration in succession may be performed, or administration may be performed at a desired time interval. The co-administration formulation may be separately formulated, or may be a pharmaceutical composition including various therapeutic agents or preventive agents for which it is believed that the compound of the formula (I) or a salt thereof described above shows effectiveness and the compound of the formula (I) or a salt thereof.

EXAMPLES

Hereinafter, preparation methods for the compound of the formula (I) or salts thereof will be described in more detail with reference to Examples. Moreover, the present invention is not limited to compounds described in the following Examples. In addition, preparing methods for the starting compounds will be described in Preparation Examples. In addition, the preparation method for the compound of the formula (I) is not limited to only the preparation methods in specific Examples shown below, and the compound of the formula (I) can also be prepared by using a combination of the preparation methods or a method apparent to those skilled in the art.

The following abbreviations may be used in some cases in Examples, Preparation Examples, and Tables below.

PEx: Preparation Example No, Ex: Example No, PSyn: Preparation Example No prepared by the same method, Syn: Example No prepared in the same method, Str: chemical structural formula, DAT: physicochemical data.

ESI+: m/z value in mass spectrometry (ionization method ESI, $(M+H)^+$ unless otherwise specified), ESI-: m/z value (ionization method ESI, $(M-H)^-$ unless otherwise specified), EI: m/z value in mass spectrometry (ionization method EI, $(M)^+$ unless otherwise specified), CI: m/z value in mass spectrometry (ionization method CI, $(M+H)^+$ unless otherwise specified), APCI+: m/z value in mass spectrometry (atmospheric pressure chemical ionization method APCI, $(M+H)^+$ unless otherwise specified), APCI/ESI+: m/z value (simultaneous ionization of APCI and ESI, $(M+H)^+$ unless otherwise specified), NMR1: δ (ppm) at $^1H$ NMR in dimethyl sulfoxide-$d_6$, NMR2: δ (ppm) at $^1H$ NMR in $CDCl_3$, s: singlet (spectrum), d: doublet (spectrum), t: triplet (spectrum), q: quartet (spectrum), m: multiplet (spectrum), br: broad line (spectrum) (example: br-s).

Me: methyl, Et: ethyl, iPr: isopropyl, tBu: tert-butyl, Boc: tert-butoxycarbonyl, Bn: benzyl.

Hex: n-hexane, EtOAc: ethyl acetate, DMF: N,N-dimethylformamide, DMAc: N,N-dimethylacetamide, MeOH: methanol, EtOH: ethanol, $CH_2Cl_2$: dichloromethane, $CHCl_3$: chloroform, THF: tetrahydrofuran.

$Na_2CO_3$: sodium carbonate, $NaHCO_3$: sodium bicarbonate, $Na_2SO_4$: anhydrous sodium sulfate, $MgSO_4$: anhydrous magnesium sulfate.

M: mol/L.

HCl in a structural formula represents hydrochloride and Fum represents fumarate. The number before HCl represents a molar ratio. For example, HCl means monohydrochloride and 2HCl means dihydrochloride.

A compound marked with "Chiral" in a structural formula represents a compound which is an optically active substance.

In the following Tables, there are cases where PSyn No. is described as Syn, and it shows that the Example compound is prepared by the same method as in the compound of PEx No. For example, in the following Tables, there is a description of PSyn3 in Syn of Ex. 123, and it shows that Example 123 is prepared by the same method as in Preparation Example 3.

A description of "3+4" in Psyn and Syn shows that first, preparation is performed by the same method as in Example 3, and subsequently, using the product as a starting material, preparation is performed by the same method as in Example 4. For example, in the following Tables, there is a description of PSyn24+11 in Syn of Ex. 102, and it shows that Example 102 is prepared by the same method as in Preparation Example 24, and subsequently, preparation is performed by the same method as in Example 11.

In the following Tables, a compound marked with "#" in Example No. represents a compound which is not included in definition of Claims.

Thermal analysis (TG/DTA) was measured under the following conditions. DSC Q 2000 manufactured by TA Instruments, room temperature to 300° C., a temperature increase rate of 10° C./minutes, $N_2$ (50 mL/minutes), a sample pan made of aluminum. For a description of a heat absorption peak temperature, "near" means±2° C., and as another aspect, means±1° C.

Preparation Example 1

2-[4-ethoxy-3-(trifluoromethyl)phenyl]-4,4,5,5-tetramethyl-1,3,2-dioxaborolane (188 mg), $Na_2CO_3$ (217 mg), and tetrakis(triphenylphosphine)palladium (0) (29 mg) were added to a mixture of 2,4-dichloro-7-methyl-7H-pyrrolo[2,3-d]pyrimidine (100 mg), dioxane (2 mL), and water (0.3 mL) in an argon atmosphere, and the reaction mixture was stirred at 100° C. for 6 hours. After the reaction mixture was cooled to room temperature, extraction thereof was performed using EtOAc, and the extract was washed with water and saturated brine. The organic layer was dried over $MgSO_4$ and filtered, and the filtrate was concentrated under reduced pressure. The residue was purified by silica gel column chromatography (Hex:EtOAc=9:1 to 7:3), whereby 2-chloro-4-[4-ethoxy-3-(trifluoromethyl)phenyl]-7-methyl-7H-pyrrolo[2,3-d]pyrimidine (130 mg) was obtained as a light yellow solid.

Preparation Example 2

After 60% sodium hydride (17 mg) was added to a solution of tert-butyl 4-(2-hydroxyethyl)piperidine-1-carboxylate (109 mg) in DMF (2 mL) at 0° C. in a nitrogen atmosphere, the mixture was stirred at room temperature for 30 minutes. After the reaction mixture was cooled to 0° C., 4-bromo-1-fluoro-2-(methylsulfonyl)benzene (100 mg) was added thereto. The reaction mixture was stirred at 0° C. for 30 minutes, and stirred at room temperature for 3 hours. After a saturated aqueous ammonium chloride solution was added to the reaction mixture, extraction thereof was performed using EtOAc, and the extract was washed with water and saturated brine. The organic layer was dried over $Na_2SO_4$ and filtered, and the filtrate was concentrated under reduced pressure. The residue was purified by silica gel column chromatography (Hex:EtOAc=80:20 to 55:45), whereby tert-butyl 4-{2-[4-bromo-2-(methylsulfonyl)phenoxy]ethyl}piperidine-1-carboxylate (169 mg) was obtained as a colorless liquid.

Preparation Example 3

Zinc (29 mg), 2-(di-tert-butylphosphino)biphenyl (59 mg), zinc cyanide (63 mg), and palladium (II) trifluoroacetate (30 mg) were added to a solution of tert-butyl 4-{2-[4-(2-chloro-7-methyl-7H-pyrrolo[2,3-d]pyrimidin-4-yl)-2-(trifluoromethyl)phenoxy]ethyl}piperidine-1-carboxylate (480 mg) in DMAc (10 mL) at room temperature in an argon atmosphere, and the mixture was stirred at 110° C. for 5 hours. After the reaction mixture was cooled to room temperature, EtOAc was added thereto, followed by stirring, and the insoluble material was separated by filtration using Celite. This filtrate was washed with a saturated aqueous $NaHCO_3$ solution, water, and saturated brine. The organic layer was dried over $MgSO_4$ and filtered, and the filtrate was concentrated under reduced pressure. The residue was purified by silica gel column chromatography (Hex:EtOAc=9:1 to 1:1), whereby tert-butyl 4-{2-[4-(2-cyano-7-methyl-7H-pyrrolo[2,3-d]pyrimidin-4-yl)-2-(trifluoromethyl)phenoxy]ethyl}piperidine-1-carboxylate (236 mg) was obtained as a light yellow solid.

Preparation Example 4

Potassium carbonate (25.8 g) and 1-(chloromethyl)-4-methoxybenzene (14.4 mL) were added to a mixture of 4-bromo-2-(trifluoromethyl)phenol (15 g) and N-methyl pyrrolidone (100 mL) at room temperature, and the mixture was stirred at 90° C. for 3 hours. After the reaction mixture was cooled to room temperature, water was added thereto, then extraction thereof was performed using EtOAc, and the extract was washed with water. The organic layer was dried over $MgSO_4$ and filtered, and the filtrate was concentrated under reduced pressure. The residue was purified by silica gel column chromatography (Hex:EtOAc=9:1 to 6:1), whereby 4-bromo-1-[(4-methoxybenzyl)oxy]-2-(trifluoromethyl)benzene (22 g) was obtained as a colorless oil.

Preparation Example 5

Zinc (64 mg), 2-(di-tert-butylphosphino)biphenyl (163 mg), zinc cyanide (230 mg), and palladium (II) trifluoroacetate (81 mg) were added to a DMAc (16.5 mL) solution of 2-chloro-6-{4-[(4-methoxybenzyl)oxy]-3-(trifluoromethyl)phenyl}-9-methyl-9H-purine (1.1 g) at room temperature in an argon atmosphere, and the mixture was stirred at 100° C. for 3 hours. After the reaction mixture was cooled to room temperature, water was added thereto, then extraction thereof was performed using EtOAc, and the extract was washed with water. The organic layer was dried over $MgSO_4$ and filtered, and the filtrate was concentrated under reduced pressure. The residue was purified by silica gel column chromatography (Hex:EtOAc=1:1 to 1:4), whereby a mixture of 6-{4-[(4-methoxybenzyl)oxy]-3-(trifluoromethyl)phenyl}-9-methyl-9H-purine-2-carbonitrile and 6-[4-hydroxy-3-(trifluoromethyl)phenyl]-9-methyl-9H-purine-2-carbonitrile (502 mg) was obtained.

A mixture of the above mixture (501 mg), trifluoroacetic acid (3.5 mL), and anisole (0.62 mL) was stirred at room temperature for 2 hours. After the reaction mixture was concentrated under reduced pressure, the residue was purified by silica gel column chromatography (Hex:EtOAc=1:2 to 1:6), whereby 6-[4-hydroxy-3-(trifluoromethyl)phenyl]-9-methyl-9H-purine-2-carbonitrile (243 mg) was obtained as a white solid.

Preparation Example 6 tert-Butyl 4-(2-{[(4-methylphenyl)sulfonyl]oxy}ethyl)piperidine-1-carboxylate (2.65 g) and potassium carbonate (2.0 g) were added to a mixture of 4-bromo-2-(trifluoromethyl)benzenethiol (1.8 g) and DMF (20 mL) at room temperature, and the mixture was stirred at the same temperature overnight. The reaction mixture was further stirred at 80° C. for 3 hours. After the reaction mixture was cooled to room temperature, water (50 mL) and EtOAc (30 mL) were added thereto, then extraction thereof was performed using EtOAc, and the extract was washed with saturated brine. The organic layer was dried over $MgSO_4$ and filtered, and the filtrate was concentrated under reduced pressure. The residue was purified by silica gel column chromatography (Hex: EtOAc=100:0 to 80:20), whereby tert-butyl 4-(2-{[4-bromo-2-(trifluoromethyl)phenyl]sulfanyl}ethyl)piperidine-1-carboxylate (2.83 g) was obtained as a colorless oil.

Preparation Example 7 tert-Butyl 4-(2-hydroxyethyl)piperidine-1-carboxylate (4.8 g) and triphenylphosphine (5.7 g) were added to a solution of 4-bromo-2-(trifluoromethyl)phenol (5 g) in THF (50 mL) at room temperature. Under ice-cooling, bis(2-methoxyethyl) azodicarboxylate (5.1 g) was added to the mixture at an internal temperature of 10° C. or lower. The mixture was stirred at room temperature for 6 hours. After the reaction mixture was ice-cooled, water (50 mL) was added dropwise thereto, and the mixture was stirred for 1 hour. Extraction was performed on the mixture using EtOAc, and the extract was washed with water. The organic layer was dried over $MgSO_4$ and filtered, and the filtrate was concentrated under reduced pressure. After Hex was added to the residue, the mixture was stirred, and the insoluble material was separated by filtration. The filtrate was concentrated under reduced pressure, and the residue was purified by basic silica gel column chromatography (Hex:EtOAc=9:1 to 6:1), whereby tert-butyl 4-(2-{[4-bromo-2-(trifluoromethyl)phenoxy]ethyl}piperidine-1-carboxylate (7.46 g) was obtained as a colorless oil.

Preparation Example 8

Palladium (II) acetate (62 mg) was added to a mixture of 1-bromo-2-(methoxymethoxy)benzene (1.2 g), 2-dicyclohexylphosphino-2',6'-dimethoxybiphenyl (227 mg), and THF (24 mL) in a nitrogen atmosphere. After the mixture was ice-cooled, a 0.5 M solution of cyclobutyl zinc bromide in THF (22.1 mL) was added dropwise thereto, and the mixture was stirred at room temperature overnight. After the reaction mixture was concentrated under reduced pressure, EtOAc was added to the residue. A saturated aqueous $NaHCO_3$ solution was added to the mixture, followed by stirring, and the insoluble material was separated by filtration using Celite. Extraction was performed on the filtrate using EtOAc, and the extract was washed with saturated brine. The organic layer was dried over $Na_2SO_4$ and filtered, and the filtrate was concentrated under reduced pressure. The residue was purified by silica gel column chromatography (Hex:EtOAc=10:0 to 9:1), whereby 1-cyclobutyl-2-(methoxymethoxy)benzene (713 mg) was obtained as a colorless oil.

Preparation Example 9

10% palladium on carbon (about 50% wet) (170 mg) was added to a mixture of tert-butyl 3-(2-ethoxy-2-oxoethylidene)-8-azabicyclo[3.2.1]octane-8-carboxylate (1.7 g) and EtOH (34 mL), and the mixture was stirred at room temperature for 4 hours in a hydrogen atmosphere at 3 atm. The reaction mixture was separated by filtration using Celite, and the filtrate was concentrated under reduced pressure, whereby tert-butyl 3-(2-ethoxy-2-oxoethyl)-8-azabicyclo[3.2.1]octane-8-carboxylate (1.7 g) was obtained as a colorless oil.

Preparation Example 10

60% sodium hydride (109 mg) was added to a mixture of triethyl phosphonoacetate (1.02 g) and THF (12 mL) at 0° C. in a nitrogen atmosphere, and the mixture was stirred at room temperature for 10 minutes. 3-Benzyl-3-azabicyclo[3.2.1]octan-8-one (978 mg) and DMF (5 mL) were added to the mixture, and the mixture was stirred at room temperature overnight. After water was added to the reaction mixture, extraction thereof was performed using EtOAc, and the extract was washed with saturated brine. The organic layer was dried over $MgSO_4$ and filtered, and the filtrate was concentrated under reduced pressure. The residue was purified by silica gel column chromatography (Hex:EtOAc=97:3 to 80:20), whereby ethyl(3-benzyl-3-azabicyclo[3.2.1]oct-8-ylidene)acetate (362 mg) was obtained as a colorless liquid.

Preparation Example 11

After a solution of tert-butyl 3-(2-ethoxy-2-oxoethyl)-8-azabicyclo[3.2.1]octane-8-carboxylate (1.7 g) in THF (10 mL) was cooled to −78° C. in an argon atmosphere, a 1.02 M solution of diisobutylaluminium hydride in toluene (17.5 mL) was added dropwise thereto, then, the mixture was stirred at the same temperature for 1 hour, and further stirred at 0° C. for 30 minutes. An aqueous Rochelle salt solution and EtOAc were added the reaction mixture, followed by stirring for 1 hour. After the temperature of the reaction mixture was raised to room temperature, extraction thereof was performed using EtOAc, and the extract was washed with saturated brine. The organic layer was dried over $MgSO_4$ and filtered, and the filtrate was concentrated under reduced pressure. The residue was purified by silica gel column chromatography (Hex: EtOAc=97:3 to 80:20), whereby tert-butyl 3-(2-hydroxyethyl)-8-azabicyclo[3.2.1]octane-8-carboxylate (0.83 g) was obtained as a colorless oil.

Preparation Example 12

After concentrated hydrochloric acid (3.1 mL) was added to a solution of 1-cyclobutyl-2-(methoxymethoxy)benzene (1.43 g) in MeOH (29 mL) at room temperature, the mixture was stirred at 60° C. for 2 hours. After the reaction mixture was cooled to room temperature, a standard buffer solution of pH 6.86 was added thereto, and EtOAc was added. Extraction was performed on the mixture using EtOAc, and the extract was washed with saturated brine. The organic layer was dried over $Na_2SO_4$ and filtered, and the filtrate was concentrated under reduced pressure, whereby 2-cyclobutylphenol (1.1 g) was obtained as a colorless oil.

Preparation Example 13

Tetra-n-butylammonium tribromide (4.72 g) was added to a solution of 2-cyclobutylphenol (1.21 g) in $CH_2Cl_2$ (24.2 mL) at room temperature, and the mixture was stirred at the same temperature overnight. After the reaction mixture was pour into a saturated aqueous sodium sulfite solution, extraction was performed on the mixture using EtOAc, and the extract was washed with water and saturated brine. The organic layer was dried over $Na_2SO_4$ and filtered, and the filtrate was concentrated under reduced pressure. The residue was purified by silica gel column chromatography (Hex:

EtOAc=100:0 to 84:16), whereby 4-bromo-2-cyclobutylphenol (1.85 g) was obtained as a colorless oil.

Preparation Example 14

Di-tert-butyl dicarbonate (300 mg) and 20% palladium hydroxide on carbon (about 50% wet) were added to a mixture of ethyl(3-benzyl-3-azabicyclo[3.2.1]oct-8-ylidene)acetate (350 mg) and EtOH (10 mL) in a nitrogen atmosphere, and the mixture was stirred at room temperature for 16 hours in a hydrogen atmosphere at 4 atm. The reaction mixture was separated by filtration using Celite, and the filtrate was concentrated under reduced pressure. The residue was purified by silica gel column chromatography (Hex:EtOAc=97:3 to 85:15), whereby tert-butyl 8-(2-ethoxy-2-oxoethyl)-3-azabicyclo[3.2.1]octane-3-carboxylate (371 mg) was obtained as a colorless liquid.

Preparation Example 15

Triethylamine (0.27 mL) and p-toluenesulfonyl chloride (269 mg) were added to a mixture of tert-butyl 3-(2-hydroxyethyl)-8-azabicyclo[3.2.1]octane-8-carboxylate (300 mg) and $CH_2Cl_2$ (6 mL) at room temperature, and the mixture was stirred at the same temperature overnight. After $CHCl_3$ and water were added to the reaction mixture, extraction thereof was performed using $CHCl_3$, and the extract was washed with water. The organic layer was dried over $MgSO_4$ and filtered, and the filtrate was concentrated under reduced pressure. The residue was purified by silica gel column chromatography (Hex:EtOAc=95:5 to 70:30), whereby tert-butyl 3-(2-{[(4-methylphenyl)sulfonyl]oxy}ethyl)-8-azabicyclo[3.2.1]octane-8-carboxylate (375 mg) was obtained as a light brown oil.

Preparation Example 16 tert-Butyl 3-(2-{[(4-methylphenyl)sulfonyl]oxy}ethyl)-8-azabicyclo[3.2.1]octane-8-carboxylate (150 mg) and potassium carbonate (100 mg) were added to a solution of 4-[4-hydroxy-3-(trifluoromethyl)phenyl]-7-methyl-7H-pyrrolo[2,3-d]pyrimidine-2-carbonitrile (100 mg) in DMAc (2 mL) at room temperature, and the mixture was stirred at 80° C. for 1 hour. After the reaction mixture was cooled to room temperature, extraction thereof was performed using EtOAc, and the extract was washed with water and saturated brine. The organic layer was dried over $MgSO_4$ and filtered, and the filtrate was concentrated under reduced pressure. The residue was purified by silica gel column chromatography (Hex:EtOAc=80:20 to 50:50), whereby tert-butyl 3-{2-[4-(2-cyano-7-methyl-7H-pyrrolo[2,3-d]pyrimidin-4-yl)-2-(trifluoromethyl)phenoxy]ethyl}-8-azabicyclo[3.2.1]octane-8-carboxylate (146 mg) was obtained as a white solid.

Preparation Example 17

A 2 M solution of methylamine and triethylamine (1.8 mL) in THF (4.6 mL) were added to a solution of 2,4,6-trichloro-5-nitropyrimidine (2 g) in THF (30 mL) under ice-cooling, and the mixture was stirred for 1 hour under ice-cooling. After water was added to the reaction mixture, extraction thereof was performed using EtOAc, and the extract was washed with water and saturated brine. The organic layer was dried over $MgSO_4$ and filtered, and the filtrate was concentrated under reduced pressure. The residue was purified by silica gel column chromatography (Hex:EtOAc=99:1 to 90:10), whereby 2,6-dichloro-N-methyl-5-nitropyrimidine-4-amine (680 mg) was obtained as a pale yellow solid.

Preparation Example 18

Tin (II) chloride dihydrate (2.0 g) was added to a solution of 2,6-dichloro-N-methyl-5-nitropyrimidine-4-amine (680 mg) in EtOH (13 mL) at room temperature. The mixture was stirred at room temperature for 3 hours, and stirred at 90° C. for 2 hours. The reaction mixture was cooled to room temperature, and concentrated under reduced pressure. EtOAc and a saturated aqueous $NaHCO_3$ solution were added to the residue, and the insoluble material was separated by filtration using Celite. Extraction was performed on the filtrate using EtOAc, and the extract was washed with water and saturated brine. The organic layer was dried over $MgSO_4$ and filtered, and the filtrate was concentrated under reduced pressure. The residue was purified by silica gel column chromatography (Hex:EtOAc=80:20 to 50:50), whereby 2,6-dichloro-$N^4$-methylpyrimidine-4,5-diamine (482 mg) was obtained as a pale yellow solid.

Preparation Example 19

Potassium carbonate (442 mg) and methyl iodide (0.17 mL) were added to a solution of 2,6-dichloro-8-methyl-7H-purine (500 mg) in THF (5 mL) under ice-cooling, and the mixture was stirred at room temperature for 5 hours. After the reaction mixture was ice-cooled, water was added thereto, extraction thereof was performed using EtOAc, and the extract was washed with water and saturated brine. The organic layer was dried over $MgSO_4$ and filtered, and the filtrate was concentrated under reduced pressure. The residue was purified by silica gel column chromatography (Hex:EtOAc=9:1 to 8:2), whereby 2,6-dichloro-8,9-dimethyl-9H-purine (310 mg) was obtained as a white solid.

Preparation Example 20

Tetrahydrofuran-3-ylmethanol (8 mL) and tributylphosphine (22 mL) were added to a suspension of 2,4-dichloro-7H-pyrrolo[2,3-d]pyrimidine (10 g) in $CH_2Cl_2$ (150 mL) at room temperature. 1,1'-(azodicarbonyl)dipiperidine (22 g) was added thereto under ice-cooling, and the mixture was stirred at room temperature overnight. After Hex (300 mL) was added to the reaction mixture, the mixture was stirred, and the insoluble material was separated by filtration. The filtrate was concentrated under reduced pressure, and the residue was purified by silica gel column chromatography (Hex:EtOAc=9:1 to 6:4), whereby 2,4-dichloro-7-(tetrahydrofuran-3-ylmethyl)-7H-pyrrolo[2,3-d]pyrimidine (5.9 g) was obtained as a dark brown oil.

Preparation Example 21

1-(tert-Butoxycarbonyl)-4-piperidinemethanol (400 mg) was added to a mixture of 60% sodium hydride (90 mg) and DMF (11 mL) under ice-cooling in a nitrogen atmosphere, and the mixture was stirred for 10 minutes. A solution of 4-bromo-1-(bromomethyl)-2-(trifluoromethyl)benzene (550 mg) in DMF (2 mL) was added to the mixture under ice-cooling. After the reaction mixture was stirred for 30 minutes under ice-cooling, the temperature of the reaction mixture was raised to room temperature, and stirring was performed for 30 minutes. After a saturated aqueous ammonium chloride solution was added to the reaction mixture, extraction thereof was performed using an EtOAc-Hex mixed solvent (1:1), and the extract was washed with water and saturated brine. The organic layer was dried over MgSO$_4$ and filtered, and the filtrate was concentrated under reduced pressure. The residue was purified by silica gel column chromatography (Hex:EtOAc=99:1 to 90:10), whereby tert-butyl 4-({[4-bromo-2-(trifluoromethyl)benzyl]oxy}methyl)piperidine-1-carboxylate (598 mg) was obtained as a pale yellow oil.

Preparation Example 22

A mixture of 2,6-dichloro-N$^4$-methylpyrimidine-4,5-diamine (400 mg) and trifluoroacetic acid (8 mL) was stirred for 8 hours while heating to reflux. Furthermore, the reaction mixture was stirred at 120° C. for 1.5 hours under microwave irradiation. After the reaction mixture was concentrated under reduced pressure, phenylphosphonic dichloride (1.8 mL) was added to the residue, and the mixture was stirred 180° C. for 2 hours. After the reaction mixture was cooled to room temperature, cold water (20 mL) was added thereto, then, the mixture was stirred, and the precipitate was collected by filtration. The obtained solid was purified by silica gel column chromatography (Hex:EtOAc=100:0 to 90:10), whereby 2,6-dichloro-9-methyl-8-(trifluoromethyl)-9H-purine (435 mg) was obtained as a white solid.

Preparation Example 23

After tert-butyl 4-{2-[4-(4,4,5,5-tetramethyl-1,3,2-dioxaborolan-2-yl)-2-(trifluoromethyl)phenoxy]ethyl}piperidine-1-carboxylate (266 mg), Na$_2$CO$_3$ (169 mg), and tetrakis(triphenylphosphine)palladium (0) (31 mg) were added to a mixture of 2,4-dichloro-7H-pyrrolo[2,3-d]pyrimidine (100 mg), dioxane (1.6 mL), and water (0.6 mL), the mixture was stirred at 150° C. for 2 hours under microwave irradiation, and cooled to room temperature. After water and EtOAc were added to the reaction mixture, the mixture was stirred, filtered, and washed with EtOAc, whereby tert-butyl 4-{2-[4-(2-chloro-7H-pyrrolo[2,3-d]pyrimidin-4-yl)-2-(trifluoromethyl)phenoxy]ethyl}piperidine-1-carboxylate (121 mg) was obtained as a brown solid.

Preparation Example 24

A 4 M solution of hydrogen chloride in EtOAc (5 mL) was added to a suspension of tert-butyl 4-(2-{4-[2-chloro-7-(2-methoxyethyl)-7H-pyrrolo[2,3-d]pyrimidin-4-yl]-2-(trifluoromethyl)phenoxy}ethyl)piperidine-1-carboxylate (500 mg) in EtOAc (5 mL), and the mixture was stirred at the same temperature for 1 hour. The reaction mixture was concentrated under reduced pressure, whereby 2-chloro-7-(2-methoxyethyl)-4-{4-[2-(piperidin-4-yl)ethoxy]-3-(trifluoromethyl)phenyl}-7H-pyrrolo[2,3-d]pyrimidine monohydrochloride (445 mg) was obtained as a pale yellow solid.

Preparation Example 25

Tris(dimethylamino)sulfonium difluorotrimethylsilicate (239 mg) was added to a mixture of 4-[4-fluoro-3-(trifluoromethyl)phenyl]-7-[(4-methylphenyl)sulfonyl]-7H-pyrrolo[2,3-d]pyrimidine-2-carbonitrile (200 mg) and DMAc (3 mL), and the mixture was stirred at 100° C. for 1 hour under microwave irradiation. After the reaction mixture was cooled to room temperature, the reaction mixture was purified by silica gel column chromatography (Hex:EtOAc=98:2 to 60:40), whereby 4-[4-fluoro-3-(trifluoromethyl)phenyl]-7H-pyrrolo[2,3-d]pyrimidine-2-carbonitrile (81 mg) was obtained as a pale yellow solid.

Preparation Example 26

Triethylamine (0.35 mL) was added to a suspension of 2-chloro-7-(2-methoxyethyl)-4-{4-[2-(piperidin-4-yl)ethoxy]-3-(trifluoromethyl)phenyl}-7H-pyrrolo[2,3-d]pyrimidine monohydrochloride (440 mg) in dichloroethane (8 mL) at room temperature, and the mixture was stirred at the same temperature for 15 minutes. After the reaction mixture was ice-cooled, acetic acid (0.24 mL), sodium triacetoxyborohydride (359 mg), and acetaldehyde (0.14 mL) were added thereto, and the mixture was stirred for 1 hour under ice-cooling. After a saturated aqueous NaHCO$_3$ solution was added to the reaction mixture, extraction thereof was performed using CHCl$_3$, and the extract was washed with water and saturated brine. The organic layer was dried over MgSO$_4$ and filtered, and the filtrate was concentrated under reduced pressure. The residue was purified by basic silica gel column chromatography (CHCl$_3$), whereby 2-chloro-4-{4-[2-(1-ethylpiperidin-4-yl)ethoxy]-3-(trifluoromethyl)phenyl}-7-(2-methoxyethyl)-7H-pyrrolo[2,3-d]pyrimidine (431 mg) was obtained as a colorless oil.

Preparation Example 27

Bis(pinacolato)diboron (17.2 g), potassium acetate (13.3 g), and dichlorobis(triphenylphosphine)palladium (II) (1.9 g) were added to a solution of tert-butyl 4-{2-[4-bromo-2-(trifluoromethyl)phenoxy]ethyl}piperidine-1-carboxylate (20.4 g) in dioxane (204 mL) at room temperature in an argon atmosphere, and the mixture was stirred at 100° C. for 4 hours. After the reaction mixture was cooled to room temperature, extraction thereof was performed using EtOAc, and the extract was washed with water. The organic layer was dried over MgSO$_4$ and filtered, and the filtrate was concentrated under reduced pressure. The residue was purified by silica gel column chromatography (Hex:EtOAc=6:1 to 4:1), whereby tert-butyl 4-{2-[4-(4,4,5,5-tetramethyl-1,3,2-dioxaborolan-2-yl)-2-(trifluoromethyl)phenoxy]ethyl}piperidine-1-carboxylate (22.0 g) was obtained as a colorless oil.

Preparation Example 28 tert-Butyl 4-(2-hydroxyethyl)piperidine-1-carboxylate (7.7 g) and 1,1'-(azodicarbonyl)dipiperidine (11.6 g) were added to a mixture of 5-bromo-3-(trifluoromethyl)pyridine-2-ol (7 g) and toluene (124 mL) at room temperature. Tributylphosphine (11.6 mL) was added thereto under ice-cooling, and the mixture was stirred at room temperature overnight. After diisopropylether was added to the reaction mixture, the mixture was stirred, and the insoluble material was separated by filtration. The filtrate was concentrated under reduced pressure, and the residue was purified by silica gel column chromatography (Hex:EtOAc=100:0 to 70:30), whereby tert-butyl 4-(2-{[5-bromo-3-(trifluoromethyl)pyridin-2-yl]oxy}ethyl)piperidine-1-carboxylate (8.93 g) was obtained as a colorless oil.

Preparation Example 29

Sodium cyanoborohydride (2.2 g) was added to a mixture of ethyl 4-piperidine acetate (2.0 g), (1-ethoxycyclopropoxy)trimethylsilane (6.1 g), acetic acid (6.7 mL), a molecular sieve 3A (2.0 g), MeOH (20 mL), and THF (20 mL) at room temperature, and the mixture was stirred at 65° C. for 6 hours. The reaction mixture was cooled to room temperature, and concentrated under reduced pressure. After EtOAc was added to the residue, the mixture was stirred, and the insoluble material was separated by filtration. After water was added to the filtrate, potassium carbonate was added to alkalify the mixture. Extraction was performed on the mixture using EtOAc, and the extract was washed with a saturated aqueous NaHCO$_3$ solution and saturated brine. The organic layer was dried over Na$_2$SO$_4$ and filtered, and the filtrate was concentrated under reduced pressure. The residue was purified by silica gel column chromatography (CHCl$_3$:MeOH=100:0 to 95:5), whereby ethyl(1-cyclopropylpiperidin-4-yl)acetate (2.1 g) was obtained as a colorless oil.

Preparation Example 30

Lithium tetrahydroborate (730 mg) was added to a solution of ethyl(1-cyclopropylpiperidin-4-yl)acetate (2.1 g) in THF (53 mL) under ice-cooling. MeOH (2.4 mL) was added thereto, and the mixture was stirred at room temperature overnight. After water and EtOAc were added to the reaction mixture, the mixture was stirred for 30 minutes, and extraction was performed using EtOAc. The organic layer was dried over Na$_2$SO$_4$ and filtered, and the filtrate was concentrated under reduced pressure. The residue was purified by basic silica gel column chromatography (Hex:EtOAc=80:20 to 60:40), whereby 2-(1-cyclopropylpiperidin-4-yl)ethanol (1.3 g) was obtained as a pale yellow oil.

Preparation Example 31

Chloroacetyl chloride (0.43 mL) was added to a mixture of a solution of 4-cyanopiperidine (500 mg) in CH$_2$Cl$_2$ (5 mL) and an aqueous 2 M Na$_2$CO$_3$ solution (5.7 mL) under ice-cooling, and the mixture was stirred for 30 minutes under ice-cooling. After the reaction mixture was further stirred at room temperature for 4 hours, CH$_2$Cl$_2$ and water were added thereto, then, extraction was performed on the mixture using CH$_2$Cl$_2$, and the extract was washed with saturated brine. The organic layer was dried over Na$_2$SO$_4$ and filtered, and the filtrate was concentrated under reduced pressure, whereby 1-(chloroacetyl)piperidine-4-carbonitrile (845 mg) was obtained as a light yellow oil.

Preparation Example 32

Cyanomethylenetributylphosphorane (1.1 mL) was added to a mixture of tert-butyl 4-{2-[4-(2-chloro-7H-pyrrolo[2,3-d]pyrimidin-4-yl)-2-(trifluoromethyl)phenoxy]ethyl}piperidine-1-carboxylate (1.0 g), tetrahydro-2H-pyran-4-ol (0.36 mL), and toluene (30 mL) at room temperature in a nitrogen atmosphere, and the reaction mixture was stirred overnight while heating to reflux. The reaction mixture was cooled to room temperature, and concentrated under reduced pressure. The residue was purified by silica gel column chromatography (Hex:EtOAc=67:33 to 33:67), whereby tert-butyl 4-(2-{4-[2-chloro-7-(tetrahydro-2H-pyran-4-yl)-7H-pyrrolo[2,3-d]pyrimidin-4-yl]-2-(trifluoromethyl)phenoxy}ethyl)piperidine-1-carboxylate (1.04 g) was obtained as a yellow amorphous material.

Preparation Example 33

Bis(pinacolato)diboron (4.12 g), potassium acetate (4.35 g), and dichlorobis(triphenylphosphine)palladium (II) (1.04 g) were added to a solution of 4-bromo-1-[(4-methoxybenzyl)oxy]-2-(trifluoromethyl)benzene (5.87 g) in dioxane (90 mL) at room temperature in an argon atmosphere, and the mixture was stirred at 100° C. for 2 hours. After the reaction mixture was cooled to room temperature, 2,6-dichloro-9-methyl-9H-purine (3 g), Na$_2$CO$_3$ (4.7 g), tetrakis(triphenylphosphine)palladium (0) (854 mg), and water (15 mL) were added thereto. The reaction mixture was stirred at 100° C. for 4 hours. After the reaction mixture was cooled to room temperature, EtOAc was added thereto, followed by stirring, and the insoluble material was separated by filtration using Celite. Extraction was performed on the filtrate using EtOAc, and the extract was washed with water. The organic layer was dried over MgSO$_4$ and filtered, and the filtrate was concentrated under reduced pressure. The residue was purified by silica gel column chromatography (Hex:EtOAc=4:1 to 1:1), whereby 2-chloro-6-{4-[(4-methoxybenzyl)oxy]-3-(trifluoromethyl)phenyl}-9-methyl-9H-purine (1.1 g) was obtained as a white solid.

Preparation Example 34

Acetic acid (0.1 mL) and a 1.0 M solution of tetrabutylammonium fluoride in THF (1 mL) were added to a solution of tert-butyl 4-(2-{4-[7-(2-{[tert-butyl(dimethyl)silyl]oxy}ethyl)-2-cyano-7H-pyrrolo[2,3-d]pyrimidin-4-yl]-2-(trifluoromethyl)phenoxy}ethyl)piperidine-1-carboxylate (390 mg) in THF (5 mL) at room temperature, and the mixture was stirred at the same temperature for 7 hours. After a saturated aqueous NaHCO$_3$ solution was added to the reaction mixture, extraction thereof was performed using EtOAc, and the extract was washed with water and saturated brine. The organic layer was dried over MgSO$_4$ and filtered, and the filtrate was concentrated under reduced pressure. The residue was purified by silica gel column chromatography (Hex:EtOAc=70:30 to 40:60), whereby tert-butyl 4-(2-{4-[2-cyano-7-(2-hydroxyethyl)-7H-pyrrolo[2,3-d]pyrimidin-4-yl]-2-(trifluoromethyl)phenoxy}ethyl)piperidine-1-carboxylate (323 mg) was obtained as a colorless oil.

Preparation Example 48

2,6-Dichloro-9-methyl-9H-purine (5.6 g), Na$_2$CO$_3$ (11.7 g), water (16.8 mL), and tetrakis(triphenylphosphine)palladium (0) (1.6 g) were added to a solution of tert-butyl 4-(2-{[5-(4,4,5,5-tetramethyl-1,3,2-dioxaborolan-2-yl)-3-(trifluoromethyl)pyridin-2-yl]oxy}ethyl)piperidine-1-carboxylate (13.8 g) in dioxane (112 mL) at room temperature in an argon atmosphere, and the mixture was stirred at an internal temperature of 85° C. for 5 hours. After the reaction mixture was cooled to room temperature, water (700 mL) was added thereto, and the mixture was stirred for 3 hours. The precipitate was collected by filtration, then, washed with water and diisopropyl ether, and dried. The obtained solid was purified by silica gel column chromatography (Hex:EtOAc:CHCl$_3$=1:1:1), whereby tert-butyl 4-(2-{[5-(2-chloro-9-methyl-9H-purin-6-yl)-3-(trifluoromethyl)pyridin-2-yl]oxy}ethyl)piperidine-1-carboxylate (9.5 g) was obtained as a solid.

As a different method, the compound was obtained from a reaction of tert-butyl 4-(2-{[5-bromo-3-(trifluoromethyl)pyridin-2-yl]oxy}ethyl)piperidine-1-carboxylate and 2,6-dichloro-9-methyl-9H-purine by the same method as in Preparation Example 33.

Preparation Example 110

Bis(pinacolato)diboron (11.5 g), potassium acetate (9.6 g), and dichlorobis(triphenylphosphine)palladium (II) (1.1 g)

were added to a solution of tert-butyl 4-(2-{[5-bromo-3-(trifluoromethyl)pyridin-2-yl]oxy}ethyl)piperidine-1-carboxylate (14.7 g) in dioxane (294 mL) at room temperature in an argon atmosphere, and the mixture was stirred at 110° C. for 2 hours. After the reaction mixture was cooled to room temperature, EtOAc (200 mL) was added thereto, followed by stirring. Then, the insoluble material was separated by filtration, and the filtrate was concentrated under reduced pressure. The residue was purified by silica gel column chromatography (Hex:EtOAc=98:2 to 90:10), whereby tert-butyl 4-(2-{[5-(4,4,5,5-tetramethyl-1,3,2-dioxaborolan-2-yl)-3-(trifluoromethyl)pyridin-2-yl]oxy}ethyl)piperidine-1-carboxylate (14.0 g) was obtained as an oil.

Preparation Example 133

Zinc (498 mg), 2-di-tert-butylphosphino-2',4',6'-triisopropylbiphenyl (1.3 g), zinc cyanide (1.8 g), and palladium (II) trifluoroacetate (498 mg) were added to a solution of tert-butyl 4-(2-{[5-(2-chloro-9-methyl-9H-purin-6-yl)-3-(trifluoromethyl)pyridin-2-yl]oxy}ethyl)piperidine-1-carboxylate (8.3 g) in DMAc (125 mL) at room temperature in an argon atmosphere, and the mixture was stirred at 50° C. for 3 hours. After the reaction mixture was cooled to room temperature, EtOAc (100 mL) and Celite were added thereto, and the mixture was stirred at room temperature. The insoluble material was separated by filtration, and a saturated aqueous NaHCO$_3$ solution, saturated brine, and water was added to the filtrate. Extraction was performed on the mixture using EtOAc, and the extract was washed with water and saturated brine. The organic layer was dried over MgSO$_4$ and filtered, and the filtrate was concentrated under reduced pressure. The residue was purified by silica gel column chromatography (Hex:EtOAc=70:30 to 30:70), whereby tert-butyl 4-(2-{[5-(2-cyano-9-methyl-9H-purin-6-yl)-3-(trifluoromethyl)pyridin-2-yl]oxy}ethyl)piperidine-1-carboxylate (7.6 g) was obtained as a solid.

Preparation Example 137

A solution of tert-butyl(3R)-3-hydroxypyrrolidine-1-carboxylate (7.0 g) in THF (30 mL) was added to a suspension of 60% sodium hydroxide (2.3 g) in THF (40 mL) under ice-cooling. At the same temperature, a THF (30 mL) solution of ethyl bromoacetate (13 mL) was added to the mixture, and the mixture was stirred overnight. After water and EtOAc were added to the reaction mixture, extraction thereof was performed using EtOAc, and the extract was washed with saturated brine. The organic layer was dried over MgSO$_4$ and filtered, and the filtrate was concentrated under reduced pressure. The residue was purified by silica gel column chromatography (Hex:EtOAc=99:1 to 70:30), whereby tert-butyl (3R)-3-(2-ethoxy-2-oxoethoxy)pyrrolidine-1-carboxylate (6.6 g) was obtained as an oil.

Preparation Example 138

O-(7-azabenzotriazol-1-yl)-N,N,N',N'-tetramethyluronium hexafluorophosphate (546 mg) was added to a solution of 1-(tert-butoxycarbonyl)piperidine-4-carboxylic acid (329 mg) in DMF (10 mL) at room temperature, and the mixture was stirred at the same temperature for 15 minutes. 7-Methyl-4-[6-(piperidin-4-yl methoxy)-5-(trifluoromethyl)pyridin-3-yl]-7H-pyrrolo[2,3-d]pyrimidine-2-carbonitrile monohydrochloride (500 mg) and N,N-diisopropylethylamine (0.38 mL) were added to the reaction mixture at room temperature, and the mixture was stirred at the same temperature overnight. After EtOAc and a saturated aqueous NaHCO$_3$ solution were added to the reaction mixture, extraction thereof was performed using EtOAc, and the extract was washed with water and saturated brine. The organic layer was dried over MgSO$_4$ and filtered, and the filtrate was concentrated under reduced pressure. The residue was purified by silica gel column chromatography (CHCl$_3$:MeOH=100:0 to 96:4), whereby tert-butyl 4-{[4-({[5-(2-cyano-7-methyl-7H-pyrrolo[2,3-d]pyrimidin-4-yl)-3-(trifluoromethyl)pyridin-2-yl]oxy}methyl)piperidin-1-yl]carbonyl}piperidine-1-carboxylate (488 mg) was obtained as a solid.

Preparation Example 139

Trifluoroacetic acid (2 mL) was added to a solution of tert-butyl(3R)-3-(2-{[5-(2-cyano-7-methyl-7H-pyrrolo[2,3-d]pyrimidin-4-yl)-3-(trifluoromethyl)pyridin-2-yl]oxy}ethoxy)pyrrolidine-1-carboxylate (240 mg) in CH$_2$Cl$_2$ (4 mL)-acetonitrile (1 mL) at room temperature, and the mixture was stirred at the same temperature for 1 hour. After the reaction mixture was concentrated under reduced pressure, CH$_2$Cl$_2$ (4 mL) and a 4 M solution of hydrogen chloride in EtOAc (0.4 mL) were added to the residue at room temperature. The reaction mixture was concentrated under reduced pressure, and diisopropyl ether was added to the residue. The precipitate was collected by filtration, whereby 7-methyl-4-[6-{2-[(3R)-pyrrolidin-3-yloxy]ethoxy}-5-(trifluoromethyl)pyridin-3-yl]-7H-pyrrolo[2,3-d]pyrimidine-2-carbonitrile monohydrochloride (208 mg) was obtained as a solid.

In the same manner as in Preparation Examples described above, compounds of Preparation Examples shown in the following tables were prepared. Structures, preparing methods, and physicochemical data of respective Preparation Example compounds are shown in Tables 3 to 24, respectively.

Example 1

Zinc (11 mg), 2-(di-tert-butylphosphino)biphenyl (23 mg), zinc cyanide (25 mg), and palladium (II) trifluoroacetate (12 mg) were added to a solution of 2-chloro-4-[4-ethoxy-3-(trifluoromethyl)phenyl]-7-methyl-7H-pyrrolo[2,3-d]pyrimidine (125 mg) in DMAc (2.5 mL) at room temperature in an argon atmosphere, and the mixture was stirred at 110° C. for 5 hours. After the reaction mixture was cooled to room temperature, EtOAc was added thereto, followed by stirring, and the insoluble material was separated by filtration using Celite. Extraction was performed on the filtrate using EtOAc, and the extract was washed with a saturated aqueous NaHCO$_3$ solution, water and saturated brine. The organic layer was dried over MgSO$_4$ and filtered, and the filtrate was concentrated under reduced pressure. The residue was purified by silica gel column chromatography (Hex:EtOAc=9:1 to 1:1), whereby 4-[4-ethoxy-3-(trifluoromethyl)phenyl]-7-methyl-7H-pyrrolo[2,3-d]pyrimidine-2-carbonitrile (52.9 mg) was obtained as a pale yellow solid.

Example 2

A 4 M solution of hydrogen chloride in EtOAc (2 mL) was added to a solution of tert-butyl 4-{2-[4-(2-cyano-7-methyl-7H-pyrrolo[2,3-d]pyrimidin-4-yl)-2-(trifluoromethyl)phenoxy]ethyl}piperidine-1-carboxylate (232 mg) in EtOAc (2 mL) at room temperature, and the mixture was stirred at the same temperature for 1 hour. The precipitate was collected by filtration, whereby 7-methyl-4-{4-[2-(piperidin-4-yl)

ethoxy]-3-(trifluoromethyl)phenyl}-7H-pyrrolo[2,3-d]pyrimidine-2-carbonitrile monohydrochloride (198 mg) was obtained as a white solid.

Example 3

Potassium carbonate (133 mg), potassium iodide (160 mg), and 2-chloro-N,N-dimethylacetamide (34 µL) were added to a suspension of 7-methyl-4-{4-[2-(piperidin-4-yl)ethoxy]-3-(trifluoromethyl)phenyl}-7H-pyrrolo[2,3-d]pyrimidine-2-carbonitrile monohydrochloride (150 mg) in acetonitrile (6 mL) at room temperature, and the mixture was stirred at 60° C. for 2 hours. After the reaction mixture was cooled to room temperature, water was added thereto, extraction thereof was performed using EtOAc, and the extract was washed with a saturated aqueous ammonium chloride solution, water, and saturated brine. The organic layer was dried over $MgSO_4$ and filtered, and the filtrate was concentrated under reduced pressure. The residue was purified by basic silica gel column chromatography (Hex:EtOAc=1:3). The obtained product was washed with diisopropyl ether, and collected by filtration, whereby 2-(4-{2-[4-(2-cyano-7-methyl-7H-pyrrolo[2,3-d]pyrimidin-4-yl)-2-(trifluoromethyl)phenoxy]ethyl}piperidin-1-yl)-N,N-dimethylacetamide (118 mg) was obtained as a white solid.

Example 4

Trifluoroacetic acid (0.41 mL) was added to a solution of tert-butyl {2-cyano-4-[4-ethoxy-3-(trifluoromethyl)phenyl]-7H-pyrrolo[2,3-d]pyrimidin-7-yl}acetate (160 mg) in $CH_2Cl_2$ (1.6 mL) at room temperature, and the mixture was stirred at the same temperature for 5 hours. After the reaction mixture was concentrated under reduced pressure, the residue was purified by silica gel column chromatography ($CHCl_3$: MeOH=100:0 to 80:20), whereby {2-cyano-4-[4-ethoxy-3-(trifluoromethyl)phenyl]-7H-pyrrolo[2,3-d]pyrimidin-7-yl}acetic acid (137 mg) was obtained as a white solid.

Example 5

1-Methylpiperazine (42 µL), N,N-diisopropylethylamine (66 µL), and (1-cyano-2-ethoxy-2-oxoethylidene aminooxy) dimethylamino-morpholino-carbenium hexafluorophosphate (187 mg) were added to a mixture of {2-cyano-4-[4-ethoxy-3-(trifluoromethyl)phenyl]-7H-pyrrolo[2,3-d]pyrimidin-7-yl}acetic acid (100 mg) and DMF (4 mL) at room temperature, and the mixture was stirred at the same temperature for 2 hours. After water was added to the reaction mixture, the precipitate was collected by filtration, and washed with water. After the obtained solid was dissolved in $CHCl_3$, the solution was concentrated under reduced pressure. The residue was purified by silica gel column chromatography ($CHCl_3$:MeOH=100:0 to 50:50), whereby 4-[4-ethoxy-3-(trifluoromethyl)phenyl]-7-[2-(4-methylpiperazin-1-yl)-2-oxoethyl]-7H-pyrrolo[2,3-d]pyrimidine-2-carbonitrile (82 mg) was obtained as a white solid.

Example 6

A saturated aqueous $NaHCO_3$ and water were added to a suspension of 9-methyl-6-{4-[2-(piperidin-4-yl)ethoxy]-3-(trifluoromethyl)phenyl}-9H-purine-2-carbonitrile monohydrochloride (100 mg) in $CHCl_3$ (20 mL), and the mixture was stirred. Extraction was performed on the mixed solution using $CHCl_3$, and the organic layer was washed with water. The organic layer was dried over $MgSO_4$ and filtered, and the filtrate was concentrated under reduced pressure. After DMF (2 mL) was added to the residue, N-methyl-D-proline (41 mg) and O-(7-azabenzotriazol-1-yl)-N,N,N',N'-tetramethyluronium hexafluorophosphate (122 mg) were added thereto, and the mixture was stirred at room temperature overnight. Extraction was performed on the reaction mixture using EtOAc, and the extract was washed with water and saturated brine. The organic layer was dried over $Na_2SO_4$ and filtered, and the filtrate was concentrated under reduced pressure. The residue was purified by basic silica gel column chromatography (Hex:$CHCl_3$=50:50 to 0:100), whereby 9-methyl-6-[4-{2-[1-(1-methyl-D-prolyl)piperidin-4-yl]ethoxy}-3-(trifluoromethyl)phenyl]-9H-purine-2-carbonitrile (76 mg) was obtained as a white amorphous material.

Example 7

A saturated aqueous $NaHCO_3$ and water were added to a suspension of 9-methyl-6-{4-[2-(piperidin-4-yl)ethoxy]-3-(trifluoromethyl)phenyl}-9H-purine-2-carbonitrile monohydrochloride (100 mg) in $CHCl_3$ (20 mL), and the mixture was stirred. Extraction was performed on the mixed solution using $CHCl_3$, and the organic layer was washed with water. The organic layer was dried over $MgSO_4$ and filtered, and the filtrate was concentrated under reduced pressure. After $CH_2Cl_2$ (3 mL) was added to the residue to suspend the residue, dimethylcarbamoyl chloride (26 µL) and triethylamine (60 µL) were added thereto, and the mixture was stirred overnight at room temperature. Extraction was performed on the reaction mixture using EtOAc, and the extract was washed with water and saturated brine. The organic layer was dried over $Na_2SO_4$ and filtered, and the filtrate was concentrated under reduced pressure. The residue was purified by silica gel column chromatography ($CHCl_3$:MeOH=100:0 to 95:5), whereby 4-{2-[4-(2-cyano-9-methyl-9H-purin-6-yl)-2-(trifluoromethyl)phenoxy]ethyl}-N,N-dimethylpiperidine-1-carboxamide (83 mg) was obtained as a pale yellow solid.

Example 8

1-Methylpiperazine (28 µL), N,N-diisopropylethylamine (43 µL), and O-(7-azabenzotriazol-1-yl)-N,N,N',N'-tetramethyluronium hexafluorophosphate (109 mg) were added to a solution of (2-cyano-4-{4-[2-(tetrahydro-2H-pyran-4-yl)ethoxy]-3-(trifluoromethyl)phenyl}-7H-pyrrolo[2,3-d]pyrimidin-7-yl)acetic acid (80 mg) in DMF (3.2 mL) at room temperature, and the mixture was stirred at the same temperature for 2 hours. After water was added to the reaction mixture, the precipitate was collected by filtration, and washed with water. After the obtained solid was dissolved in $CHCl_3$, the solution was concentrated under reduced pressure. The residue was purified by silica gel column chromatography ($CHCl_3$:MeOH=100:0 to 50:50). After the obtained amorphous material was dissolved in $CH_2Cl_2$ (1 mL), a 4 M solution of hydrogen chloride in EtOAc (84 µL) was added thereto at room temperature. The mixture was concentrated under reduced pressure, and diisopropyl ether was added to the residue. The precipitate was washed with diisopropyl ether and collected by filtration, whereby 7-[2-(4-methylpiperazin-1-yl)-2-oxoethyl]-4-{4-[2-(tetrahydro-2H-pyran-4-yl)ethoxy]-3-(trifluoromethyl)phenyl}-7H-pyrrolo[2,3-d]pyrimidine-2-carbonitrile monohydrochloride (89 mg) was obtained as a white solid.

Example 9

2-(1-Methylpiperidin-4-yl)ethanamine (93 mg) and N,N-diisopropylethylamine (0.22 mL) were added to a mixture of 4-[4-fluoro-3-(trifluoromethyl)phenyl]-7H-pyrrolo[2,3-d]pyrimidine-2-carbonitrile (100 mg) and N-methylpyrrolidone (2 mL), and the mixture was stirred at 140° C. for 1 hour under microwave irradiation. After the reaction mixture was cooled to room temperature, the reaction mixture was purified by silica gel column chromatography (CHCl$_3$:MeOH=98:2 to 85:15), whereby 4-[4-{[2-(1-methylpiperidin-4-yl)ethyl]amino}-3-(trifluoromethyl)phenyl]-7H-pyrrolo[2,3-d]pyrimidine-2-carbonitrile (66 mg) was obtained as a white solid.

Example 10

Trifluoroacetic acid (1 mL) was added to a solution of tert-butyl 4-{2-[4-(2-cyano-8,9-dimethyl-9H-purin-6-yl)-2-(trifluoromethyl)phenoxy]ethyl}piperidine-1-carboxylate (100 mg) in CH$_2$Cl$_2$ (2 mL)-acetonitrile (0.5 mL) at room temperature, and the mixture was stirred at the same temperature for 1 hour. The reaction mixture was concentrated under reduced pressure, and CH$_2$Cl$_2$ (2 mL) was added to the residue. A 4 M solution of hydrogen chloride in EtOAc (0.2 mL) was added to the mixture at room temperature, and the precipitate was collected by filtration, whereby 8,9-dimethyl-6-{4-[2-(piperidin-4-yl)ethoxy]-3-(trifluoromethyl)phenyl}-9H-purine-2-carbonitrile monohydrochloride (59 mg) was obtained as a white solid.

Example 11

Triethylamine (114 μL) was added to a suspension of 8,9-dimethyl-6-{4-[2-(piperidin-4-yl)ethoxy]-3-(trifluoromethyl)phenyl}-9H-purine-2-carbonitrile monohydrochloride (128 mg) in dichloroethane (3 mL) at room temperature, and the mixture was stirred at the same temperature for 15 minutes. After the reaction mixture was ice-cooled, acetic acid (76 μL), sodium triacetoxyborohydride (113 mg), and acetaldehyde (45 μL) were added thereto, and the mixture was stirred for 1 hour under ice-cooling. After a saturated aqueous NaHCO$_3$ solution was added to the reaction mixture, extraction thereof was performed using CHCl$_3$, and the extract was washed with water and saturated brine. The organic layer was dried over MgSO$_4$ and filtered, and the filtrate was concentrated under reduced pressure. The residue was purified by basic silica gel column chromatography (CHCl$_3$). The obtained product was washed with diisopropyl ether, and collected by filtration, whereby 6-{4-[2-(1-ethylpiperidin-4-yl)ethoxy]-3-(trifluoromethyl)phenyl}-8,9-dimethyl-9H-purine-2-carbonitrile (79 mg) was obtained as a pale yellow solid.

Example 12

Triethylamine (90 μL) was added to a solution of 7-methyl-4-{6-[2-(piperidin-3-yl)ethoxy]-5-(trifluoromethyl)pyridin-3-yl}-7H-pyrrolo[2,3-d]pyrimidine-2-carbonitrile monohydrochloride (100 mg) in dichloroethane (2 mL) at room temperature, and the mixture was stirred at the same temperature for 20 minutes. After mixture was ice-cooled, acetic acid (61 μL), sodium triacetoxyborohydride (91 mg), and acetaldehyde (36 μL) were added thereto, and the mixture was stirred for 1 hour under ice-cooling. After a saturated aqueous NaHCO$_3$ solution was added to the reaction mixture, extraction thereof was performed using EtOAc, and the extract was washed with water and saturated brine. The organic layer was dried over MgSO$_4$ and filtered, and the filtrate was concentrated under reduced pressure. The residue was purified by basic silica gel column chromatography (Hex:EtOAc=80:20 to 40:60). The obtained product was dissolved in EtOAc (1 mL), then a 4 M solution of hydrogen chloride in EtOAc (0.3 mL) was added thereto at room temperature, and the mixture was stirred at the same temperature for 10 minutes. The precipitate was collected by filtration, whereby 4-{6-[2-(1-ethylpiperidin-3-yl)ethoxy]-5-(trifluoromethyl)pyridin-3-yl}-7-methyl-7H-pyrrolo[2,3-d]pyrimidine-2-carbonitrile monohydrochloride (92 mg) was obtained as a pale yellow solid.

Example 13

A 4 M solution of hydrogen chloride in EtOAc (0.12 mL) was added to a solution of 4-{4-[2-(1-ethylpiperidin-4-yl)ethoxy]-3-(trifluoromethyl)phenyl}-7-(2-methoxyethyl)-7H-pyrrolo[2,3-d]pyrimidine-2-carbonitrile (80 mg) in CH$_2$Cl$_2$ (1.5 mL) at room temperature, and the mixture was stirred at the same temperature for 0.5 hours. The reaction mixture was concentrated under reduced pressure, and diisopropyl ether was added to the residue. The precipitate was washed with diisopropyl ether, and collected by filtration, whereby 4-{4-[2-(1-ethylpiperidin-4-yl)ethoxy]-3-(trifluoromethyl)phenyl}-7-(2-methoxyethyl)-7H-pyrrolo[2,3-d]pyrimidine-2-carbonitrile monohydrochloride (50 mg) was obtained as a pale yellow solid.

Example 14

4-[4-Hydroxy-3-(trifluoromethyl)phenyl]-7-methyl-7H-pyrrolo[2,3-d]pyrimidine-2-carbonitrile (100 mg) and potassium carbonate (87 mg) were added to a solution of 2-(1-cyclopropylpiperidin-4-yl)ethyl 4-methylbenzenesulfonate (152 mg) in DMAc (2 mL) at room temperature, and the mixture was stirred at 80° C. for 1 hour. After the reaction mixture was cooled to room temperature, EtOAc, water, and a saturated aqueous NaHCO$_3$ solution were added thereto, and the mixture was stirred. Extraction was performed on the mixture using EtOAc, and the extract was washed with water and saturated brine. The organic layer was dried over Na$_2$SO$_4$ and filtered, and the filtrate was concentrated under reduced pressure. The residue was purified by basic silica gel column chromatography (Hex:CHCl$_3$=50:50 to 0:100), whereby 4-{4-[2-(1-cyclopropylpiperidin-4-yl)ethoxy]-3-(trifluoromethyl)phenyl}-7-methyl-7H-pyrrolo[2,3-d]pyrimidine-2-carbonitrile (54 mg) was obtained as pale yellow powder.

Example 15

1-Methyl-L-proline (33 mg), O-(7-azabenzotriazol-1-yl)-N,N,N',N'-tetramethyluronium hexafluorophosphate (85 mg), and N,N-diisopropylethylamine (64 μL) were added to a solution of 4-{4-[2-(piperidin-4-yl)ethoxy]-3-(trifluoromethyl)phenyl}-7-(tetrahydrofuran-2-yl methyl)-7H-pyrrolo[2,3-d]pyrimidine-2-carbonitrile monohydrochloride (80 mg) in DMF (1.6 mL) at room temperature, and the mixture was stirred at the same temperature overnight. After the reaction mixture was diluted with EtOAc, a saturated aqueous NaHCO$_3$ solution and water were added thereto, then extraction thereof was performed using EtOAc, and the extract was washed with saturated brine. The organic layer was dried over Na$_2$SO$_4$ and filtered, and the filtrate was concentrated under reduced pressure. The residue was purified by basic silica gel column chromatography (Hex:CHCl$_3$=50:50 to 0:100). The obtained product was dissolved in EtOAc (1 mL), then a 4 M solution of hydrogen chloride in EtOAc (31 μL) was added thereto at room temperature, and the mixture was stirred at the same temperature for 1 hour. The precipitate was collected by filtration, whereby 4-[4-{2-[1-(1-methyl-L-prolyl)piperidin- 4-yl]ethoxy}-3-(trifluoromethyl)phenyl]-7-(tetrahydrofuran-2-ylmethyl)-7H-pyrrolo[2,3-d]pyrimidine-2-carbonitrile monohydrochloride (77 mg) was obtained as a pale yellow solid.

Example 16

Potassium carbonate (62 mg), potassium iodide (25 mg), and 2-chloro-N,N-dimethylacetamide (18 µL) were added to a mixture of 4-{4-[2-(piperidin-4-yl)ethoxy]-3-(trifluoromethyl)phenyl}-7-(tetrahydrofuran-2-ylmethyl)-7H-pyrrolo[2,3-d]pyrimidine-2-carbonitrile monohydrochloride (80 mg) and acetonitrile (3.2 mL) at room temperature, and the mixture was stirred at 60° C. for 2 hours. After the reaction mixture was cooled to room temperature, the reaction mixture was diluted with EtOAc. Then, a saturated aqueous NaHCO$_3$ solution and water were added thereto, then extraction thereof was performed using EtOAc, and the extract was washed with saturated brine. The organic layer was dried over Na$_2$SO$_4$ and filtered, and the filtrate was concentrated under reduced pressure. The residue was purified by basic silica gel column chromatography (Hex:CHCl$_3$=50:50 to 0:100). The obtained product was dissolved in EtOAc (1 mL), then a 4 M solution of hydrogen chloride in EtOAc (37 µL) was added thereto at room temperature, and the mixture was stirred at the same temperature for 1 hour. The precipitate was collected by filtration, whereby 2-[4-(2-{4-[2-cyano-7-(tetrahydrofuran-2-yl methyl)-7H-pyrrolo[2,3-d]pyrimidin-4-yl]-2-(trifluoromethyl)phenoxy}ethyl)piperidin-1-yl]-N,N-dimethylacetamide monohydrochloride (57 mg) was obtained as a pale yellow solid.

Example 17

2-(1-Methylpyrrolidin-3-yl)ethylamine (32 mg) and N,N-diisopropylethylamine (45 µL) were added to a solution of 4-[4-fluoro-3-(trifluoromethyl)phenyl]-7-methyl-7H-pyrrolo[2,3-d]pyrimidine-2-carbonitrile (75 mg) in DMAc (1.5 mL), then the mixture was stirred at 150° C. for 6 hours under microwave irradiation, and the mixture was further stirred at 160° C. for 3 hours. After the reaction mixture was cooled to room temperature, the reaction mixture was purified by basic silica gel column chromatography (Hex:EtOAc=50:50 to 30:70). The obtained product was dissolved in EtOH (1 mL), and fumaric acid (7 mg) was added thereto. The mixture was concentrated under reduced pressure, and diisopropyl ether was added to the residue. The precipitate was washed with diisopropyl ether, and collected by filtration, whereby 7-methyl-4-[4-{[2-(1-methylpyrrolidin-3-yl)ethyl]amino}-3-(trifluoromethyl)phenyl]-7H-pyrrolo[2,3-d]pyrimidine-2-carbonitrile monofumarate (23 mg) was obtained as an amorphous material.

Example 18

A 4 M solution of hydrogen chloride in dioxane (1 ml) was added to a solution of tert-butyl 4-(2-{4-[7-(2-{[tert-butyl(dimethyl)silyl]oxy}ethyl)-2-cyano-7H-pyrrolo[2,3-d]pyrimidin-4-yl]-2-(trifluoromethyl)phenoxy}ethyl)piperidine-1-carboxylate (150 mg) in dioxane (1 mL) at room temperature, and the mixture was stirred at the same temperature for 1 hour. After the reaction mixture was concentrated under reduced pressure, the precipitate was washed with diisopropyl ether, and collected by filtration, whereby 7-(2-hydroxyethyl)-4-{4-[2-(piperidin-4-yl)ethoxy]-3-(trifluoromethyl)phenyl}-7H-pyrrolo[2,3-d]pyrimidine-2-carbonitrile monohydrochloride (110 mg) was obtained as a pale yellow solid.

Example 28

Trifluoroacetic acid (40 mL) was added to a solution of tert-butyl 4-(2-{[5-(2-cyano-9-methyl-9H-purin-6-yl)-3-(trifluoromethyl)pyridin-2-yl]oxy}ethyl)piperidine-1-carboxylate (5.8 g) in CH$_2$Cl$_2$ (80 mL)-acetonitrile (20 mL) at room temperature, and the mixture was stirred at the same temperature for 1 hour. The reaction mixture was concentrated under reduced pressure, and CH$_2$Cl$_2$ (10 mL) was added to the residue. A 4 M solution of hydrogen chloride in EtOAc (10 mL) was added to the mixture at room temperature, and the resultant mixture was stirred at the same temperature for 10 minutes. EtOAc (5 mL) and disiopropyl ether (150 mL) were added to the reaction mixture at room temperature, and the resultant mixture was stirred for 30 minutes. The precipitate was collected by filtration, whereby 9-methyl-6-{6-[2-(piperidin-4-yl)ethoxy]-5-(trifluoromethyl)pyridin-3-yl}-9H-purine-2-carbonitrile monohydrochloride (5.1 g) was obtained as a solid.

Example 39

Triethylamine (2.7 mL) was added to a suspension of 9-methyl-6-{6-[2-(piperidin-4-yl)ethoxy]-5-(trifluoromethyl)pyridin-3-yl}-9H-purine-2-carbonitrile monohydrochloride (3.0 g) in dichloroethane (60 mL) at room temperature, and the mixture was stirred at the same temperature for 20 minutes. After the reaction mixture was ice-cooled, acetic acid (1.8 mL), sodium triacetoxyborohydride (2.7 g) were added thereto, and a solution of acetaldehyde (1.1 mL) in dichloroethane (5 mL) was added thereto. The mixture was stirred for 1 hour under ice-cooling. After a saturated aqueous NaHCO$_3$ solution was added to the reaction mixture, extraction thereof was performed using CHCl$_3$, and the extract was washed with saturated brine. The organic layer was dried over Na$_2$SO$_4$ and filtered, and the filtrate was concentrated under reduced pressure. The residue was suspended in EtOH (80 mL), and the suspension was dissolved by stirring for 30 minutes while heating to reflux. The mixture was cooled to room temperature, and the precipitate was collected by filtration, whereby 6-{6-[2-(1-ethylpiperidin-4-yl)ethoxy]-5-(trifluoromethyl)pyridin-3-yl}-9-methyl-9H-purine-2-carbonitrile (1.8 g) was obtained as a crystal (heat absorption peak temperature obtained by a TG/DTA analysis: near 191° C.).

Example 103

By the same method as in Example 13 except that one equivalent fumaric acid was used instead of a solution of hydrogen chloride in EtOAc, 7-ethyl-4-{4-[2-(1-ethylpiperidin-4-yl)ethoxy]-3-(trifluoromethyl)phenyl}-7H-pyrrolo[2,3-d]pyrimidine-2-carbonitrile monofumarate was obtained.

Example 114 tert-Butyl 4-(2-{4-[2-cyano-7-(oxetan-3-yl)-7H-pyrrolo[2,3-d]pyrimidin-4-yl]-2-(trifluoromethyl)phenoxy}ethyl)piperidine-1-carboxylate was reacted in the same method as in Preparation Example 24. Subsequently, by the same method as in Example 12 except that one equivalent fumaric acid was used instead of a solution of hydrogen chloride in EtOAc, 4-{4-[2-(1-ethylpiperidin-4-yl)ethoxy]-3-(trifluoromethyl)phenyl}-7-(oxetan-3-yl)-7H-pyrrolo[2,3-d]pyrimidine-2-carbonitrile monofumarate was obtained.

Example 115 tert-Butyl 4-(2-{4-[2-cyano-7-(oxetan-3-yl)-7H-pyrrolo[2,3-d]pyrimidin-4-yl]-2-(trifluoromethyl)phenoxy}ethyl)piperidine-1-carboxylate was reacted in the same method as in Preparation Example 24. Subsequently, by the same method as in Example 15 except that one equivalent fumaric acid was used instead of a solution of hydrogen chloride in EtOAc, 4-[4-{2-[1-(1-methyl-L-prolyl)piperidin-4-yl]ethoxy}-3-(trifluoromethyl)phenyl]-7-(oxetan-3-yl)-7H-pyrrolo[2,3-d]pyrimidine-2-carbonitrile monofumarate was obtained.

Example 134

A 4 M solution of hydrogen chloride in EtOAc (4.2 mL) was added dropwise to a suspension of 6-{6-[2-(1-ethylpiperidin-4-yl)ethoxy]-5-(trifluoromethyl)pyridin-3-yl}-9-methyl-9H-purine-2-carbonitrile (3.9 g) in EtOH (58.5 mL) at room temperature, whereby a solution was obtained. After the solution was concentrated under reduced pressure, the residue was suspended in EtOH (117 mL). The suspension was stirred at 80° C. to obtain a solution, and the solution was cooled to room temperature while stirring. The solution was stirred at room temperature overnight. The precipitated solid was filtered, and the solid was washed with EtOH, whereby 6-{6-[2-(1-ethylpiperidin-4-yl)ethoxy]-5-(trifluoromethyl)pyridin-3-yl}-9-methyl-9H-purine-2-carbonitrile monohydrochloride (3.2 g) was obtained as a crystal (heat absorption peak temperature obtained by a TG/DTA analysis: near 220° C.).

Example 135

Isobutylene oxide (38 μL) and N,N-diisopropylethylamine (73 μL) were added to a solution of 7-methyl-4-[6-{[1-(piperidin-4-yl carbonyl)piperidin-4-yl]methoxy}-5-(trifluoromethyl)pyridin-3-yl]-7H-pyrrolo[2,3-d]pyrimidine-2-carbonitrile monohydrochloride (120 mg) in EtOH (2.4 mL)-DMF (0.5 mL) at room temperature, and the mixture was stirred at 60° C. overnight. The reaction mixture was cooled to room temperature, and EtAOc and water were added thereto. Extraction was performed on the mixture using EtOAc, and the extract was washed with saturated brine. The organic layer was dried over $MgSO_4$ and filtered, and the filtrate was concentrated under reduced pressure. The residue was purified by basic silica gel column chromatography (Hex: $CHCl_3$=70:30 to 20:80), whereby 4-{6-[(1-{[1-(2-hydroxy-2-methylpropyl)piperidin-4-yl]carbonyl}piperidin-4-yl)methoxy]-5-(trifluoromethyl)pyridin-3-yl}-7-methyl-7H-pyrrolo[2,3-d]pyrimidine-2-carbonitrile (93 mg) was obtained as a solid.

Example 136

Triethylamine (30 μL), 1H-benzotriazole-1-methanol (48 mg), and sodium triacetoxyborohydride (91 mg) were added to a solution of 9-methyl-6-{6-[2-(piperidin-4-yl)ethoxy]-5-(trifluoromethyl)pyridin-3-yl}-9H-purine-2-carbonitrile monohydrochloride (100 mg) in THF (1.5 mL)-EtOH (1.5 mL), and the mixture was stirred at room temperature for 16 hours. After a saturated aqueous $NaHCO_3$ solution and EtOAc were added to the reaction mixture, extraction thereof was performed using EtOAc, and the extract was washed with saturated brine. The organic layer was dried over $MgSO_4$ and filtered, and the filtrate was concentrated under reduced pressure. The residue was purified by silica gel column chromatography ($CHCl_3$:MeOH=100:0 to 80:20), whereby 9-methyl-6-{6-[2-(1-methylpiperidin-4-yl)ethoxy]-5-(trifluoromethyl)pyridin-3-yl}-9H-purine-2-carbonitrile (57 mg) was obtained as a solid.

Example 143

By the same method as in Example 15 except that one equivalent fumaric acid was used instead of a solution of hydrogen chloride in EtOAc, 7-methyl-4-[6-(2-{[(3S)-1-(1-methyl-D-prolyl)pyrrolidin-3-yl]oxy}ethoxy)-5-(trifluoromethyl)pyridin-3-yl]-7H-pyrrolo[2,3-d]pyrimidine-2-carbonitrile monofumarate was obtained.

By the same method as in Examples described above, compounds of Examples shown in the following tables were prepared. Structures of respective Example compounds are shown in Tables 25 to 51, and preparing methods, and physicochemical data are shown in Tables 52 to 64.

TABLE 3

| PEx | PSyn | Str | DAT |
|---|---|---|---|
| 1 | 1 | 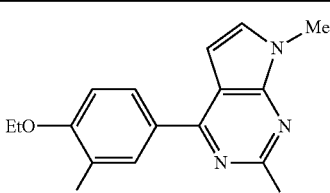 | ESI+: 356, 358 |
| 2 | 2 | 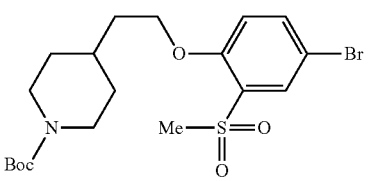 | ESI+: 462, 464 |

TABLE 3-continued
| PEx | PSyn | Str | DAT |
|---|---|---|---|
| 3 | 3 | 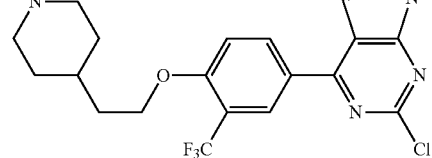 | ESI+: 530 |
| 4 | 4 | 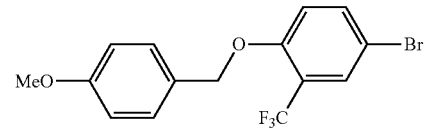 | CI+: 361, 363 |
| 5 | 5 | 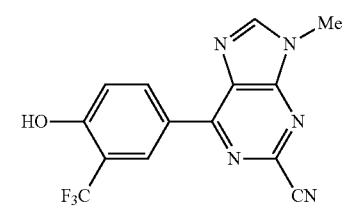 | ESI+: 320 |
| 6 | 6 | 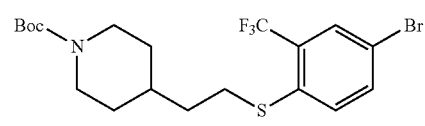 [SMILES: CC(C)(C)OC(=O)N1CCC(CCSc2ccc(Br)cc2C(F)(F)F)CC1] | ESI+: 490, 492 [M + Na] |
| 7 | 7 | 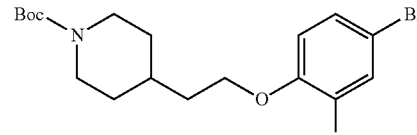 | ESI+: 474, 476 [M + Na] |
| 8 | 8 | 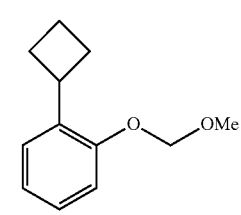 [SMILES: COCOc1ccccc1C1CCC1] | ESI+: 215 [M + Na] |
TABLE 4
| PEx | PSyn | Str | DAT |
|---|---|---|---|
| 9 | 9 | 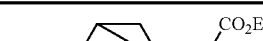 | ESI+: 298 |
| 10 | 10 | 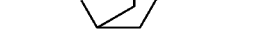 | ESI+: 286 |
| 11 | 11 | 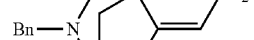 | APCI/ESI+: 256 |

TABLE 4-continued
| PEx | PSyn | Str | DAT |
|---|---|---|---|
| 12 | 12 | 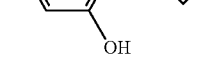 | ESI+: 149 |
| 13 | 13 | 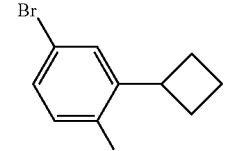 | EI: 226, 228 |
| 14 | 14 | 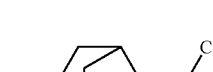 | ESI+: 298 |
| 15 | 15 | 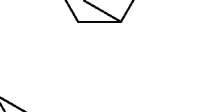 | ESI+: 432 [M + Na] |
| 16 | 16 | 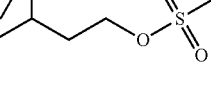 | ESI+: 556 |
| 17 | 17 | 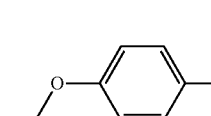 | ESI+: 223, 225, 227 |
| 18 | 18 | 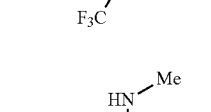 | ESI+: 193, 195, 197 |
TABLE 5
| PEx | PSyn | Str | DAT |
|---|---|---|---|
| 19 | 19 | 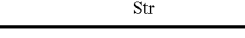 | NMR1: 2.63 (3H, s), 3.73 (3H, s) ESI+: 217, 219, 221 |

TABLE 5-continued

| PEx | PSyn | Str | DAT |
|---|---|---|---|
| 20 | 20 | | ESI+: 272, 274, 276 |
| 21 | 21 | | ESI+: 452, 454 |
| 22 | 22 | | ESI+: 271, 273 |
| 23 | 23 | | ESI+: 525, 527 |
| 24 | 24 | | ESI+: 483, 485 |
| 25 | 25 | | ESI+: 307 |

TABLE 6

| PEx | PSyn | Str | DAT |
|---|---|---|---|
| 26 | 26 | | ESI+: 511, 513 |

TABLE 6-continued

| PEx | PSyn | Str | DAT |
|---|---|---|---|
| 27 | 27 | | ESI+: 522 [M + Na] |
| 28 | 28 | | ESI+: 475, 477 [M + Na] |
| 29 | 29 | | ESI+: 212 |
| 30 | 30 | | ESI+: 170 |
| 31 | 31 | | ESI+: 187, 189 |
| 32 | 32 | | ESI+: 609, 611 |
| 33 | 33 | | ESI+: 449, 451 |

TABLE 7

| PEx | PSyn | Str | DAT |
|---|---|---|---|
| 34 | 34 | | ESI+: 560 |

TABLE 7-continued
| PEx | PSyn | Str | DAT |
|---|---|---|---|
| 35 | 1 | 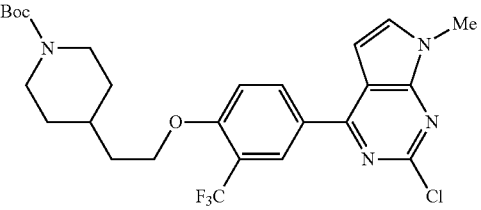 [SMILES: Cn1ccc2c(-c3ccc(OCCC4CCN(C(=O)OC(C)(C)C)CC4)c(C(F)(F)F)c3)nc(Cl)nc21] | ESI+: 539, 541 |
| 36 | 1 | 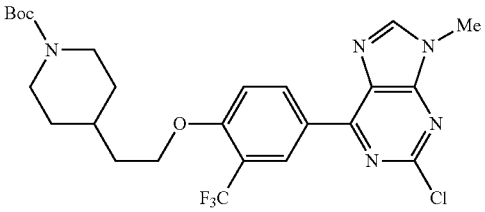 | ESI+: 540, 542 |
| 37 | 3 | 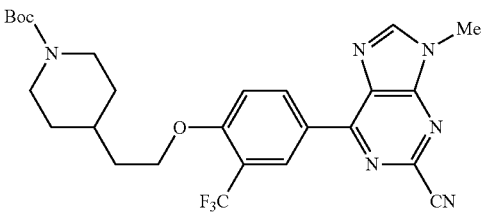 | ESI+: 531 |
| 38 | 1 | 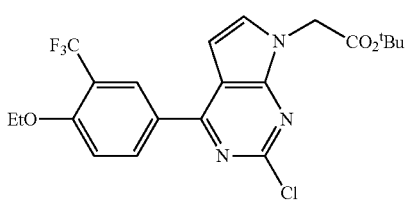 [SMILES: CCOc1ccc(-c2nc(Cl)nc3c2ccn3CC(=O)OC(C)(C)C)cc1C(F)(F)F] | ESI+: 456, 458 |
| 39 | 19 | 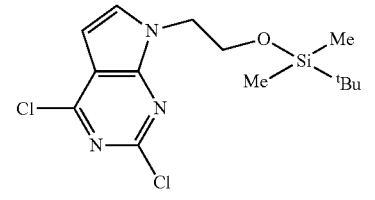 [SMILES: CC(C)(C)[Si](C)(C)OCCn1ccc2c(Cl)nc(Cl)nc21] | ESI+: 346, 348, 350 |
| 40 | 1 | 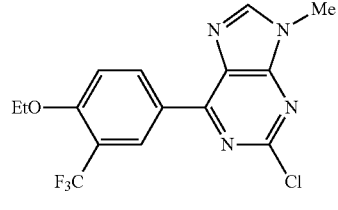 | ESI+: 357, 359 |

TABLE 8
| PEx | PSyn | Str | DAT |
|---|---|---|---|
| 41 | 1 | 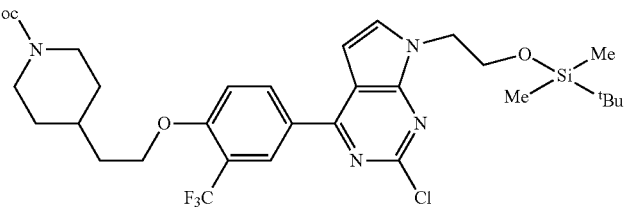 | ESI+: 683, 685 |
| 42 | 3 | 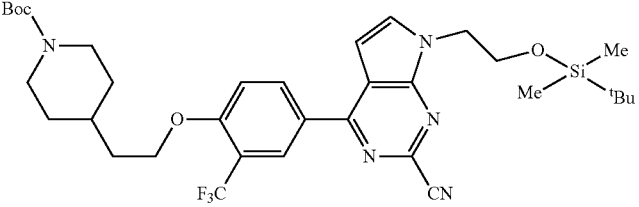 [SMILES: CC(C)(C)OC(=O)N1CCC(CCOc2ccc(-c3nc(C#N)nc4c3ccn4CCO[Si](C)(C)C(C)(C)C)cc2C(F)(F)F)CC1] | ESI+: 674 |
| 43 | 33 | 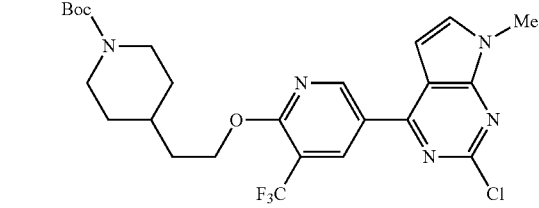 | ESI+: 540, 542 |
| 44 | 27 | 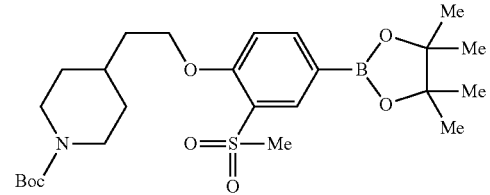 [SMILES: CC(C)(C)OC(=O)N1CCC(CCOc2ccc(B3OC(C)(C)C(C)(C)O3)cc2S(C)(=O)=O)CC1] | ESI+: 510 |
| 45 | 3 | 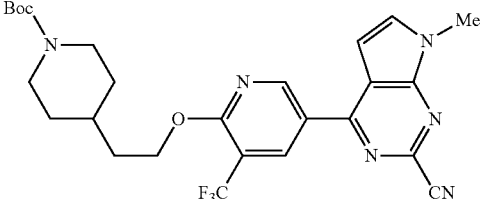 | ESI+: 531 |
| 46 | 33 | 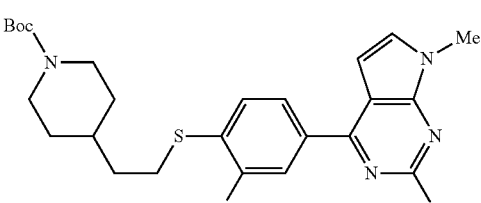 | ESI+: 555, 557 |
| 47 | 4 | 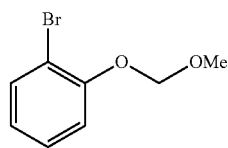 [SMILES: COCOc1ccccc1Br] | EI: 216, 218 |

TABLE 9
| PEx | PSyn | Str | DAT |
|---|---|---|---|
| 48 | 48 | 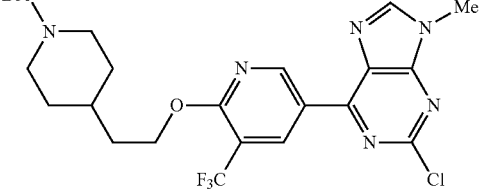 | ESI+: 541, 543 |
| 49 | 3 | 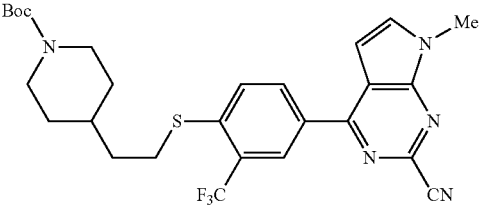 | ESI+: 546 |
| 50 | 4 | 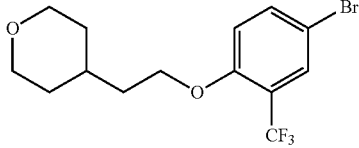 [SMILES: FC(F)(F)c1cc(Br)ccc1OCCC1CCOCC1] | ESI+: 353, 355 |
| 51 | 19 | 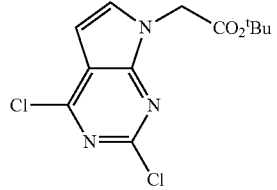 [SMILES: CC(C)(C)OC(=O)Cn1ccc2c(Cl)nc(Cl)nc21] | ESI+: 302, 304, 306 |
| 52 | 15 | 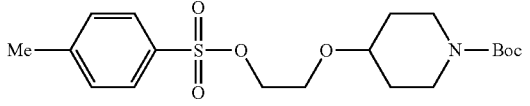 | APCI/ESI+: 344 [M-tBu + H] |
| 53 | 16 | 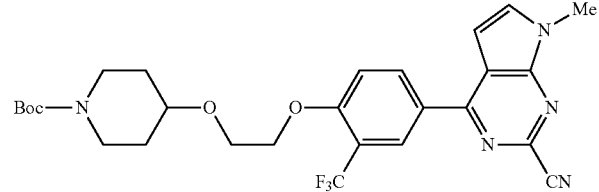 | ESI+: 546 |
| 54 | 27 | 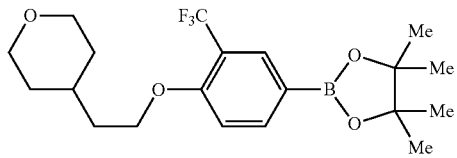 [SMILES: CC1(C)OB(c2ccc(OCCC3CCOCC3)c(C(F)(F)F)c2)OC1(C)C] | ESI+: 423 [M + Na] |
| 55 | 11 | 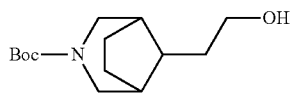 | ESI+: 256 |

TABLE 10

| PEx | PSyn | Str | DAT |
|---|---|---|---|
| 56 | 1 | | ESI+: 540, 542 |
| 57 | 15 | | ESI+: 432 [M + Na] |
| 58 | 16 | | ESI+: 546 |
| 59 | 15 | | ESI+: 406 [M + Na] |
| 60 | 16 | | ESI+: 556 |
| 61 | 7 | | ESI+: 460, 462 [M + Na] |
| 62 | 16 | | ESI+: 530 |

TABLE 11

| PEx | PSyn | Str | DAT |
|---|---|---|---|
| 63 | 1 | | ESI+: 470, 472 |
| 64 | 1 | | ESI+: 549, 551 |
| 65 | 27 | | ESI+: 508 [M + Na] |
| 66 | 3 | | ESI+: 461 |
| 67 | 1 | | ESI+: 554, 556 |
| 68 | 3 | | ESI+: 545 |

TABLE 12

| PEx | PSyn | Str | DAT |
|---|---|---|---|
| 69 | 19 | | ESI+: 246, 248, 250 |
| 70 | 1 | | ESI+: 330, 332 |
| 71 | 28 | | ESI+: 453, 455 |
| 72 | 1 | | ESI+: 525, 527 |
| 73 | 33 | | ESI+: 540, 542 |
| 74 | 1 | | ESI+: 583, 585 |
| 75 | 33 | | ESI+: 539, 541 |

TABLE 13
| PEx | PSyn | Str | DAT |
|---|---|---|---|
| 76 | 3 | 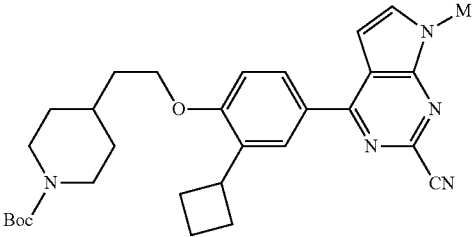 | ESI+: 516 |
| 77 | 33 | 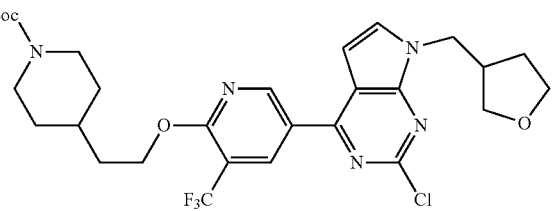 | ESI+: 610, 612 |
| 78 | 3 | 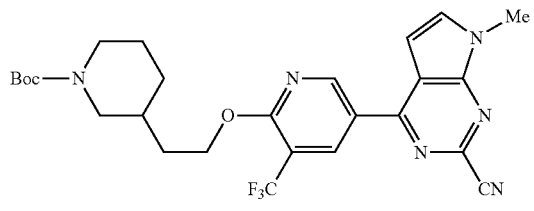 [SMILES: Cn1ccc2c(-c3cnc(OCCC4CCCN(C(=O)OC(C)(C)C)C4)c(C(F)(F)F)c3)nc(C#N)nc21] | ESI+: 531 |
| 79 | 3 | 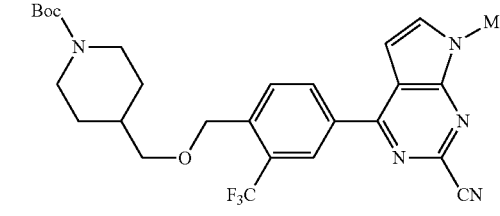 | ESI+: 530 |
| 80 | 1 | 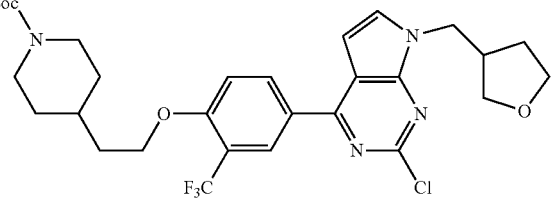 | ESI+: 609, 611 |
| 81 | 7 | 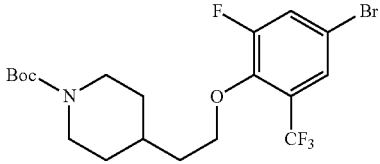 | ESI+: 492, 494 [M + Na] |
| 82 | 3 | 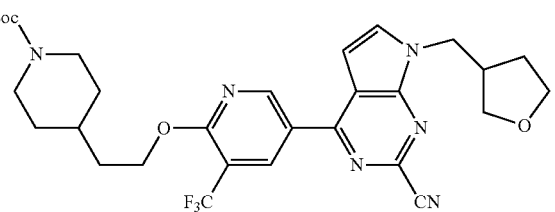 | ESI+: 601 |

TABLE 14
| PEx | PSyn | Str | DAT |
|---|---|---|---|
| 83 | 33 | 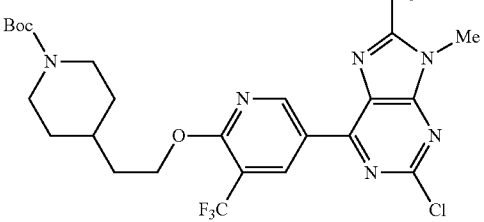 | ESI+: 631, 633 [M + Na] |
| 84 | 3 | 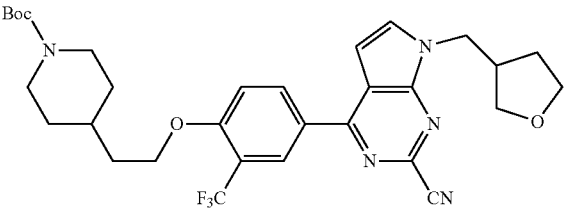 [SMILES: CC(C)(C)OC(=O)N1CCC(CCOc2ccc(-c3nc(Cl)nc4c3ccn4CC3CCOC3)cc2C(F)(F)F)CC1] | ESI+: 600 |
| 85 | 3 | 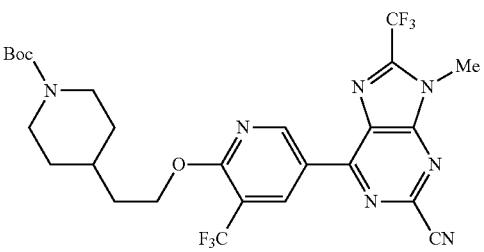 [SMILES: Cn1c(C(F)(F)F)nc2c(-c3cnc(OCCC4CCN(C(=O)OC(C)(C)C)CC4)c(C(F)(F)F)c3)nc(C#N)nc21] | ESI+: 622 [M + Na] |
| 86 | 3 | 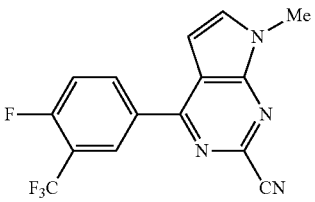 [SMILES: Cn1ccc2c(-c3ccc(F)c(C(F)(F)F)c3)nc(C#N)nc21] | ESI+: 321 |
| 87 | 19 | 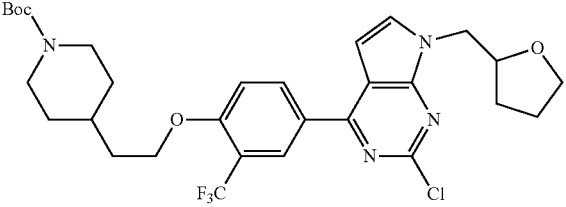 | ESI+: 609, 611 |
| 88 | 3 | 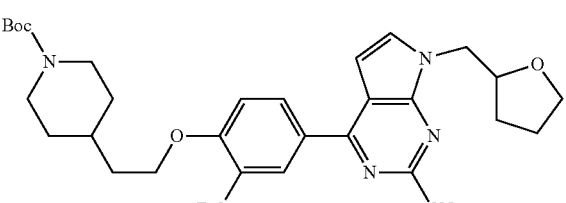 | ESI+: 600 |

TABLE 15

| PEx | PSyn | Str | DAT |
|---|---|---|---|
| 89 | 20 | | ESI+: 286, 288, 290 |
| 90 | 20 | | NMR1: 1.57-1.67 (1H, m), 1.88-1.99 (1H, m), 2.78-2.88 (1H, m), 3.47-3.53 (1H, m), 3.59-3.68 (2H, m), 3.75-3.82 (1H, m), 4.20-4.31 (2H, m), 8.79 (1H, s) ESI+: 273, 275, 277 |
| 91 | 1 | | ESI+: 679, 681 |
| 92 | 3 | | ESI+: 562 [M + Na] |
| 93 | 20 | | ESI+: 391 |
| 94 | 33 | | ESI+: 448, 450 |
| 95 | 1 | | ESI+: 610, 612 |

TABLE 16
| PEx | PSyn | Str | DAT |
|---|---|---|---|
| 96 | 33 | 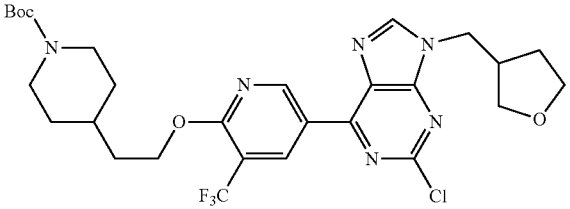 [SMILES: CC(C)(C)OC(=O)N1CCC(CCOc2ncc(-c3nc(Cl)nc4c3ncn4CC3CCOC3)cc2C(F)(F)F)CC1] | ESI+: 611, 613 |
| 97 | 1 | 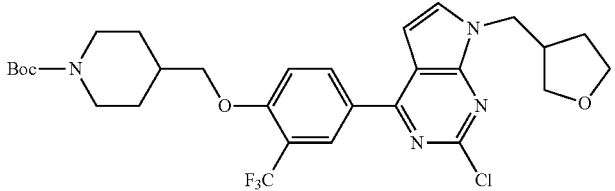 | ESI+: 595, 597 |
| 98 | 10 | 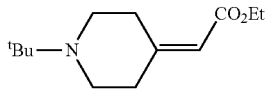 [SMILES: CCOC(=O)C=C1CCN(C(C)(C)C)CC1] | ESI+: 226 |
| 99 | 3 | 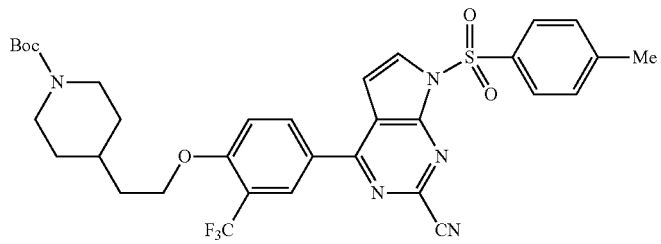 [SMILES: Cc1ccc(S(=O)(=O)n2ccc3c(-c4ccc(OCCC5CCN(C(=O)OC(C)(C)C)CC5)c(C(F)(F)F)c4)nc(C#N)nc32)cc1] | ESI+: 670 |
| 100 | 3 | 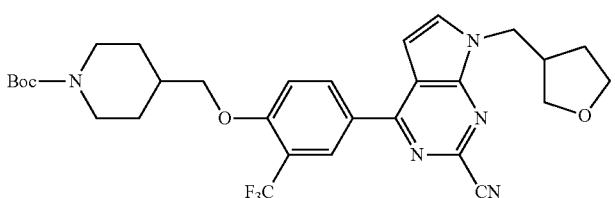 | ESI+: 586 |
| 101 | 3 | 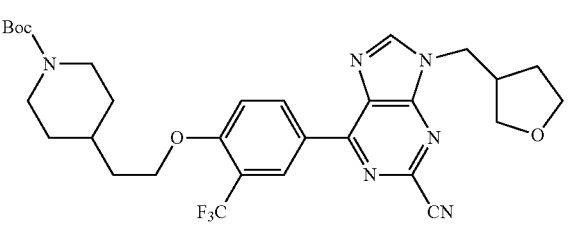 | ESI+: 601 |
| 102 | 25 | 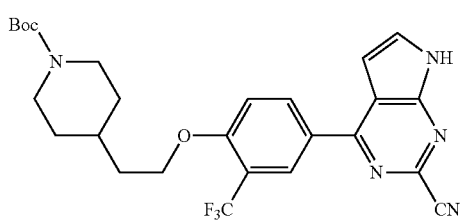 [SMILES: CC(C)(C)OC(=O)N1CCC(CCOc2ccc(-c3nc(C#N)nc4[nH]ccc34)cc2C(F)(F)F)CC1] | ESI+: 516 |

TABLE 17
| PEx | PSyn | Str | DAT |
|---|---|---|---|
| 103 | 33 | 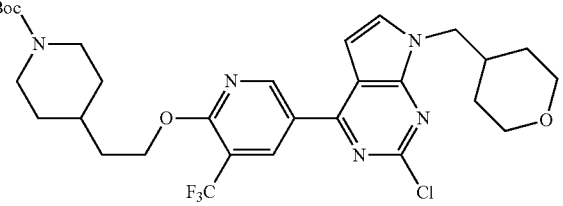 | ESI+: 624, 626 |
| 104 | 3 | 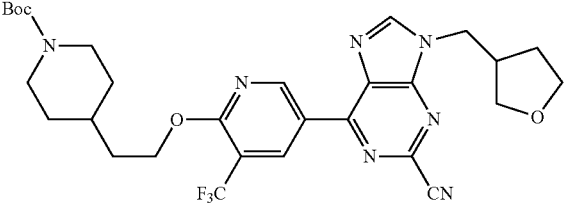 | ESI+: 602 |
| 105 | 5 | 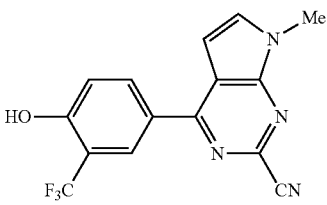 [SMILES: Cn1ccc2c(-c3ccc(O)c(C(F)(F)F)c3)nc(C#N)nc21] | ESI+: 319 |
| 106 | 9 | 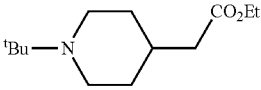 [SMILES: CCOC(=O)CC1CCN(C(C)(C)C)CC1] | ESI+: 228 |
| 107 | 2 | 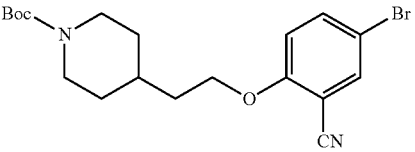 [SMILES: CC(C)(C)OC(=O)N1CCC(CCOc2ccc(Br)cc2C#N)CC1] | ESI+: 409, 411 |
| 108 | 19 | 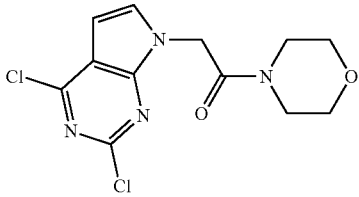 [SMILES: O=C(Cn1ccc2c(Cl)nc(Cl)nc21)N1CCOCC1] | ESI+: 315, 317, 319 |
| 109 | 30 | 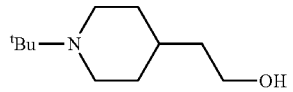 | ESI+: 186 |
| 110 | 110 | 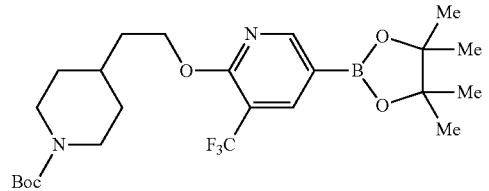 [SMILES: CC(C)(C)OC(=O)N1CCC(CCOc2ncc(B3OC(C)(C)C(C)(C)O3)cc2C(F)(F)F)CC1] | ESI+: 501 |

TABLE 18

| PEx | PSyn | Str | DAT |
|---|---|---|---|
| 111 | 33 | | ESI+: 566 |
| 112 | 15 | | ESI+: 370 |
| 113 | 3 | | ESI+: 637 [M + Na] |
| 114 | 32 | | ESI+: 581, 583 |
| 115 | 16 | | ESI+: 488 |
| 116 | 31 | Chiral | ESI+: 166, 168 |
| 117 | 31 | | ESI+: 184, 186 |
| 118 | 16 | | ESI+: 538 [M + Na] |

TABLE 19
| PEx | PSyn | Str | DAT |
|---|---|---|---|
| 119 | 16 | 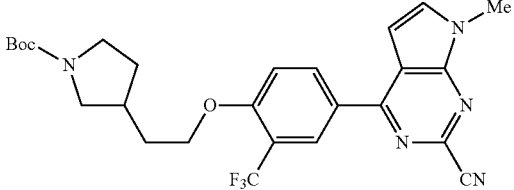 [SMILES: Cn1ccc2c(-c3ccc(OCCC4CCN(C(=O)OC(C)(C)C)C4)c(C(F)(F)F)c3)nc(C#N)nc21] | ESI+: 516 |
| 120 | 19 | 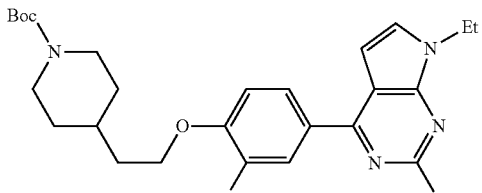 | ESI+: 544 |
| 121 | 15 | 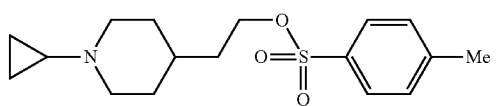 [SMILES: Cc1ccc(S(=O)(=O)OCCC2CCN(C3CC3)CC2)cc1] | ESI+: 324 |
| 122 | 15 | 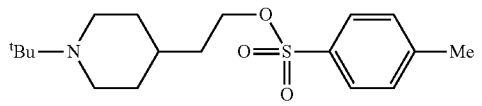 [SMILES: Cc1ccc(S(=O)(=O)OCCC2CCN(C(C)(C)C)CC2)cc1] | ESI+: 340 |
| 123 | 33 | 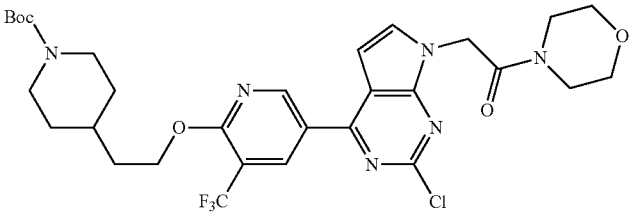 | ESI+: 653, 655 |
| 124 | 3 | 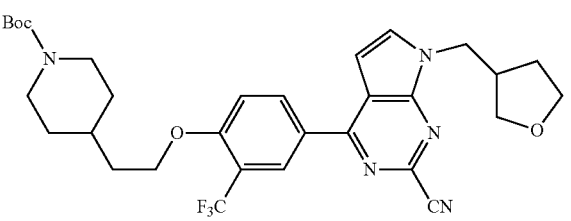 | ESI+: 557 |
| 125 | 32 | 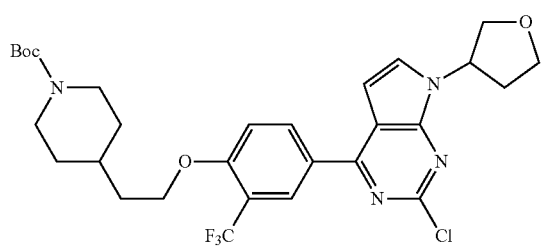 [SMILES: CC(C)(C)OC(=O)N1CCC(CCOc2ccc(-c3nc(Cl)nc4c3ccn4C3CCOC3)cc2C(F)(F)F)CC1] | ESI+: 595, 597 |

TABLE 20

| PEx | PSyn | Str | DAT |
|---|---|---|---|
| 126 | 3 | | ESI+: 600 |
| 127 | 3 | | ESI+: 644 |
| 128 | 3 | | ESI+: 586 |
| 129 | 3 | | ESI+: 572 |
| 130 | 33 | | ESI+: 558, 560 |
| 131 | 19 | | ESI+: 573 |

TABLE 21

| PEx | PSyn | Str | DAT |
|---|---|---|---|
| 132 | 3 | | ESI+: 549 |
| 133 | 133 | | ESI+: 554 [M + Na] |
| 134 | 4 | | ESI+: 460, 462 [M + Na] |
| 135 | 27 | | ESI+: 508 [M + Na] |
| 136 | 27 | | NMR2: 1.34 (12H, s), 1.44 (3H, t, J = 7.0 Hz), 4.14 (2H, q, J = 7.0 Hz), 6.96 (1H, d, J = 8.4 Hz), 7.90 (1H, dd, J = 1.3, 8.4 Hz), 7.98-8.01 (1H, m) |
| 137 | 137 | | ESI+: 296 [M + Na] |
| 138 | 138 | | ESI+: 628 |
| 139 | 139 | | ESI+: 433 HCl |

TABLE 22

| PEx | PSyn | Str | | DAT |
|---|---|---|---|---|
| 140 | 138 | (structure) | Chiral | ESI+: 629 |
| 141 | 10 | (structure) | | ESI+: 210 |
| 142 | 9 | (structure) | | ESI+: 212 |
| 143 | 11 | (structure) | | ESI+: 170 |
| 144 | 2 | (structure) | | ESI+: 393, 395 |
| 145 | 33 | (structure) | | ESI+: 481, 483 |
| 146 | 28 | (structure) | | ESI+: 339, 341 [M − Boc + H] |
| 147 | 2 | (structure) | | ESI+: 409, 411 |

TABLE 23

| PEx | PSyn | Str | DAT |
|---|---|---|---|
| 148 | 33 | | ESI+: 497, 499 |
| 149 | 137 | Chiral | ESI+: 274 |
| 150 | 30 | Chiral | ESI+: 232 |
| 151 | 2 | Chiral | ESI+: 455, 457 |
| 152 | 2 | | ESI+: 469, 471 |
| 153 | 33 | | ESI+: 556, 558 |
| 154 | 33 | Chiral | ESI+: 542, 544 |
| 155 | 3 | | ESI+: 547 |

TABLE 24

| PEx | PSyn | Str | | DAT |
|---|---|---|---|---|
| 156 | 3 | | Chiral | ESI+: 533 |
| 157 | 33 | | Chiral | ESI+: 542, 544 |
| 158 | 3 | | Chiral | ESI+: 533 |
| 159 | 33 | | | ESI+: 526, 528 |
| 160 | 3 | | | ESI+: 517 |
| 161 | 138 | | Chiral | ESI+: 614 |
| 162 | 30 | | Chiral | ESI+: 232 |

TABLE 24-continued

| PEx | PSyn | Str | | DAT |
|---|---|---|---|---|
| 163 | 2 | [Structure: Boc-pyrrolidine-O-CH2CH2-O-pyridine with CF3 and Br substituents] | Chiral | ESI+: 477, 479 [M + Na] |

TABLE 25

| Ex | Str | | |
|---|---|---|---|
| 1 | [Structure: 4-(4-ethoxy-3-trifluoromethylphenyl)-7-methyl-7H-pyrrolo[2,3-d]pyrimidine-2-carbonitrile] | | |
| 2 | [Structure: piperidinyl-ethoxy-phenyl-pyrrolopyrimidine-carbonitrile] | HCl | |
| 3 | [Structure: (Me)2N-C(O)-CH2-piperidinyl-ethoxy-phenyl-pyrrolopyrimidine-carbonitrile] | | |

TABLE 25-continued

| Ex | Str | | |
|---|---|---|---|
| 4# | [Structure: pyrrolopyrimidine with N-CH2-COOH side chain] | | |
| 5 | [Structure: pyrrolopyrimidine with N-CH2-C(O)-N-methylpiperazine] | | |
| 6 | [Structure: N-methylpyrrolidine-C(O)-piperidinyl-ethoxy-phenyl-purine-carbonitrile] | Chiral | |

TABLE 26

| Ex | Str | |
|---|---|---|
| 7 | [Structure: (Me)2N-C(O)-piperidinyl-ethoxy-phenyl-purine-carbonitrile] | |
| 8 | [Structure: tetrahydropyranyl-ethoxy-phenyl-pyrrolopyrimidine with N-methylpiperazine amide] | HCl |

TABLE 26-continued
| Ex | Str |
|---|---|
| 9# | 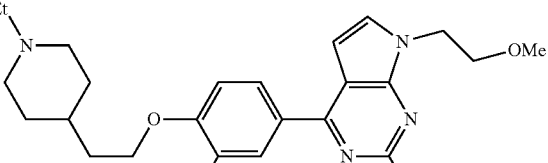 |
| 10 | |
| 11 | |
| 12 | |
TABLE 27
| Ex | Str |
|---|---|
| 13 | 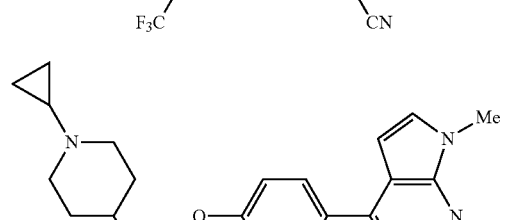 |
| 14 | |

TABLE 27-continued

| Ex | Str | |
|---|---|---|
| 15 | (structure) | Chiral, HCl |
| 16 | (structure) | HCl |
| 17# | (structure) | Fum |
| 18 | (structure) | HCl |

TABLE 28

| Ex | Str | |
|---|---|---|
| 19 | (structure) | HCl |
| 20 | (structure) | |
| 21 | (structure) | |
| 22# | (structure) | |

TABLE 28-continued
| Ex | Str |
|----|-----|
| 23 | 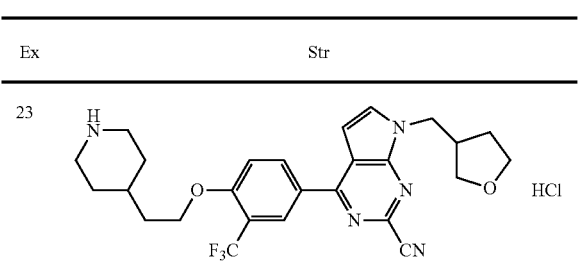 HCl |
| 24 | 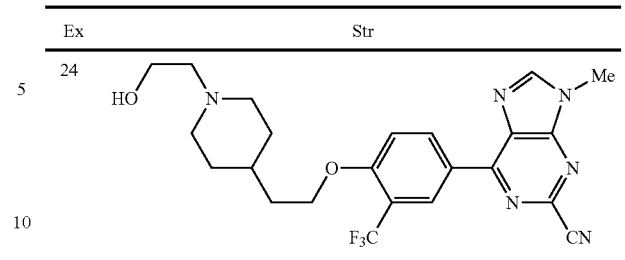 |
TABLE 29
| Ex | Str |
|----|-----|
| 25 | 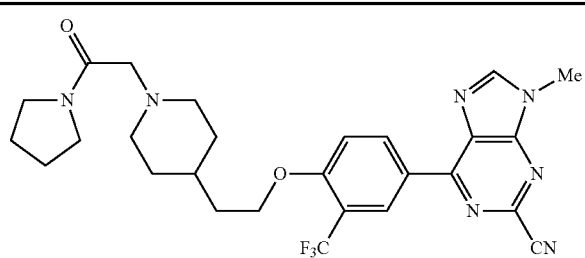 |
| 26 | 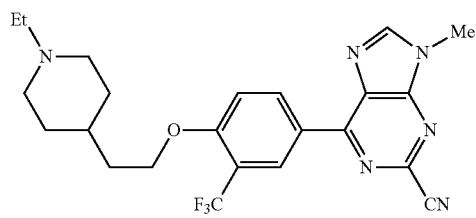 [SMILES: CCN1CCC(CCOc2ccc(-c3nc(C#N)nc4c3ncn4C)cc2C(F)(F)F)CC1] |
| 27 | 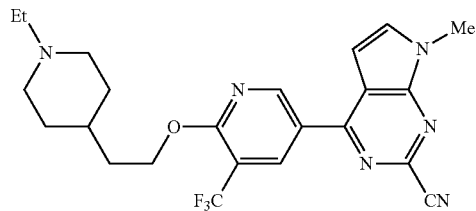 [SMILES: CCN1CCC(CCOc2ncc(-c3nc(C#N)nc4c3ccn4C)cc2C(F)(F)F)CC1] |
| 28 | 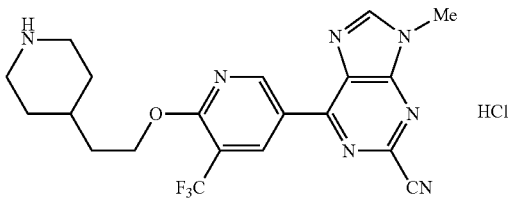 [SMILES: Cn1cnc2c(-c3cnc(OCCC4CCNCC4)c(C(F)(F)F)c3)nc(C#N)nc21 ; Cl] HCl |
| 29 | Chiral 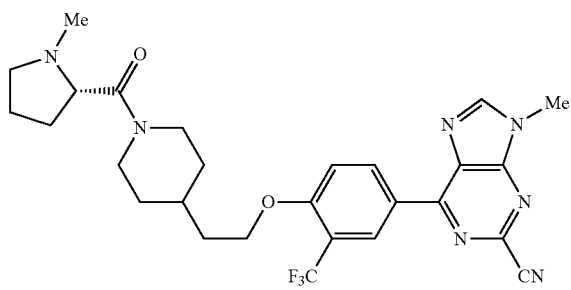 |

TABLE 29-continued
| Ex | Str |
|---|---|
| 30 | Chiral 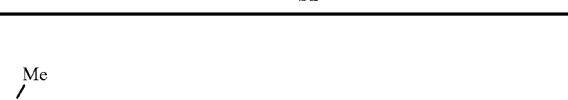 |
TABLE 30
| Ex | Str |
|---|---|
| 31 | 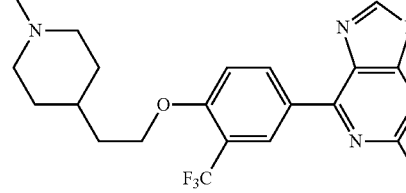 |
| 32 | 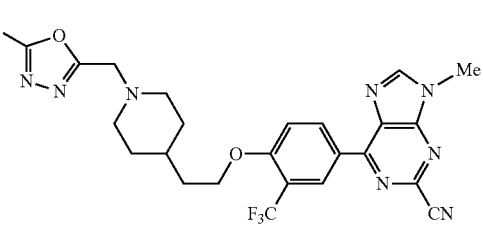 |
| 33 | 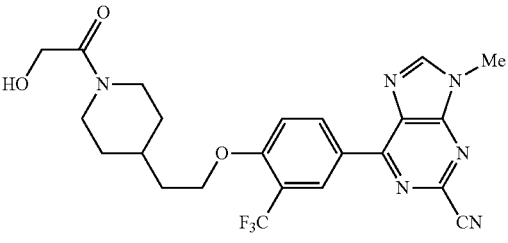 |
| 34 | 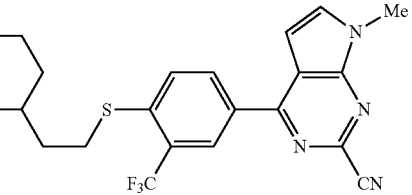 HCl |
| 35 | 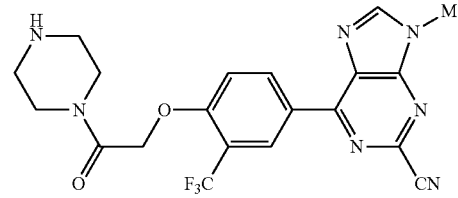 HCl |
TABLE 30-continued
| Ex | Str |
|---|---|
| 36 | 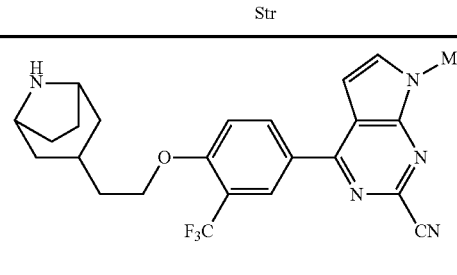 HCl |
TABLE 31
| Ex | Str |
|---|---|
| 37 | 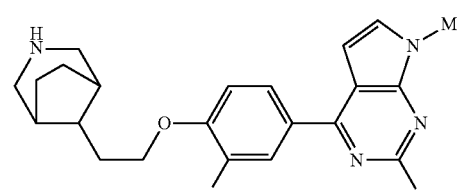 HCl |
| 38 | 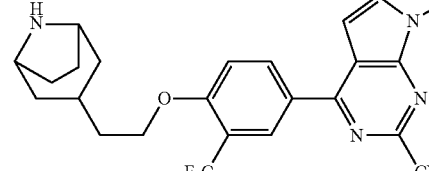 HCl |
| 39 | 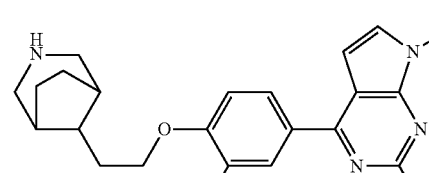 |

TABLE 31-continued
| Ex | Str |
|---|---|
| 40 | 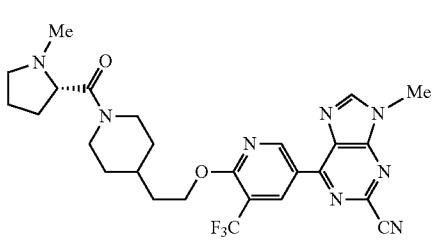 Chiral |
| 41 | 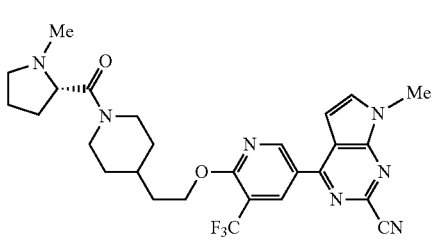 Chiral |
| 42 | 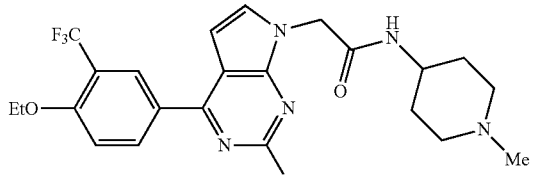 |
TABLE 32
| Ex | Str |
|---|---|
| 43# | 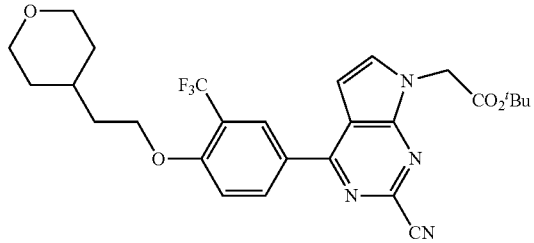 [SMILES: CC(C)(C)OC(=O)Cn1ccc2c(-c3ccc(OCCC4CCOCC4)c(C(F)(F)F)c3)nc(C#N)nc21] |
| 44 | 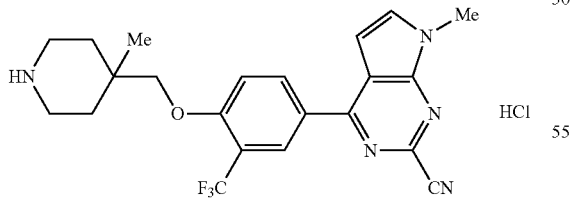 HCl |
| 45 | 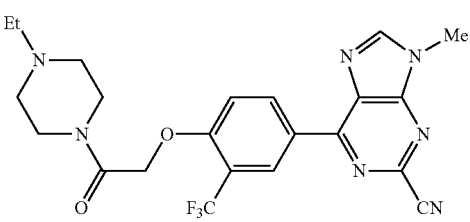 [SMILES: CCN1CCN(C(=O)COc2ccc(-c3nc(C#N)nc4c3ncn4C)cc2C(F)(F)F)CC1] |
TABLE 32-continued
| Ex | Str |
|---|---|
| 46# | 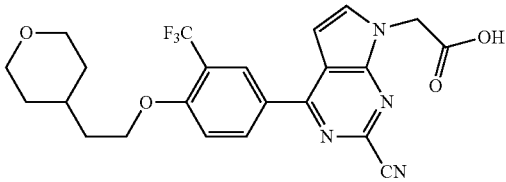 [SMILES: N#Cc1nc(-c2ccc(OCCC3CCOCC3)c(C(F)(F)F)c2)c2ccn(CC(=O)O)c2n1] |
| 47 | 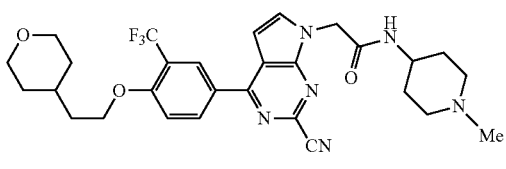 [SMILES: CN1CCC(NC(=O)Cn2ccc3c(-c4ccc(OCCC5CCOCC5)c(C(F)(F)F)c4)nc(C#N)nc32)CC1] |
| 48# | 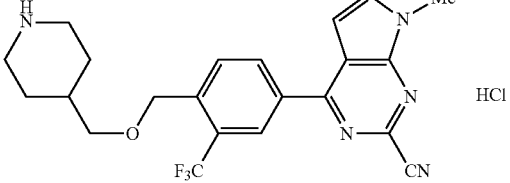 HCl |
| 49# | 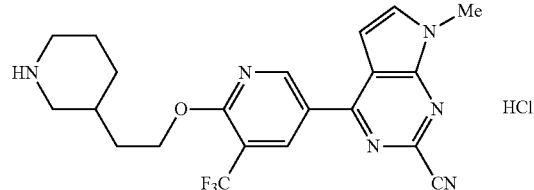 |
TABLE 33
| Ex | Str |
|---|---|
| 50 | 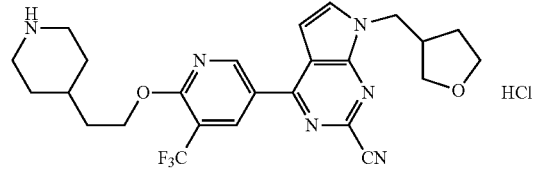 [SMILES: N#Cc1nc(-c2cnc(OCCC3CCNCC3)c(C(F)(F)F)c2)c2ccn(CC3CCOC3)c2n1 ; Cl] HCl |
| 51 |  HCl |
| 52 |  HCl |

TABLE 33-continued
| Ex | Str |
|---|---|
| 53# | 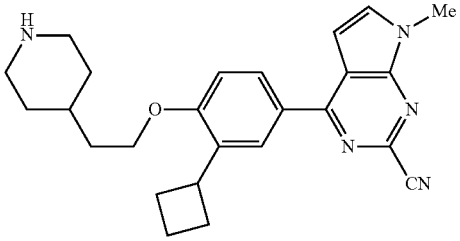 HCl |
| 54 | 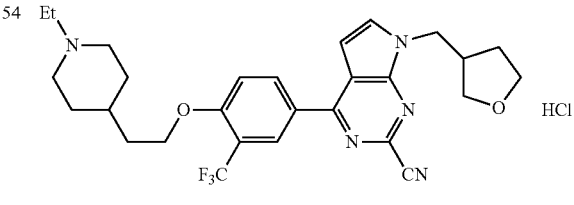 HCl |
| 55# | 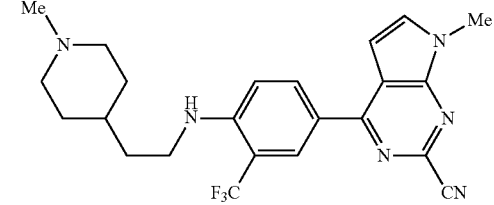 |
TABLE 34
| Ex | Str |
|---|---|
| 56 | 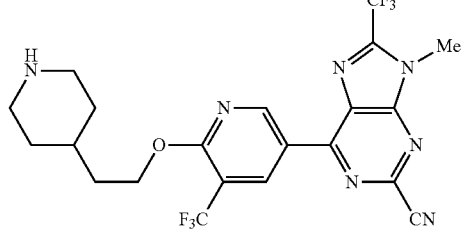 HCl |
| 57# | 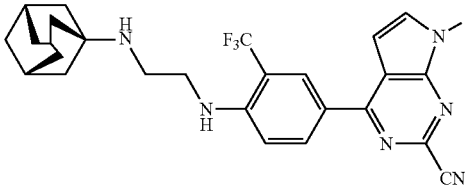 |
| 58 | 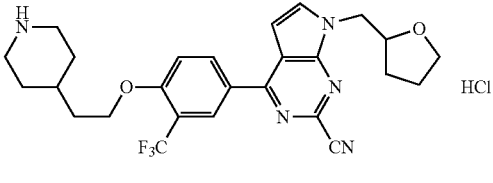 HCl |
| 59# | 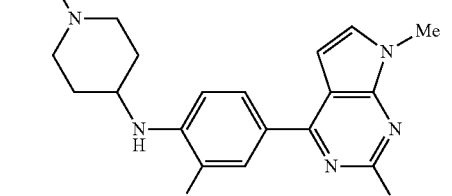 |
| 60# | 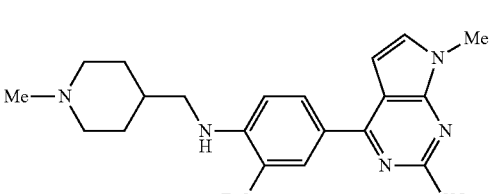 |
| 61# | 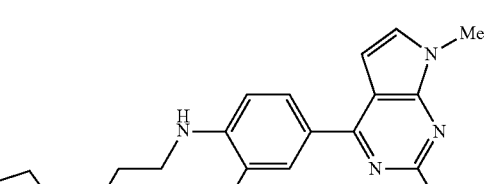 |
TABLE 35
| Ex | Str |
|---|---|
| 62# | 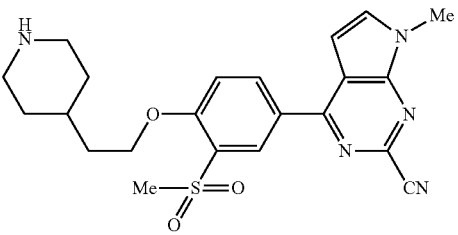 HCl |

TABLE 35-continued

| Ex | Str |
|---|---|
| 63# | (structure: pyrrolidine-C(Me)₂-CH₂-NH-phenyl(CF₃)-pyrrolo[2,3-d]pyrimidine-N-Me, 2-CN) |
| 64# | (structure: 1-methylpyrrolidin-2-yl-CH₂CH₂-NH-phenyl(CF₃)-pyrrolo[2,3-d]pyrimidine-N-Me, 2-CN) |
| 65 | (structure: HO-CH₂CH₂-N(piperidine)-CH₂CH₂-O-phenyl(CF₃)-pyrrolo[2,3-d]pyrimidine-N-CH₂-tetrahydrofuran-3-yl, 2-CN) HCl |
| 66 | (structure: (Me)₂N-C(O)-CH₂-N(piperidine)-CH₂CH₂-O-phenyl(CF₃)-pyrrolo[2,3-d]pyrimidine-N-CH₂-tetrahydrofuran-3-yl, 2-CN) HCl |
| 67# | (structure: N-methylpiperidine-CH₂CH₂-NH-phenyl(CF₃)-pyrrolo[2,3-d]pyrimidine-N-CH₂-tetrahydrofuran-3-yl, 2-CN) |

TABLE 36

| Ex | Str |
|---|---|
| 68 | (structure: piperidine-CH₂CH₂-O-phenyl(CF₃)-7H-pyrrolo[2,3-d]pyrimidine, 2-CN) HCl |

TABLE 36-continued
| Ex | Str |
|---|---|
| 69# | 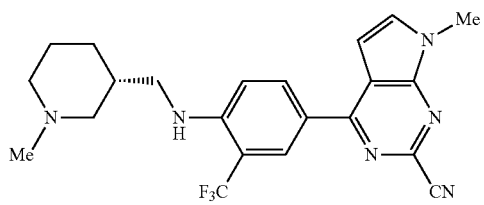 Chiral |
| 70 | 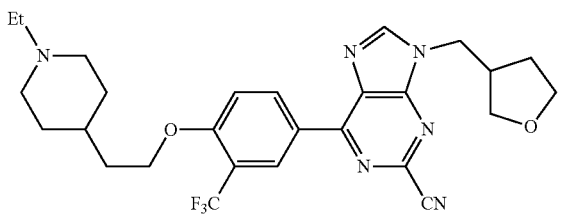 [SMILES: CCN1CCC(CCOc2ccc(-c3nc(C#N)nc4c3ncn4CC3CCOC3)cc2C(F)(F)F)CC1] |
| 71 | 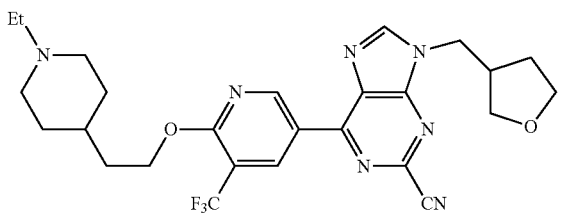 [SMILES: CCN1CCC(CCOc2ncc(-c3nc(C#N)nc4c3ncn4CC3CCOC3)cc2C(F)(F)F)CC1] |
| 72 | 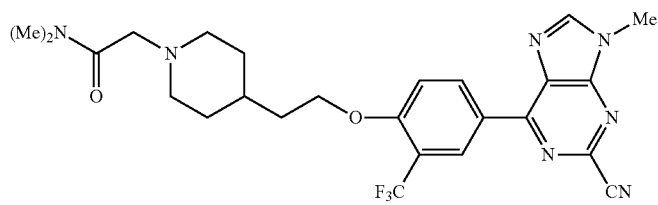 |
| 73 | 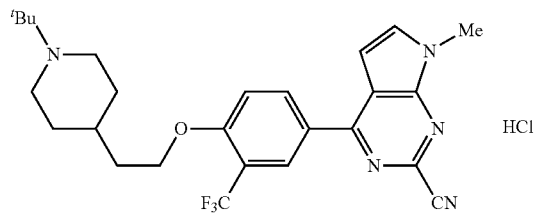 [SMILES: Cn1ccc2c(-c3ccc(OCCC4CCN(C(C)(C)C)CC4)c(C(F)(F)F)c3)nc(C#N)nc21 ; Cl] HCl |
| 74 | 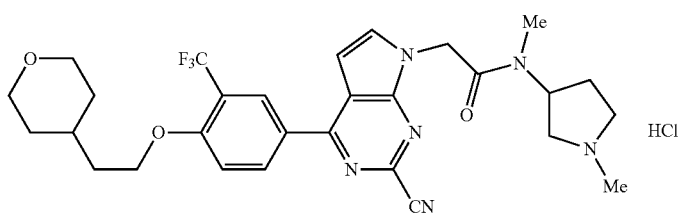 [SMILES: CN1CCC(N(C)C(=O)Cn2ccc3c(-c4ccc(OCCC5CCOCC5)c(C(F)(F)F)c4)nc(C#N)nc32)C1 ; Cl] HCl |

TABLE 37
| Ex | Str | |
|---|---|---|
| 75 | 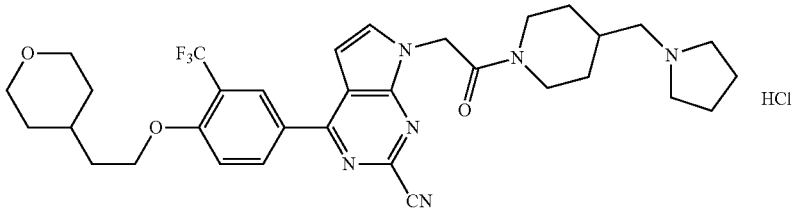 [SMILES: N#Cc1nc(-c2ccc(OCCC3CCOCC3)c(C(F)(F)F)c2)c2ccn(CC(=O)N3CCC(CN4CCCC4)CC3)c2n1 ; Cl] | HCl |
| 76 | 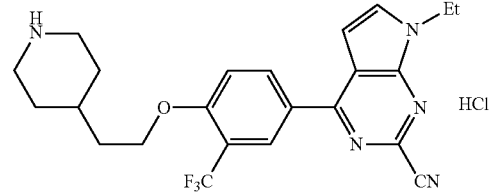 [SMILES: CCn1ccc2c(-c3ccc(OCCC4CCNCC4)c(C(F)(F)F)c3)nc(C#N)nc21 ; Cl] | HCl |
| 77 | 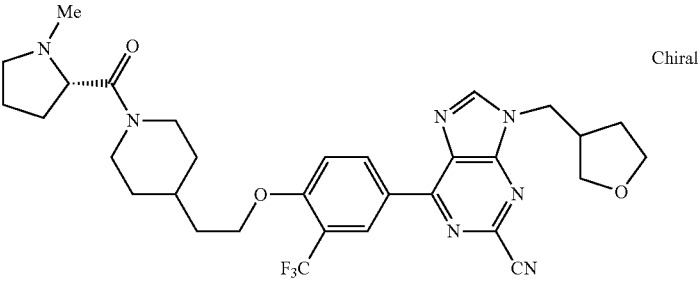 [SMILES: CN1CCC[C@H]1C(=O)N1CCC(CCOc2ccc(-c3nc(C#N)nc4c3ncn4CC3CCOC3)cc2C(F)(F)F)CC1] | Chiral |
| 78 | 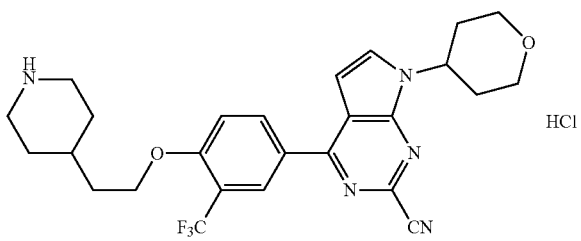 [SMILES: N#Cc1nc(-c2ccc(OCCC3CCNCC3)c(C(F)(F)F)c2)c2ccn(C3CCOCC3)c2n1 ; Cl] | HCl |
| 79 | 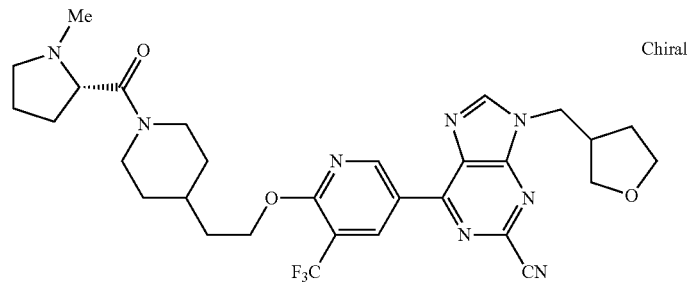 [SMILES: CN1CCC[C@H]1C(=O)N1CCC(CCOc2ncc(-c3nc(C#N)nc4c3ncn4CC3CCOC3)cc2C(F)(F)F)CC1] | Chiral |
| 80 | 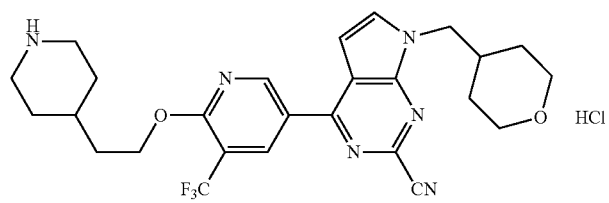 [SMILES: N#Cc1nc(-c2cnc(OCCC3CCNCC3)c(C(F)(F)F)c2)c2ccn(CC3CCOCC3)c2n1 ; Cl] | HCl |

TABLE 38
| Ex | Str |
|---|---|
| 81 | 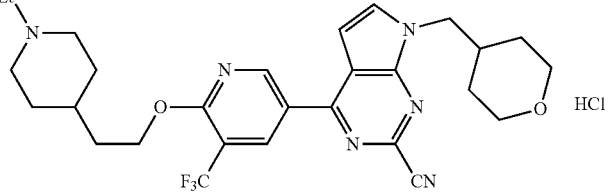 HCl |
| 82 | 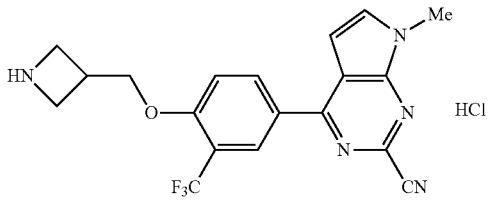 [SMILES: Cn1ccc2c(-c3ccc(OCC4CNC4)c(C(F)(F)F)c3)nc(C#N)nc21 ; Cl] HCl |
| 83 | 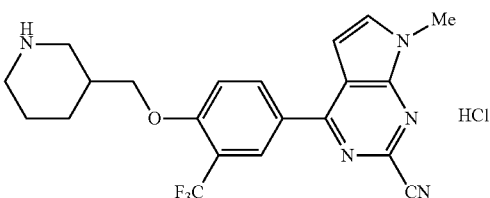 HCl |
| 84 | 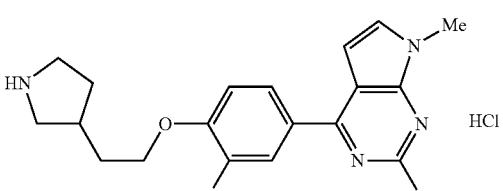 HCl |
| 85 | 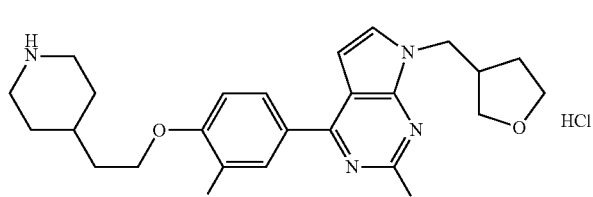 HCl |
| 86 | 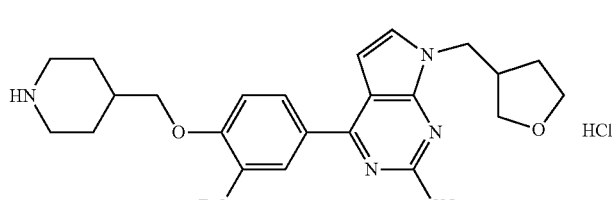 HCl |
| 87 | 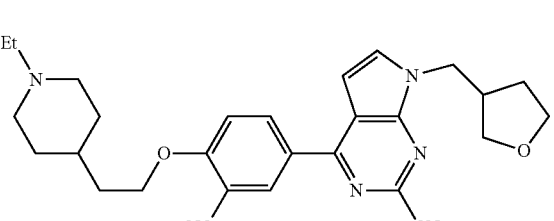 |

TABLE 39
| Ex | Str |
|---|---|
| 88 | 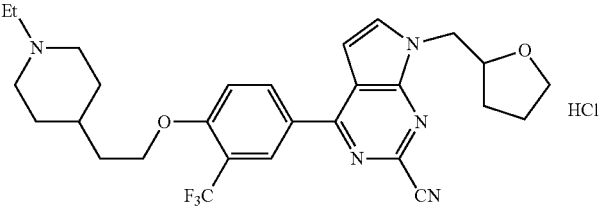 [SMILES: CCN1CCC(CCOc2ccc(-c3nc(C#N)nc4c3ccn4CC3CCCO3)cc2C(F)(F)F)CC1 ; Cl] HCl |
| 89 | 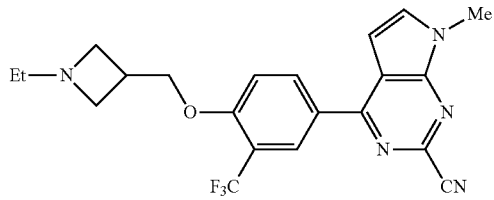 [SMILES: CCN1CC(COc2ccc(-c3nc(C#N)nc4c3ccn4C)cc2C(F)(F)F)C1] |
| 90 | 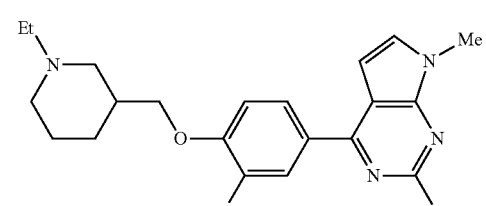 |
| 91 | 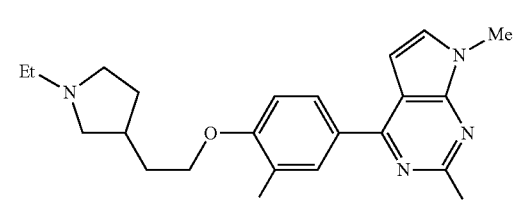 |
| 92 | 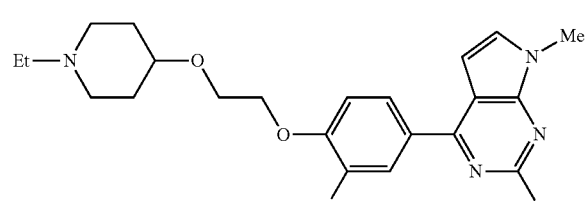 |
| 93 | 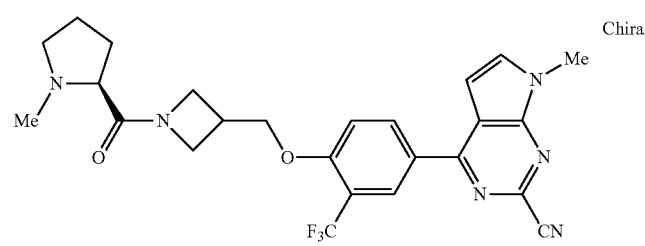 [SMILES: CN1CCC[C@H]1C(=O)N1CC(COc2ccc(-c3nc(C#N)nc4c3ccn4C)cc2C(F)(F)F)C1] Chiral |

TABLE 40
| Ex | Str |
|---|---|
| 94 | 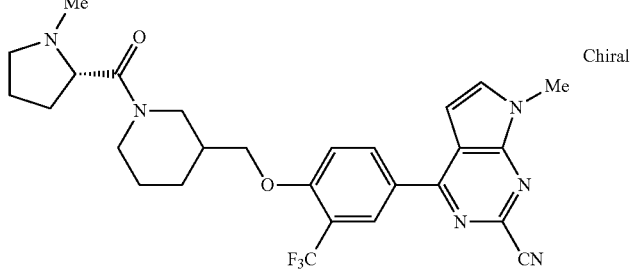 Chiral |
| 95 | 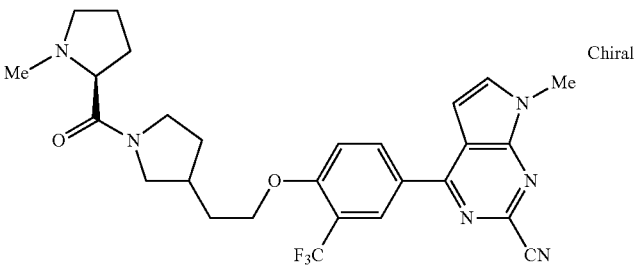 [SMILES: CN1CCC[C@H]1C(=O)N1CCC(CCOc2ccc(-c3nc(C#N)nc4c3ccn4C)cc2C(F)(F)F)C1] Chiral |
| 96 | 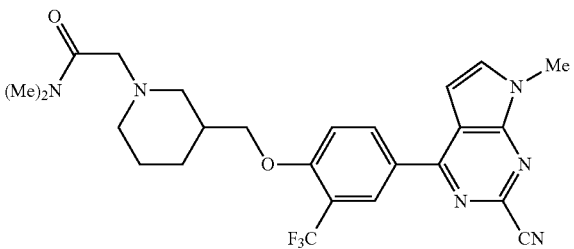 |
| 97 | 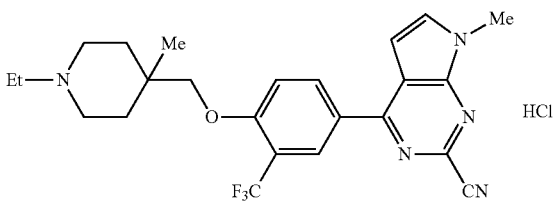 [SMILES: CCN1CCC(C)(COc2ccc(-c3nc(C#N)nc4c3ccn4C)cc2C(F)(F)F)CC1 ; Cl] HCl |
| 98# | 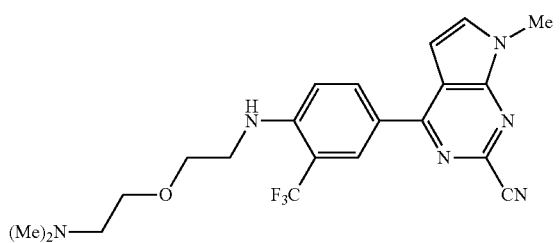 |
| 99# | 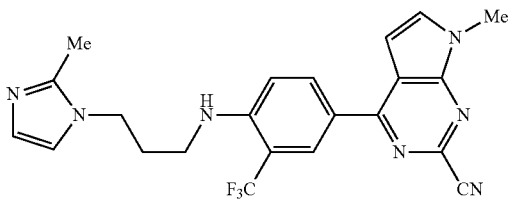 [SMILES: Cc1nccn1CCCNc1ccc(-c2nc(C#N)nc3c2ccn3C)cc1C(F)(F)F] |

TABLE 41

| Ex | Str |
|---|---|
| 100# | (structure) |
| 101 | (structure) HCl |
| 102 | (structure) |
| 103 | (structure) Fum |
| 104 | (structure) Chiral |
| 105 | (structure) Chiral |

TABLE 42
| Ex | Str | |
|---|---|---|
| 106 | 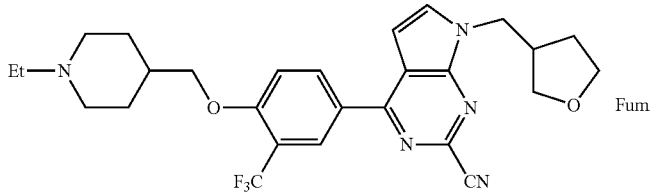 [SMILES: CCN1CCC(COc2ccc(-c3nc(C#N)nc4c3ccn4CC3CCOC3)cc2C(F)(F)F)CC1] | Fum |
| 107 | 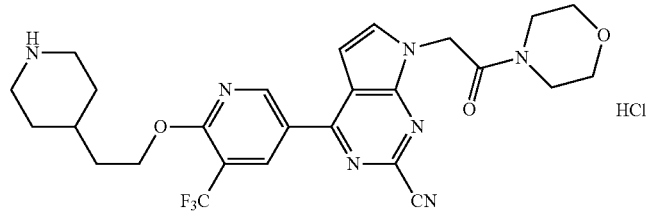 | HCl |
| 108 | 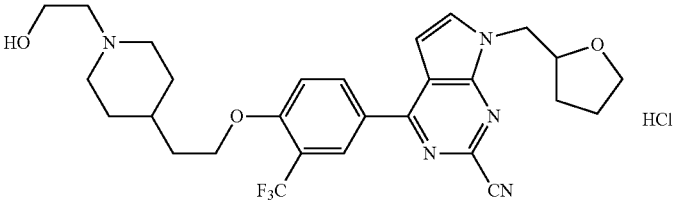 [SMILES: N#Cc1nc(-c2ccc(OCCC3CCN(CCO)CC3)c(C(F)(F)F)c2)c2ccn(CC3CCCO3)c2n1 ; Cl] | HCl |
| 109 | 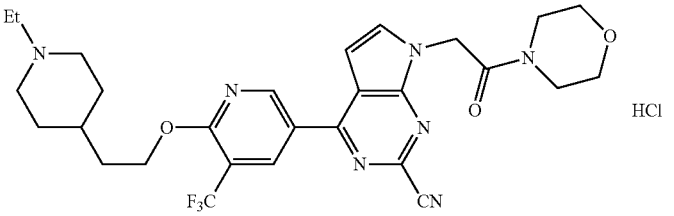 | HCl |
| 110 | 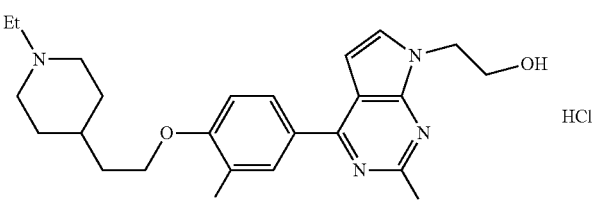 | HCl |
| 111 | 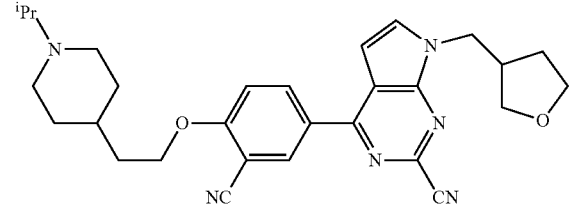 [SMILES: CC(C)N1CCC(CCOc2ccc(-c3nc(C#N)nc4c3ccn4CC3CCOC3)cc2C#N)CC1] | |

TABLE 43
| Ex | Str |
|---|---|
| 112 | 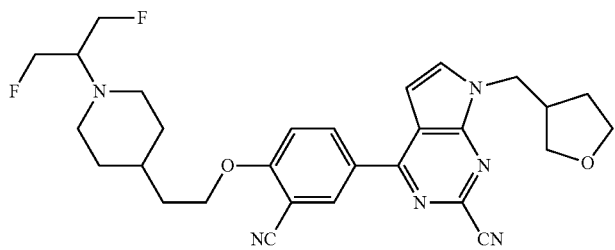 [SMILES: N#Cc1nc(-c2ccc(OCCC3CCN(C(CF)CF)CC3)c(C#N)c2)c2ccn(CC3CCOC3)c2n1] |
| 113 | 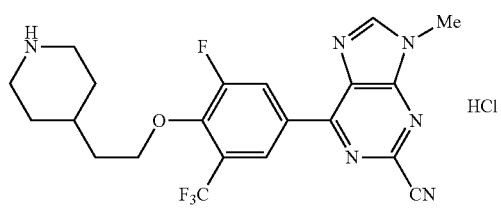 [SMILES: Cn1cnc2c(-c3cc(F)c(OCCC4CCNCC4)c(C(F)(F)F)c3)nc(C#N)nc21 ; Cl] HCl |
| 114 | 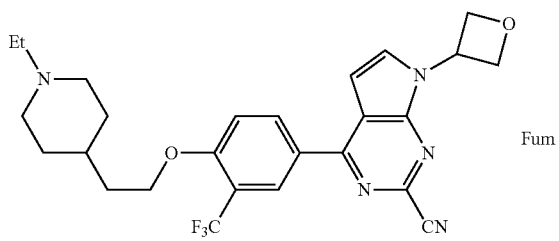 [SMILES: CCN1CCC(CCOc2ccc(-c3nc(C#N)nc4c3ccn4C3COC3)cc2C(F)(F)F)CC1 ; "Fum"] Fum |
| 115 | 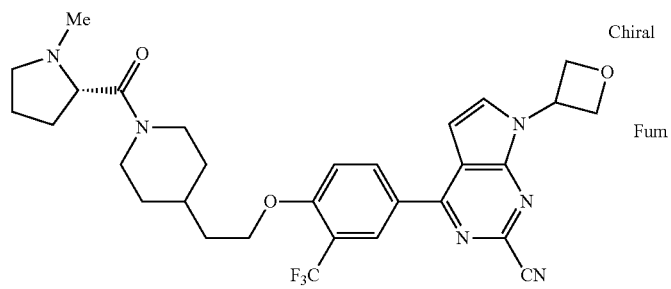 [SMILES: CN1CCC[C@H]1C(=O)N1CCC(CCOc2ccc(-c3nc(C#N)nc4c3ccn4C3COC3)cc2C(F)(F)F)CC1] Chiral Fum |
| 116 | 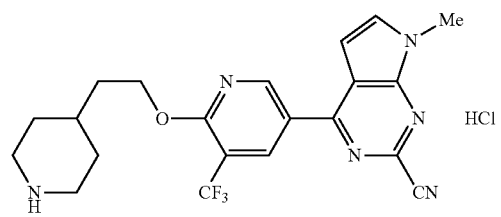 [SMILES: Cn1ccc2c(-c3cnc(OCCC4CCNCC4)c(C(F)(F)F)c3)nc(C#N)nc21 ; Cl] HCl |
| 117 | 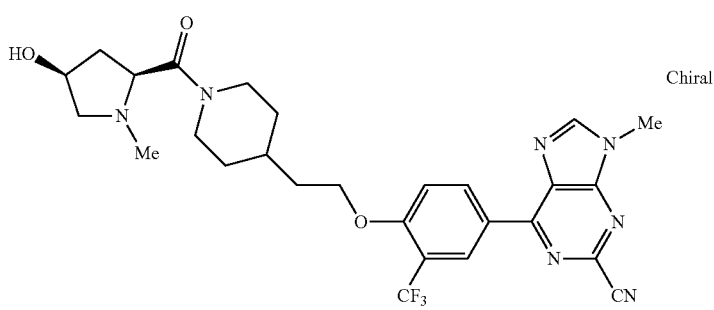 [SMILES: CN1C[C@@H](O)C[C@H]1C(=O)N1CCC(CCOc2ccc(-c3nc(C#N)nc4c3ncn4C)cc2C(F)(F)F)CC1] Chiral |

TABLE 44
| Ex | Str |
|---|---|
| 118 | 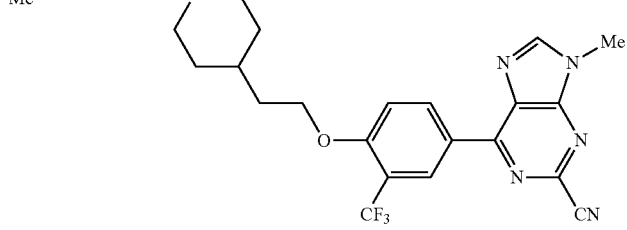 |
| 119 | 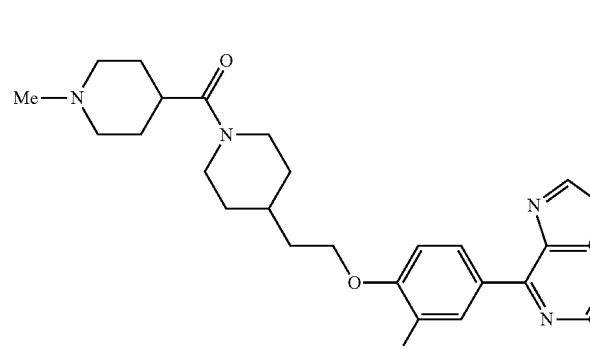 |
| 120 | 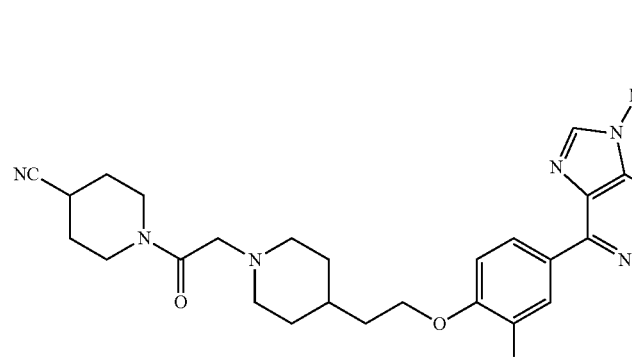 |
| 121 | 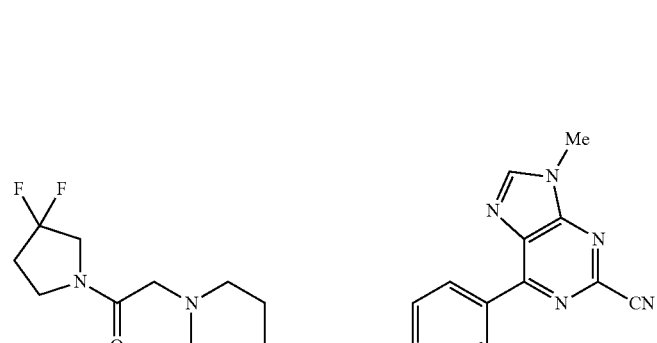 |

TABLE 45
| Ex | Str |
|---|---|
| 122 | 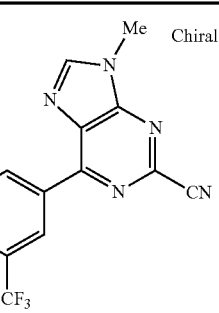 |
| 123 | 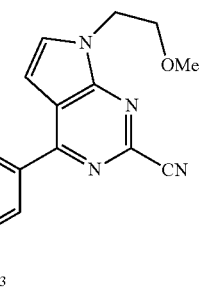 |
| 124 | 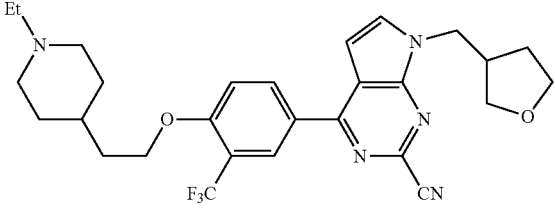 [SMILES: CCN1CCC(CCOc2ccc(-c3nc(C#N)nc4c3ccn4CC3CCOC3)cc2C(F)(F)F)CC1] |
| 125 | 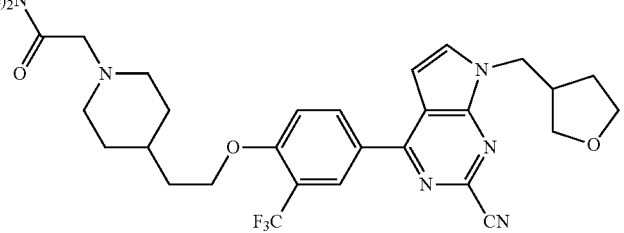 |
| 126 | 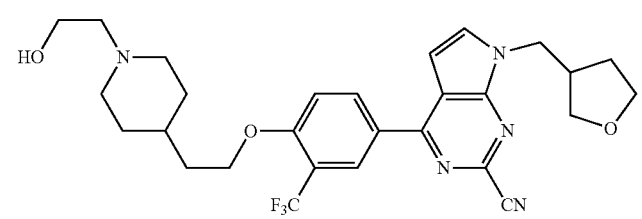 [SMILES: N#Cc1nc(-c2ccc(OCCC3CCN(CCO)CC3)c(C(F)(F)F)c2)c2ccn(CC3CCOC3)c2n1] |
| 127 | 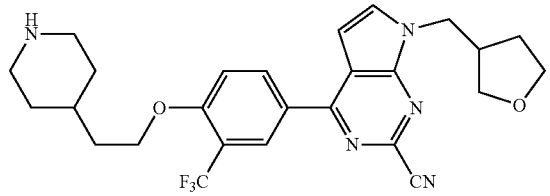 [SMILES: N#Cc1nc(-c2ccc(OCCC3CCNCC3)c(C(F)(F)F)c2)c2ccn(CC3CCOC3)c2n1] |

TABLE 46
| Ex | Str |
|---|---|
| 128 | 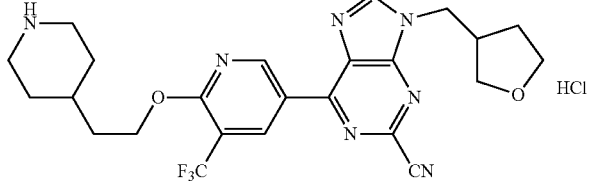 HCl |
| 129 | 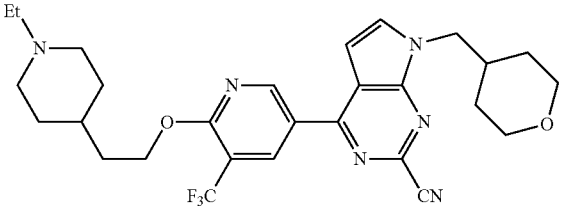 [SMILES: CCN1CCC(CCOc2ncc(-c3nc(C#N)nc4c3ccn4CC3CCOCC3)cc2C(F)(F)F)CC1] |
| 130 | 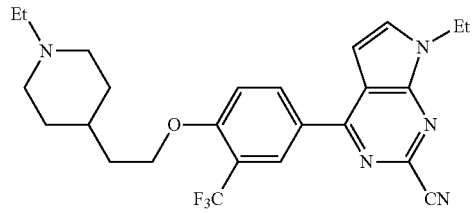 [SMILES: CCN1CCC(CCOc2ccc(-c3nc(C#N)nc4c3ccn4CC)cc2C(F)(F)F)CC1] |
| 131 | 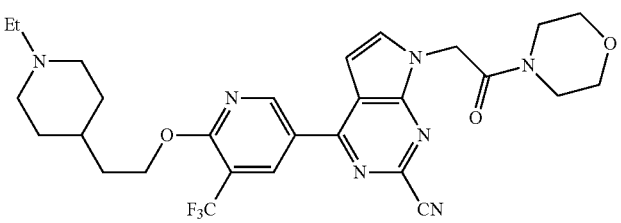 [SMILES: CCN1CCC(CCOc2ncc(-c3nc(C#N)nc4c3ccn4CC(=O)N3CCOCC3)cc2C(F)(F)F)CC1] |
| 132 | 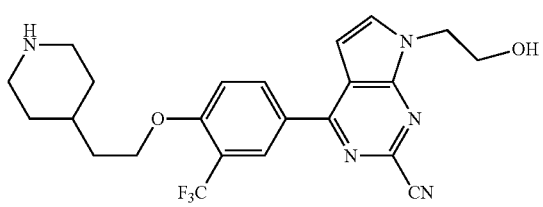 [SMILES: N#Cc1nc(-c2ccc(OCCC3CCNCC3)c(C(F)(F)F)c2)c2ccn(CCO)c2n1] |
| 133 | 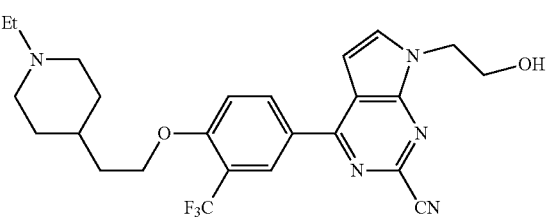 [SMILES: CCN1CCC(CCOc2ccc(-c3nc(C#N)nc4c3ccn4CCO)cc2C(F)(F)F)CC1] |

TABLE 47
| Ex | St |
|---|---|
| 134 | 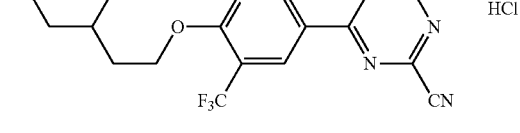 HCl |
| 135 | 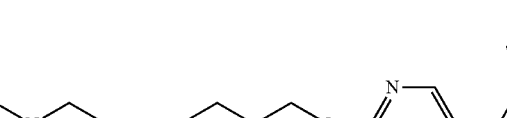 |
| 136 | 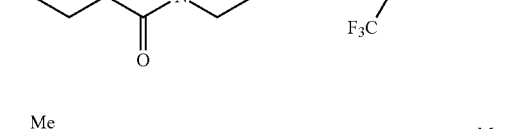 |
| 137 | 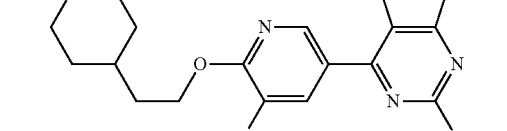 Chiral |
| 138 |  Chiral |
| 139 | 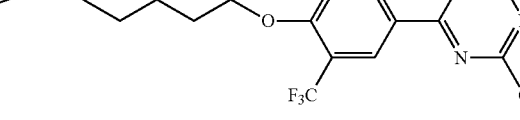 |

TABLE 48
| Ex | Str |
|---|---|
| 140 | 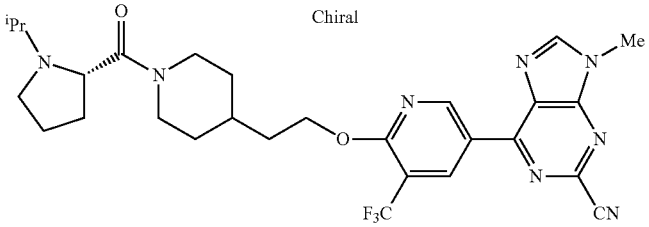 [SMILES: CC(C)N1CCC[C@H]1C(=O)N1CCC(CCOc2ncc(-c3nc(C#N)nc4c3ncn4C)cc2C(F)(F)F)CC1] Chiral |
| 141 | 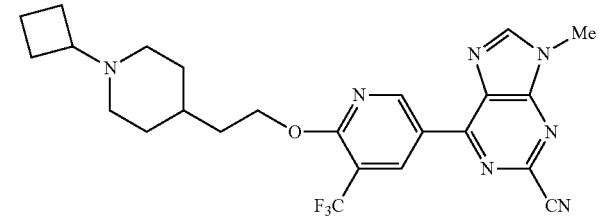 [SMILES: Cn1cnc2c(-c3cnc(OCCC4CCN(C5CCC5)CC4)c(C(F)(F)F)c3)nc(C#N)nc21] |
| 142 | 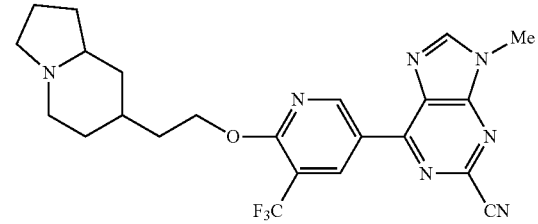 [SMILES: Cn1cnc2c(-c3cnc(OCCC4CCN5CCCC5C4)c(C(F)(F)F)c3)nc(C#N)nc21] |
| 143 | 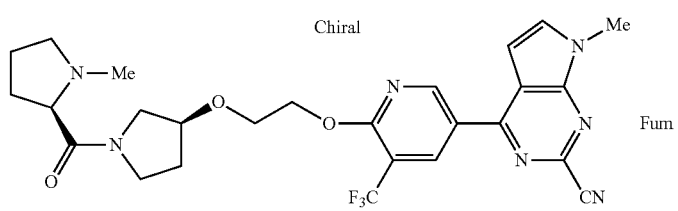 [SMILES: CN1CCC[C@@H]1C(=O)N1CC[C@H](OCCOc2ncc(-c3nc(C#N)nc4c3ccn4C)cc2C(F)(F)F)C1] Chiral, Fum |
| 144 | 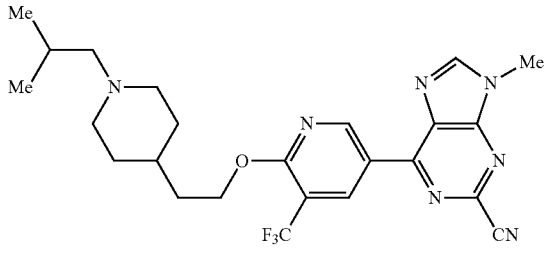 |
| 145 | 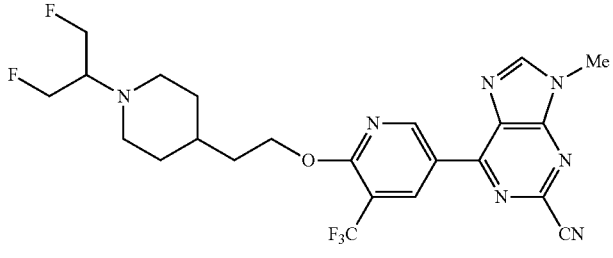 [SMILES: Cn1cnc2c(-c3cnc(OCCC4CCN(C(CF)CF)CC4)c(C(F)(F)F)c3)nc(C#N)nc21] |

TABLE 49
| Ex | Str |
|---|---|
| 146 | 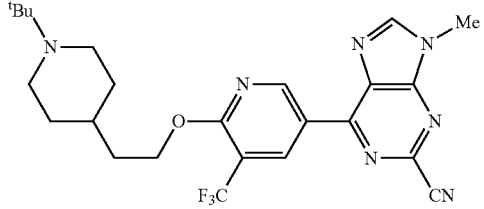 [SMILES: Cn1cnc2c(-c3cnc(OCCC4CCN(C(C)(C)C)CC4)c(C(F)(F)F)c3)nc(C#N)nc21] |
| 147 | 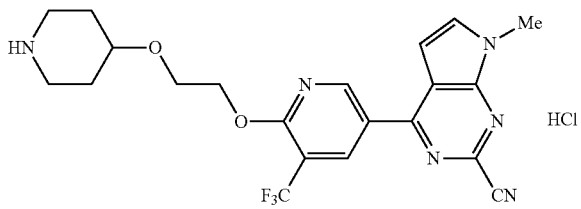 [SMILES: Cn1ccc2c(-c3cnc(OCCOC4CCNCC4)c(C(F)(F)F)c3)nc(C#N)nc21 ; Cl] HCl |
| 148 | 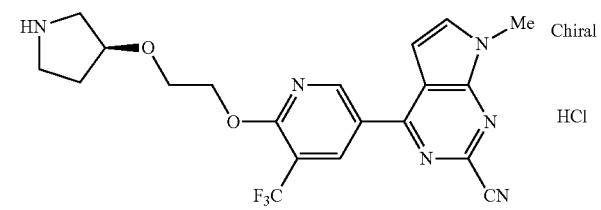 [SMILES: Cn1ccc2c(-c3cnc(OCCO[C@H]4CCNC4)c(C(F)(F)F)c3)nc(C#N)nc21 ; Cl] Chiral HCl |
| 149 | 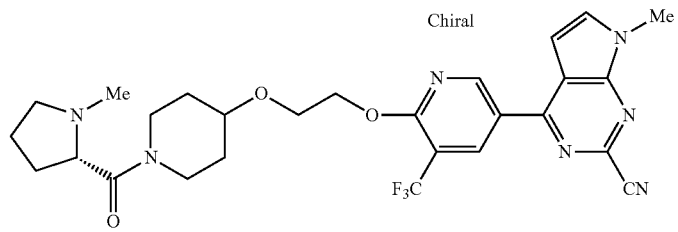 [SMILES: CN1CCC[C@H]1C(=O)N1CCC(OCCOc2ncc(-c3nc(C#N)nc4c3ccn4C)cc2C(F)(F)F)CC1] Chiral |
| 150 | 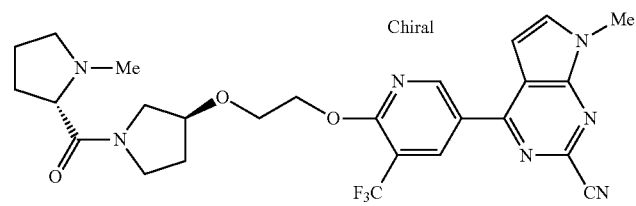 [SMILES: CN1CCC[C@H]1C(=O)N1CC[C@H](OCCOc2ncc(-c3nc(C#N)nc4c3ccn4C)cc2C(F)(F)F)C1] Chiral |
| 151 | 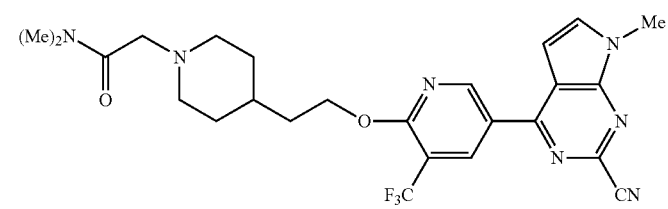 |

TABLE 50
| Ex | Str |
|---|---|
| 152 | 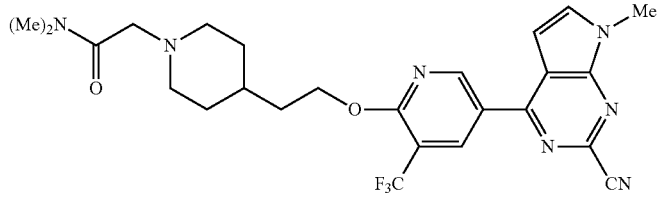 |
| 153 | 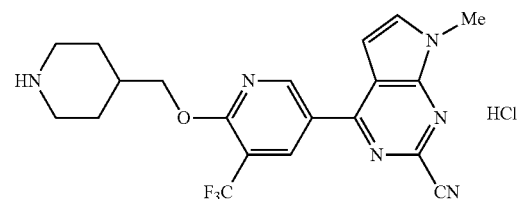 |
| 154 | 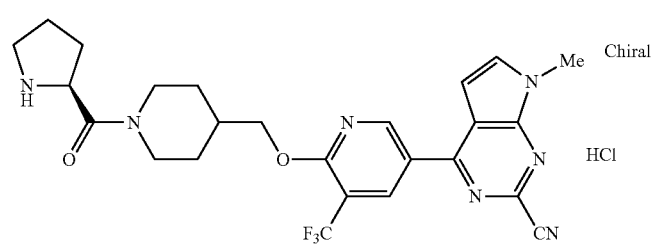 [SMILES: Cn1ccc2c(-c3cnc(OCC4CCN(C(=O)[C@@H]5CCCN5)CC4)c(C(F)(F)F)c3)nc(C#N)nc21 ; Cl] |
| 155 | 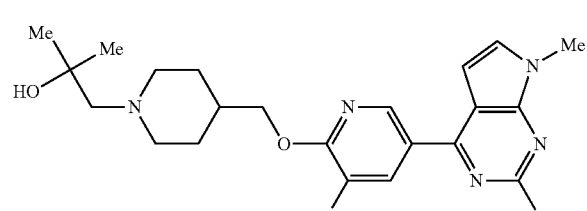 |
| 156 | 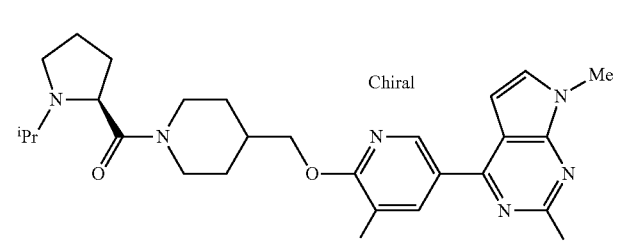 |
| 157 | 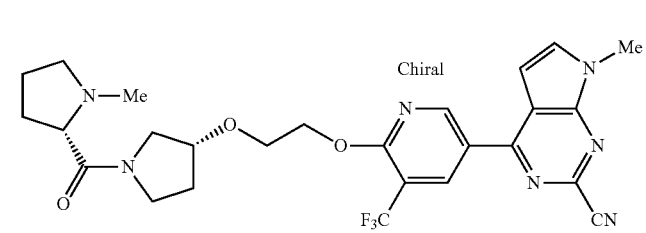 [SMILES: CN1CCC[C@H]1C(=O)N1CC[C@@H](OCCOc2ncc(-c3nc(C#N)nc4c3ccn4C)cc2C(F)(F)F)C1] |

TABLE 51

| Ex | Str |
|---|---|
| 158 | (Structure: N-methylpyrrolidine-carbonyl-pyrrolidinyl-O-ethyl-O-pyridine(CF3)-pyrrolopyrimidine-CN, N-Me on pyrrole; Chiral) |
| 159 | (Structure: piperidine-piperidinyl-carbonyl-piperidine-CH2-O-pyridine(CF3)-pyrrolopyrimidine-CN; HCl) |
| 160 | (Structure: tetrahydropyran-piperidinyl-piperidine-carbonyl-piperidine-CH2-O-pyridine(CF3)-pyrrolopyrimidine-CN) |

TABLE 52

| Ex | Syn | DAT |
|---|---|---|
| 1 | 1 | NMR1: 1.40(3H, t, J = 7.0 Hz), 3.92(3H, s), 4.31(2H, q, J = 7.0 Hz), 7.11(1H, d, J = 3.6 Hz), 7.48(1H, d, J = 8.8 Hz), 8.04(1H, d, J = 3.6 Hz), 8.38(1H, d, J = 2.2 Hz), 8.47(1H, dd, J = 2.2, 8.8 Hz); ESI+: 347 |
| 2 | 2 | NMR1: 1.33-1.49(2H, m), 1.73-1.94(5H, m), 2.77-2.90(2H, m), 3.21-3.31(2H, m), 3.93(3H, s), 4.27-4.36(2H, m), 7.11(1H, d, J = 3.6 Hz), 7.50(1H, d, J = 8.8 Hz), 8.06(1H, d, J = 3.6 Hz), 8.39(1H, d, J = 2.2 Hz), 8.48(1H, dd, J = 2.2, 8.8 Hz), 8.56(1H, br), 8.80(1H, br); ESI+: 430 |
| 3 | 3 | NMR2: 1.32-1.45 (2H, m), 1.54-1.67(1H, m), 1.69-1.78(2H, m), 1.79-1.87(2H, m), 2.03-2.15(2H, m), 2.89-2.93(2H, m), 2.95(3H, s), 3.09(3H, s), 3.15(2H, s), 3.96(3H, s), 4.17-4.24(2H, m), 6.90(1H, d, J = 3.6 Hz), 7.16(1H, d, J = 8.7 Hz), 7.47(1H, d, J = 3.6 Hz), 8.36(1H, dd, J = 2.2, 8.7 Hz), 8.41(1H, d, J = 2.2 Hz); ESI+: 515 |
| 4# | 4 | NMR2: 1.50(3H, t, J = 6.8 Hz), 4.22(2H, q, J = 6.8 Hz), 5.12(2H, s), 6.85-6.95(1H, m), 7.07-7.15(1H, m), 7.45-7.54(1H, m), 8.21-8.39(2H, m); ESI+: 391 |
| 5 | 5 | NMR2: 1.51(3H, t, J = 6.8 Hz), 2.36(3H, s), 2.45(2H, t, J = 4.8 Hz), 2.55(2H, t, J = 4.8 Hz), 3.64-3.71(4H, m), 4.25(2H, q, J = 6.8 Hz), 5.18(2H, s), 6.97(1H, d, J = 4 Hz), 7.17(1H, d, J = 8.8 Hz), 7.59(1H, d, J = 4 Hz), 8.35(1H, dd, J = 2.4, 8.8 Hz), 8.41(1H, d, J = 2.4 Hz); ESI+: 473 |
| 6 | 6 | NMR1: 0.97-1.22(2H, m), 1.59-1.85(8H, m), 1.97-2.04(1H, m), 2.10-2.24(4H, m), 2.44-2.60(1H, m), 2.87-3.02(2H, m), 3.02-3.17(1H, m), 3.92(3H, s), 4.10-4.46(4H, m), 7.56(1H, d, J = 9.0 Hz), 8.91(1H, s), 9.05(1H, dd, J = 2.1, 8.9 Hz), 9.16 (1H, d, J = 2.1 Hz); ESI+: 542 |
| 7 | 7 | NMR1: 1.09-1.25(2H, m), 1.60-1.81(5H, m), 2.59-2.69(2H, m), 2.71(6H, s), 3.48-3.59(2H, m), 3.92(3H, s), 4.32(2H, t, J = 6.2 Hz), 7.57(1H, d, J = 9.0 Hz), 8.92(1H, s), 9.06(1H, dd, J = 2.2, 8.9 Hz), 9.17(1H, d, J = 2.1 Hz); ESI+: 502 |
| 8 | 8 | NMR1: 1.20-1.31(2H, m), 1.61-1.68(2H, m), 1.72-1.82(3H, m), 2.74-2.84(2H, m), 2.94-3.71(10H, m), 3.82-3.88(2H, m), 4.09-4.46(3H, m), 5.47(2H, br-s), 7.16(1H, d, J = 3.6 Hz), 7.52(1H, d, J = 8.8 Hz), 7.92(1H, d, J = 3.6 Hz), 8.39(1H, d, J = 2.4 Hz), 8.49(1H, dd, J = 2.4, 8.8 Hz), 10.87(1H, br-s); ESI+: 557 |
| 9# | 9 | NMR1: 1.12-1.34(3H, m), 1.49-1.57(2H, m), 1.64-1.71(1H, m), 1.77-1.85(2H, m), 2.13(3H, s), 2.70-2.77(2H, m), 3.27-3.78(2H, m), 6.15(1H, t, J = 6 Hz), 7.00(1H, d, J = 8.8 Hz), 7.05(1H, d, J = 3.6 Hz), 7.93(1H, d, J = 3.6 Hz), 8.29-8.34(2H, m), 12.81(1H, br-s); ESI+: 429 |

TABLE 52-continued

| Ex | Syn | DAT |
|---|---|---|
| 10 | 10 | NMR1: 1.33-1.48(2H, m), 1.73-1.94(5H, m), 2.75(3H, s), 2.78-2.92(2H, m), 3.22-3.37(2H, m), 3.83 (3H, s), 4.26-4.35(2H, m), 7.55(1H, d, J = 8.9 Hz), 8.37(1H, br), 8.64(1H, br), 9.08(1H, dd, J = 2.2, 8.9 Hz), 9.11(1H, d, J = 2.2 Hz); ESI+: 445 |
| 11 | 11 | NMR2: 1.09(3H, t, J = 7.2 Hz), 1.29-1.42(2H, m), 1.55-1.68(1H, m), 1.72-1.96(6H, m), 2.40(2H, q, J = 7.2 Hz), 2.75(3H, s), 2.92-3.00(2H, m), 3.86(3H, s), 4.21(2H, t, J = 6.3 Hz), 7.14(1H, d, J = 8.8 Hz), 9.04(1H, dd, J = 2.2, 8.8 Hz), 9.16(1H, d, J = 2.2 Hz); ESI+: 473 |
| 12 | 12 | NMR1: 1.13-1.27(4H, m), 1.64-1.92(5H, m), 1.97-2.10(1H, m), 2.57-2.69(1H, m), 2.70-2.83(1H, m), 2.99-3.13(2H, m), 3.37-3.53 (2H, m), 3.94(3H, s), 4.53-4.71(2H, m), 7.23(1H, d, J = 3.6 Hz), 8.09(1H, d, J = 3.6 Hz), 8.73 (1H, d, J = 2.2 Hz), 9.25(1H, d, J = 2.2 Hz), 9.58(1H, br); ESI+: 459 |

TABLE 53

| Ex | Syn | DAT |
|---|---|---|
| 13 | 13 | NMR1: 1.23(3H, t, J = 7.3 Hz), 1.44-1.59(2H, m), 1.70-1.84(2H, m), 1.88-2.01(3H, m), 2.77-2.90(2H, m), 3.02-3.11(2H, m), 3.25(3H, s), 3.43-3.52(2H, m), 3.76(2H, t, J = 5.2 Hz), 4.29-4.36(2H, m), 4.53(2H, t, J = 5.2 Hz), 7.12(1H, d, J = 3.6 Hz), 7.51(1H, d, J = 8.8 Hz), 8.07 (1H, d, J = 3.6 Hz), 8.39(1H, d, J = 3.6 Hz), 8.48(1H, dd, J = 2.1, 8.8 Hz), 9.68(1H, br); ESI+: 502 |
| 14 | 14 | NMR1: 0.22-0.30(2H, m), 0.35-0.42(2H, m), 1.06-1.22(2H, m), 1.44-1.60(2H, m), 1.62-1.76(4H, m), 2.04-2.16(2H, m), 2.87-2.96(2H, m), 3.92(3H, s), 4.28(2H, t, J = 6.4 Hz), 7.11(1H, d, J = 3.6 Hz), 7.50(1H, d, J = 8.9 Hz), 8.04(1H, d, J = 3.6 Hz), 8.38(1H, d, J = 2.2 Hz), 8.46(1H, dd, J = 2.2, 8.8 Hz); ESI+: 470 |
| 15 | 15 | NMR1: 1.06-1.34(4H, m), 1.54-1.67(1H, m), 1.72-2.16(5H, m), 2.45-2.56(4H, m), 2.65-2.83(4H, m), 3.01-3.15(2H, m), 3.54-3.73(3H, m), 3.75-3.84(1H, m), 4.20-4.66(8H, m), 7.12(1H, d, J = 3.6 Hz), 7.52(1H, d, J = 8.8 Hz), 8.06(1H, d, J = 3.7 Hz), 8.39(1H, d, J = 2.2 Hz), 8.48(1H, dd, J = 2.2, 8.8 Hz), 9.43-9.60(1H, br); ESI+: 611 |
| 16 | 16 | NMR1: 1.50-1.68(3H, m), 1.71-2.05(8H, m), 2.86-3.05(8H, m), 3.43-3.54(2H, m), 3.60-3.69(1H, m), 3.75-3.83(1H, m), 4.16-4.49(7H, m), 7.12(1H, d, J = 3.6 Hz), 7.51(1H, d, J = 8.9 Hz), 8.06(1H, d, J = 3.6 Hz), 8.39(1H, d, J = 2.2 Hz), 8.49(1H, dd, J = 2.1, 8.7 Hz), 9.31-9.48(1H, br); ESI+: 585 |
| 17# | 17 | NMR1: 1.48-1.61(1H, m), 1.63-1.78(2H, m), 2.03-2.17(1H, m), 2.23-2.37(1H, m), 2.55(3H, s), 2.85-3.02(2H, m), 3.10-3.20(1H, m), 3.27-3.38(3H, m), 3.90(3H, s), 6.26-6.33(1H, m), 6.54(2H, s), 7.01-7.06(1H, m), 7.07(1H, d, J = 3.6 Hz), 7.96(1H, d, J = 3.6 Hz), 8.28-8.34(2H, m); ESI+: 429 |
| 18 | 18 | ESI+: 460 |
| 19 | 2 | NMR1: 1.33-1.48(2H, m), 1.71-1.95(5H, m), 2.76-2.91(2H, m), 3.20-3.38(2H, m), 3.93(3H, s), 4.27-4.38(2H, m), 7.56(1H, d, J = 9.0 Hz), 8.49(1H, br), 8.73(1H, br), 8.92(1H, s), 9.06(1H, dd, J = 2.2, 9.0 Hz), 9.17(1H, d, J = 2.2 Hz); ESI+: 431 |
| 20 | 1 | NMR2: 1.51(3H, t, J = 7.0 Hz), 3.98(3H, s), 4.25(2H, q, J = 7.0 Hz), 7.16(1H, d, J = 8.8 Hz), 8.25(1H, s), 9.06(1H, dd, J = 2.2, 8.8 Hz), 9.21(1H, d, J = 2.2 Hz); ESI+: 348 |
| 21 | 3 | NMR2: 1.32-1.44(2H, m), 1.52-1.67(1H, m), 1.69-1.86(4H, m), 2.04-2.14(2H, m), 2.88-2.92(2H, m), 2.94(3H, s), 3.08(3H, s), 3.15(2H, s), 4.07(2H, t, J = 5.0 Hz), 4.20(2H, t, J = 6.4 Hz), 4.51(2H, t, J = 5.0 Hz), 6.91(1H, d, J = 3.6 Hz), 7.16(1H, d, J = 8.8 Hz), 7.63 (1H, d, J = 3.6 Hz), 8.35(1H, dd, J = 2.2, 8.8 Hz), 8.40(1H, d, J = 2.2 Hz); ESI+: 545 |
| 22# | 1 | NMR2: 1.50(9H, s), 1.51(3H, t, J = 7.0 Hz), 4.25(2H, q, J = 7.0 Hz), 5.01(2H, s), 6.96 (1H, d, J = 3.6 Hz), 7.17(1H, d, J = 8.4 Hz), 7.53(1H, d, J = 3.6 Hz), 8.35(1H, dd, J = 2.4, 8.4 Hz), 8.41(1H, d, J = 2.4 Hz); ESI+: 447 |
| 23 | 10 | NMR1: 1.34-1.49(2H, m), 1.59-1.69(1H, m), 1.73-1.97(6H, m), 2.78-2.93(3H, m), 3.21-3.32(2H, m), 3.49-3.55(1H, m), 3.61-3.69(2H, m), 3.79-3.86(1H, m), 4.27-4.38(4H, m), 7.14(1H, d, J = 3.6 Hz), 7.50(1H, d, J = 8.8 Hz), 8.16(1H, d, J = 3.6 Hz), 8.38(1H, d, J = 2.2 Hz), 8.40-8.56(2H, m), 8.73(1H, br); ESI+: 500 |
| 24 | 3 | NMR1: 1.16-1.30(2H, m), 1.44-1.57(1H, m), 1.64-1.76(4H, m), 1.86-2.01(2H, m), 2.31-2.42(2H, m), 2.78-2.95(2H, m), 3.44-3.52(2H, m), 3.92(3H, s), 4.24-4.39(3H, m), 7.56(1H, d, J = 9.0 Hz), 8.91(1H, s), 9.05(1H, dd, J = 2.2, 8.9 Hz), 9.17 (1H, d, J = 2.1 Hz); ESI+: 475 |

TABLE 54

| Ex | Syn | DAT |
|---|---|---|
| 25 | 3 | NMR1: 1.14-1.31(2H, m), 1.42-1.56(1H, m), 1.64-1.79(6H, m), 1.80-1.88(2H, m), 1.96-2.06(2H, m), 2.79-2.89(2H, m), 3.04(2H, s), 3.23-3.33(2H, m), 3.46(2H, t, J = 6.7 Hz), 3.92(3H, s), 4.30(2H, t, J = 6.5 Hz), 7.56(1H, d, J = 9.0 Hz), 8.92(1H, s), 9.05(1H, dd, J = 2.2, 8.9 Hz), 9.17(1H, d, J = 2.2 Hz); ESI+: 542 |
| 26 | 11 | NMR1 : 0.98(3H, t, J = 7.2 Hz), 1.12-1.29(2H, m), 1.42-1.58(1H, m), 1.64-1.88(6H, m), 2.28(2H, q, J = 7.2 Hz), 2.79-2.91(2H, m), 3.92(3H, s), 4.30(2H, t, J = 6.4 Hz), 7.56(1H, d, J = 9.0 Hz), 8.91(1H, s), 9.05(1H, dd, J = 2.2, 8.9 Hz), 9.16(1H, d, J = 2.1 Hz); ESI+: 459 |
| 27 | 11 | NMR1: 0.99(3H, t, J = 7.2 Hz), 1.13-1.31(3H, m), 1.41-1.55(1H, m), 1.63-1.96(5H, m), 2.25-2.39(2H, m), 2.81-2.94(2H, m), 3.93(3H, s), 4.59(2H, t, J = 6.5 Hz), 7.24(1H, d, J = 3.6 Hz), 8.07(1H, d, J = 3.6 Hz), 8.71(1H, d, J = 2.0 Hz), 9.23(1H, d, J = 2.0 Hz); ESI+: 459 |
| 28 | 28 | NMR1: 1.33-1.49(2H, m), 1.69-1.83(3H, m), 1.84-1.93(2H, m), 2.75-2.90(2H, m), 3.20-3.32(2H, m), 3.94(3H, s), 4.61(2H, t, J = 6.1 Hz), 8.53 (1H, br), 8.79(1H, br), 8.97(1H, s), 9.33(1H, d, J = 2.2 Hz), 9.75(1H, d, J = 2.2 Hz); ESI+: 432 |
| 29 | 6 | NMR1: 0.95-1.21(2H, m), 1.60-1.84(8H, m), 1.98-2.10(1H, m), 2.15-2.24(4H, m), 2.45-2.58(1H, m), 2.88-3.02(2H, m), 3.04-3.18(1H, m), 3.92(3H, s), 4.09-4.45(4H, m), 7.56(1H, d, J = 9.0 Hz), 8.91(1H, s), 9.05(1H, dd, J = 2.2, 8.9 Hz), 9.16 (1H, d, J = 2.1 Hz); ESI+: 542 |
| 30 | 6 | NMR2: 1.10-1.33(2H, m), 1.66-2.15(11H, m), 2.17-2.29(1H, m), 2.31-2.39(3H, m), 2.53-2.66(1H, m), 2.88-3.09(3H, m), 3.13-3.21(1H, m), 3.61-3.67(1H, m), 3.75-3.84(2H, m), 3.95-4.02(1H, m), 4.07-4.43(5H, m), 4.62-4.73(1H, m), 6.91(1H, d, J = 3.6 Hz), 7.18(1H, d, J = 8.7 Hz), 7.50(1H, d, J = 3.6 Hz), 8.37(1H, dd, J = 2.2, 8.7 Hz), 8.41(1H, d, J = 2.2 Hz); ESI+: 611 |
| 31 | 3 | NMR1: 1.20-1.32(2H, m), 1.43-1.58(1H, m), 1.68-1.80(4H, m), 2.07-2.18(2H, m), 2.74-2.83(2H, m), 3.69(2H, s), 3.92(3H, s), 4.31(2H, t, J = 6.4 Hz), 7.56(1H, d, J = 9.0 Hz), 8.91(1H, s), 9.05(1H, dd, J = 2.2, 8.9 Hz), 9.17(1H, d, J = 2.1 Hz); ESI+: 470 |
| 32 | 3 | NMR1: 1.17-1.30(2H, m), 1.42-1.55(1H, m), 1.66-1.77(4H, m), 2.02-2.12(2H, m), 2.48(3H, s), 2.79-2.86(2H, m), 3.71(2H, s), 3.92(3H, s), 4.29(2H, t, J = 6.4 Hz), 7.55(1H, d, J = 9.0 Hz), 8.91(1H, s), 9.04(1H, dd, J = 2.2, 8.9 Hz), 9.16(1H, d, J = 2.2 Hz); ESI+: 527 |
| 33 | 6 | NMR1: 1.00-1.26(2H, m), 1.70-1.83(5H, m), 2.53-2.68(1H, m), 2.85-2.98(1H, m), 3.60-3.73(1H, m), 3.92(3H, s), 4.01-4.13(2H, m), 4.26-4.39(3H, m), 4.42(1H, t, J = 5.4 Hz), 7.56(1H, d, J = 9.0 Hz), 8.91(1H, s), 9.05(1H, dd, J = 2.2, 8.9 Hz), 9.16(1H, d, J = 2.2 Hz); ESI+: 489 |
| 34 | 2 | NMR1: 1.26-1.42(2H, m), 1.57-1.81(3H, m), 1.83-1.95(2H, m), 2.76-2.94(2H, m), 3.14-3.29(4H, m), 3.94(3H, s), 7.13(1H, d, J = 4 Hz), 7.84(1H, d, J = 9.0 Hz), 8.08(1H, d, J = 4 Hz), 8.35-8.48(3H, m), 8.62-8.8(1H, br); ESI+: 446 |
| 35 | 2 | NMR1: 1.66-1.77(2H, m), 1.90-2.00(2H, m), 2.91-3.03(2H, m), 3.06-3.18(2H, m), 3.65-3.73(1H, m), 3.80-3.87(2H, m), 3.93(3H, s), 4.36-4.43 (2H, m), 7.12(1H, d, J = 3.6 Hz), 7.52(1H, d, J = 8.8 Hz), 8.06(1H, d, J = 3.6 Hz), 8.40(1H, d, J = 2.2 Hz), 8.49(1H, dd, J = 2.2, 8.8 Hz), 8.57(1H, br), 8.66(1H, br); ESI+: 446 |

TABLE 55

| Ex | Syn | DAT |
|---|---|---|
| 36 | 2 | NMR1: 3.02-3.26(4H, m), 3.64-3.73(4H, m), 3.93(3H, s), 5.27(2H, s), 7.44(1H, d, J = 9.0 Hz), 8.93(1H, s), 8.99(1H, dd, J = 2.2, 9.0 Hz), 9.11(2H, br), 9.18(1H, d, J = 2.2 Hz); ESI+: 446 |
| 37 | 2 | NMR1: 1.55-1.83(4H, m), 1.89-2.25(7H, m), 3.88-3.98(5H, m), 4.24-4.36(2H, m), 7.10-7.13(1H, m), 7.47-7.52(1H, m), 8.04-8.07(1H, m), 8.37-8.40(1H, m), 8.46-8.52(1H, m), 8.55-8.97(2H, m); ESI+: 456 |
| 38 | 2 | NMR1: 1.63-2.04(6H, m), 2.11-2.26(3H, m), 2.81-2.97(2H, m), 3.02-3.12(1H, m), 3.13-3.24(1H, m), 3.93(3H, s), 4.25-4.41(2H, m), 7.11(1H, d, J = 3.6 Hz), 7.52(1H, d, J = 8.8 Hz), 8.06(1H, d, J = 3.6 Hz), 8.33-8.55(3H, m), 8.92-9.03(1H, m); ESI+: 456 |
| 39 | 39 | NMR1: 0.97(3H, t, J = 7.2 Hz), 1.13-1.26(2H, m), 1.38-1.53(1H, m), 1.64-1.85(6H, m), 2.27(2H, q, J = 7.2 Hz), 2.79-2.88(2H, m), 3.94(3H, s), 4.60(2H, t, J = 6.6 Hz), 8.96(1H, s), 9.33(1H, d, J = 2.2 Hz), 9.76(1H, d, J = 2.2 Hz); ESI+: 460 |
| 40 | 6 | NMR1: 0.96-1.21(2H, m), 1.58-1.82(8H, m), 1.97-2.08(1H, m), 2.11-2.23(4H, m), 2.48-2.59(1H, m), 2.88-3.00(2H, m), 3.03-3.16(1H, m), 3.94(3H, s), 4.10-4.27(1H, m), 4.31-4.47(1H, m), 4.57-4.65(2H, m), 8.96(1H, s), 9.31(1H, d, J = 2.1 Hz), 9.74(1H, d, J = 2.1 Hz); ESI+: 543 |
| 41 | 6 | NMR1: 0.96-1.23(2H, m), 1.59-1.83(8H, m), 1.97-2.08(1H, m), 2.11-2.23(4H, m), 2.45-2.59(1H, m), 2.87-3.01(2H, m), 3.02-3.15(1H, m), 3.93(3H, s), 4.11-4.26(1H, m), 4.31-4.45(1H, m), 4.60(2H, t, J = 6.1 Hz), 7.23(1H, d, J = 3.6 Hz), 8.07(1H, d, J = 3.6 Hz), 8.71(1H, d, J = 2.2 Hz), 9.23(1H, d, J = 2.2 Hz); ESI+: 542 |

TABLE 55-continued

| Ex | Syn | DAT |
|---|---|---|
| 42 | 5 | NMR1: 1.40(3H, t, J = 7.0 Hz), 1.46-1.52(2H, m), 1.72-1.81(2H, m), 1.91-2.26(5H, m), 2.69-2.83(2H, m), 3.48-3.61(1H, m), 4.32(2H, q, J = 7.0 Hz), 5.03(2H, s), 7.13(1H, d, J = 3.7 Hz), 7.50(1H, d, J = 8.8 Hz), 8.02(1H, d, J = 3.7 Hz), 8.34(1H, d, J = 7.5 Hz), 8.39(1H, d, J = 2.2 Hz), 8.48 (1H, dd, J = 2.2, 8.8 Hz); ESI+: 487 |
| 43# | 1 | NMR1: 1.20-1.31(2H, m), 1.44(9H, s), 1.61-1.67(2H, m), 1.72-1.82(3H, m), 3.24-3.33(2H, m), 3.82-3.88(2H, m), 4.31(2H, t, J = 6 Hz), 5.18(2H, s), 7.16(1H, d, J = 3.6 Hz), 7.52(1H, d, J = 8.8 Hz), 8.05(1H, d, J = 3.6 Hz), 8.39(1H, d, J = 2.2 Hz), 8.48(1H, dd, J = 2.2, 8.8 Hz); ESI+: 531 |
| 44 | 2 | NMR1: 1.16(3H, s), 1.58-1.69(2H, m), 1.74-1.85(2H, m), 3.04-3.23(4H, m), 3.93(3H, s), 4.09(2H, s), 7.11(1H, d, J = 3.6 Hz), 7.52(1H, d, J = 8.8 Hz), 8.06(1H, d, J = 3.6 Hz), 8.39(1H, d, J = 2.2 Hz), 8.49(1H, dd, J = 2.2, 8.8 Hz), 8.55-8.80(2H, m); ESI+: 430 |
| 45 | 11 | NMR1: 1.01(3H, t, J = 7.2 Hz), 2.29-2.45(6H, m), 3.41-3.51(4H, m), 3.92(3H, s), 5.20(2H, s), 7.39(1H, d, J = 9.0 Hz), 8.92(1H, s), 8.99(1H, dd, J = 2.1, 9.0 Hz), 9.18(1H, d, J = 2.1 Hz); ESI+: 474 |
| 46# | 4 | NMR1: 1.20-1.31(2H, m), 1.61-1.68(2H, m), 1.71-1.82(3H, m), 3.12-3.49(2H, m), 3.80-3.89(2H, m), 4.31(2H, t, J = 6.0 Hz), 5.16(2H, s), 7.15(1H, d, J = 3.6 Hz), 7.52(1H, d, J = 8.8 Hz), 8.05(1H, d, J = 3.6 Hz), 8.38(1H, d, J = 2.4 Hz), 8.48(1H, dd, J = 2.4, 8.8 Hz), 13.37(1H, br); ESI+: 475 |

TABLE 56

| Ex | Syn | DAT |
|---|---|---|
| 47 | 5 | NMR1: 1.20-1.31(2H, m), 1.40-1.52(2H, m), 1.60-1.67(2H, m), 1.70-1.83(5H, m), 1.89-1.98(2H, m), 2.14(3H, s), 2.66-2.73 (2H, m), 3.28(2H, dt, J = 1.6, 11.6 Hz), 3.46-3.57(1H, m), 3.82-3.88(2H, m), 4.31(2H, t, J = 6.0 Hz), 5.03(2H, s), 7.12(1H, d, J = 3.6 Hz), 7.51(1H, d, J = 8.8 Hz), 8.02(1H, d, J = 3.6 Hz), 8.32(1H, d, J = 7.6 Hz), 8.38(1H, d, J = 2.2 Hz), 8.47 (1H, dd, J = 2.2, 8.8 Hz); ESI+: 571 |
| 48# | 2 | NMR1: 1.36-1.50(2H, m), 1.81-2.01(3H, m), 2.80-2.94(2H, m), 3.22-3.31(2H m) 3.45(2H, d, J = 6.2 Hz), 3.95(3H, s), 4.76(2H, s), 7.15(1H, d, J = 3.6 Hz), 7.95(1H, d, J = 8.1 Hz), 8.10(1H, d, J = 3.6 Hz), 8.40-8.54(3H, m), 8.80(1H, br); ESI+: 430 |
| 49# | 11 | NMR1: 0.98(3H, t, J = 7.2 Hz), 1.16-1.29(2H, m), 1.54-1.74(3H, m), 1.78-1.88(2H, m), 2.29(2H, q, J = 7.2 Hz), 2.80-2.89(2H, m), 3.41(2H, d, J = 6.3 Hz), 3.94(3H, s), 4.73(2H, s), 7.17(1H, d, J = 3.6 Hz), 7.96(1H, d, J = 8.1 Hz), 8.09(1H, d, J = 3.6 Hz), 8.43(1H, d, J = 1.5 Hz), 8.51(1H, dd, J = 1.5, 8.1 Hz); ESI+: 458 |
| 50 | 2 | NMR1: 1.18-1.31(1H, m), 1.54-2.01(6H, m), 2.58-2.70(1H, m), 2.70-2.83(1H, m), 3.14-3.41(2H, m), 3.94(3H, s), 4.54-4.69(2H, m), 7.23(1H, d, J = 3.6 Hz), 8.09(1H, d, J = 3.6 Hz), 8.60(1H, br), 8.73(1H, d, J = 2.2 Hz), 8.88(1H, br), 9.24(1H, d, J = 2.2 Hz); ESI+: 431 |
| 51 | 2 | NMR1: 1.34-1.49(2H, m), 1.59-1.69(1H, m), 1.71-1.97(6H, m), 2.76-2.93(3H, m), 3.21-3.30(2H, m), 3.49-3.55(1H, m), 3.60-3.69(2H, m), 3.79-3.86(1H, m), 4.34-4.40(2H, m), 4.57-4.64(2H, m), 7.26(1H, d, J = 3.6 Hz), 8.20(1H, d, J = 3.6 Hz), 8.57(1H, br), 8.72(1H, d, J = 2.2 Hz), 8.80(1H, br), 9.24(1H, d, J = 2.21-4); ESI+: 501 |
| 52 | 12 | NMR1: 1.22(3H, t, J = 7.3 Hz), 1.41-1.55(2H, m), 1.58-1.83(3H, m), 1.87-2.00(4H, m), 2.77-2.93(3H, m), 3.01-3.12(2H, m), 3.42-3.55(3H, m), 3.60-3.69(2H, m), 3.78-3.86(1H, m), 4.33-4.40(2H, m), 4.62(2H, t, J = 6.0 Hz), 7.26(1H, d, J = 3.6 Hz), 8.20(1H, d, J = 3.6 Hz), 8.73(1H, d, J = 2.2 Hz), 9.25(1H, d, J = 2.2 Hz), 9.43(1H, br); ESI+: 529 |
| 53# | 2 | NMR1: 1.32-1.49(2H, m), 1.70-1.94(6H, m), 1.97-2.23(3H, m), 2.29-2.41(2H, m), 2.78-2.94(2H, m), 3.20-3.34(2H, m), 3.56-3.80(1H, m), 3.91(3H, s), 4.13(2H, t, J = 6.1 Hz), 7.06(1H, d, J = 3.5 Hz), 7.15(1H, d, J = 8.7 Hz), 7.96-8.01(2H, m), 8.05(1H, dd, J = 2.3, 8.6 Hz), 8.39-8.54(1H, br), 8.66-8.83(1H, br); ESI+: 416 |
| 54 | 13 | NMR1: 1.24(3H, t, J = 7.3 Hz), 1.46-1.69(3H, m), 1.72-1.82(3H, m), 1.88-2.01(3H, m), 2.77-2.93(3H, m), 3.01-3.10(2H, m), 3.42-3.55(3H, m), 3.57-3.68(2H, m), 3.78-3.86(1H, m), 4.28-4.40(4H, m), 7.14(1H, d, J = 3.6 Hz), 7.51(1H, d, J = 8.8 Hz), 8.16(1H, d, J = 3.6 Hz), 8.39(1H, d, J = 2.2 Hz), 8.49(1H, dd, J = 2.2, 8.8 Hz), 9.79(1H, br); ESI+: 528 |
| 55# | 9 | NMR1: 1.12-1.36(3H, m), 1.45-1.60(2H, m), 1.63-1.72(2H, m), 1.74-1.86(2H, m), 2.13(3H, s), 2.69-2.77(2H, m), 3.23-3.38(2H, m), 3.89(3H, s), 6.14-6.21(1H, m), 7.00(1H, d, J = 8.8 Hz), 7.09(1H, d, J = 3.6 Hz), 7.96(1H, d, J = 3.6 Hz), 8.27-8.35(2H, m); ESI+: 443 |
| 56 | 2 | NMR1: 1.3-1.45(2H, m), 1.75-1.94(5H, m), 2.78-2.92(2H, m), 3.20-3.40(2H, m), 3.90(3H, s), 4.6-4.67(2H, m), 7.88-8.6(2H, br), 9.23(1H, d, J = 2.4 Hz), 9.77(1H, d, J = 2.4 Hz); ESI+: 500 |

TABLE 56-continued

| Ex | Syn | DAT |
|---|---|---|
| 57# | 9 | NMR1: 1.53-1.67(12H, m), 1.99-2.04(3H, m), 2.78(2H, t, J = 6.0 Hz), 3.20-3.26(2H, m), 3.89(3H, s), 6.31 (1H, t, J = 4.8 Hz), 7.00(1H, d, J = 8.8 Hz), 7.08(1H, d, J = 3.6 Hz), 7.96(1H, d, J = 3.6 Hz), 8.29-8.34(3H, m); ESI+: 495 |

TABLE 57

| Ex | Syn | DAT |
|---|---|---|
| 58 | 2 | NMR1: 1.34-1.51(2H, m), 1.55-1.67(1H, m), 1.73-1.94(7H, m), 1.95-2.06(1H, m), 2.76-2.91(2H, m), 3.22-3.36(2H, m), 3.60-3.68(1H, m), 3.75-3.83(1H, m), 4.20-4.49(5H, m), 7.11(1H, d, J = 3.6 Hz), 7.51(1H, d, J = 9.0 Hz), 8.06(1H, d, J = 3.6 Hz), 8.38(1H, d, J = 2.1 Hz), 8.44-8.64(2H, m), 8.71-8.87(1H, br); ESI+: 500 |
| 59# | 9 | NMR1: 1.59-1.71(2H, m), 1.85-1.95(2H, m), 2.03-2.12(2H, m), 2.19(3H, s), 2.66-2.77(2H, m), 3.48-3.61(1H, m), 3.89(3H, s), 5.30(1H, d, J = 7.7 Hz), 7.06(1H, d, J = 3.6 Hz), 7.09-7.13(1H, m), 7.96(1H, d, J = 3.6 Hz), 8.27-8.32(2H, m); ESI+: 415 |
| 60# | 9 | NMR1: 1.14-1.30(2H, m), 1.56-1.70(3H, m), 1.74-1.84(2H, m), 2.13(3H, s), 2.72-2.79(2H, m), 3.16-3.25(2H, m), 3.89(3H, s), 6.23-6.28(1H, m), 7.00-7.05(1H, m), 7.07(1H, d, J = 3.6 Hz), 7.95(1H, d, J = 3.6 Hz), 8.25-8.31(2H, m); ESI+: 429 |
| 61# | 9 | NMR1: 1.68-1.77(4H, m), 1.77-1.86(2H, m), 2.44-2.52(4H, m), 2.56-2.63(2H, m), 3.32-3.40(2H, m), 3.89(3H, s), 6.95-7.02(1H, m), 7.07(1H, d, J = 3.6 Hz), 7.15-7.22(1H, m), 7.95(1H, d, J = 3.6 Hz), 8.28-8.34(2H, m); ESI+: 429 |
| 62# | 2 | NMR1: 1.30-1.48(2H, m), 1.77-1.96(5H, m), 2.78-2.90(2H, m), 3.23-3.33(3H, m), 3.36(3H, s), 3.93(3H, s), 4.32-4.42(2H, m), 7.09(1H, d, J = 3.6 Hz), 7.54(1H, d, J = 8.9 Hz), 8.08(1H, d, J = 3.6 Hz), 8.46-8.62(2H, m), 8.67(1H, d, J = 2.3 Hz); ESI+: 440 |
| 63# | 9 | NMR1: 1.12(6H, s), 1.63-1.75(4H, m), 2.47-2.61(4H, m), 3.10-3.16(2H, m), 3.90(3H, s), 6.02-6.11(1H, br), 6.92-7.00(1H, m), 7.08(1H, d, J = 3.5 Hz), 7.97(1H, d, J = 3.5 Hz), 8.28-8.35(2H, m); ESI+: 443 |
| 64# | 9 | NMR1: 1.55-1.73(3H, m), 1.74-1.97(3H, m), 2.05-2.15(1H, m), 2.27(3H, s), 2.92-3.00(1H, m), 3.25-3.40(3H, m), 3.89(3H, s), 6.93-6.99(1H, m), 7.07(1H, d, J = 3.6 Hz), 7.27-7.37(1H, m), 7.95(1H, d, J = 3.6 Hz), 8.25-8.36(2H, m); ESI+: 429 |
| 65 | 13 | NMR1: 1.50-2.00(8H, m), 2.81-3.00(3H, m), 3.08-3.16(2H, m), 3.19-3.26(1H, m), 3.48-3.56(3H, m), 3.61-3.69(2H, m), 3.73-3.86(3H, m), 4.26-4.44(4H, m), 5.30(1H, br), 7.14(1H, d, J = 3.6 Hz), 7.51(1H, d, J = 8.8 Hz), 8.17(1H, d, J = 3.6 Hz), 8.39(1H, d, J = 2.1 Hz), 8.49(1H, dd, J = 2.1, 8.8 Hz), 9.70(1H, br); ESI+: 544 |
| 66 | 13 | NMR1: 1.52-2.00(7H, m), 2.81-3.06(10H, m), 3.20-3.28(1H, m), 3.36-3.55(3H, m), 3.61-3.69(2H, m), 3.78-3.86(1H, m), 4.21-4.41(6H, m), 7.14(1H, d, J = 3.6 Hz), 7.51(1H, d, J = 8.8 Hz), 8.17(1H, d, J = 3.6 Hz), 8.39(1H, d, J = 2.1 Hz), 8.49(1H, dd, J = 2.1, 8.8 Hz), 9.46(1H, br); ESI+: 585 |
| 67# | 9 | NMR1: 1.13-1.35(3H, m), 1.49-1.72(5H, m), 1.75-1.97(3H, m), 2.13(3H, s), 2.66-2.77(2H, m), 2.80-2.91(1H, m), 3.27-3.39(2H, m), 3.47-3.53(1H, m), 3.59-3.68(2H, m), 3.77-3.85(1H, m), 4.25-4.37(2H, m), 6.15-6.20(1H, m), 7.00(1H, d, J = 8.8 Hz), 7.11 (1H, d, J = 3.6 Hz), 8.06(1H, d, J = 3.6 Hz), 8.27-8.33(2H, m); ESI+: 513 |
| 68 | 2 | NMR1: 1.34-1.49(2H, m), 1.73-1.93(5H, m), 2.76-2.89(2H, m), 3.22-3.30(2H, m), 4.27-4.35(2H, m), 7.08(1H, dd, J = 1.6, 3.6 Hz), 7.51(1H, d, J = 8.9 Hz), 8.03(1H, dd, J = 2.4, 3.6 Hz), 8.39(1H, d, J = 2.1 Hz), 8.49(1H, dd, J = 2.2, 8.8 Hz), 8.57-8.71(1H, m), 8.81-8.96(1H, br), 13.03(1H, br-s); ESI+: 416 |
| 69# | 9 | NMR1: 0.92-1.08(1H, m), 1.35-1.51(2H, m), 1.58-1.72(2H, m), 1.72-1.83(1H, m), 1.87-2.02(2H, m), 2.13(3H, s), 2.46-2.60(1H, m), 2.61-2.72(1H, m), 3.17-3.27(2H, m), 3.89(3H, s), 6.37-6.51(1H, m), 7.00-7.05(1H, m), 7.08(1H, d, J = 3.6 Hz), 7.95(1H, d, J = 3.6 Hz), 8.27-8.33(2H, m); ESI+: 429 |

TABLE 58

| Ex | Syn | DAT |
|---|---|---|
| 70 | 11 | NMR1: 0.98(3H, t, J = 7.2 Hz), 1.13-1.29(2H, m), 1.42-1.56(1H, m), 1.61-1.85(7H, m), 1.90-2.03(1H, m), 2.28(2H, q, J = 7.2 Hz), 2.80-2.96(3H, m), 3.51-3.58(1H, m), 3.59-3.72(2H, m), 3.77-3.85(1H, m), 4.24-4.39(4H, m), 7.56(1H, d, J = 9.1 Hz), 9.03(1H, s), 9.04(1H, dd, J = 2.0, 9.1 Hz), 9.18 (1H, d, J = 2.0 Hz); ESI+: 529 |

TABLE 58-continued

| Ex | Syn | DAT |
|---|---|---|
| 71 | 11 | NMR1: 0.97(3H, t, J = 7.2 Hz), 1.13-1.27(2H, m), 1.37-1.53(1H, m), 1.60-1.85(7H, m), 1.91-2.02(1H, m), 2.27(2H, q, J = 7.1 Hz), 2.76-2.97(3H, m), 3.51-3.58(1H, m), 3.59-3.73(2H, m), 3.77-3.86(1H, m), 4.29-4.44(2H, m), 4.54-4.64(2H, m), 9.08(1H, s), 9.32(1H, d, J = 2.1 Hz), 9.74(1H, d, J = 2.1 Hz); ESI+: 530 |
| 72 | 3 | NMR1: 1.19-1.31 (2H, m), 1.46-1.56(1H, m), 1.66-1.77(4H, m), 1.96-2.09(2H, m), 2.80(3H, s), 2.81-2.88(2H, m), 3.01 (3H, s), 3.08-3.18(2H, m), 3.92(3H, s), 4.27-4.31(2H, m), 7.55(1H, d, J = 8.8 Hz), 8.91(1H, s), 9.04(1H, dd, J = 2.0, 8.8 Hz), 9.15 (1H, d, J = 2.0 Hz); ESI+: 516 |
| 73 | 14 + 13 | NMR1: 1.33 (9H, s), 1.48-1.62(2H, m), 1.73-1.86(3H, m), 1.94-2.04(2H, m), 2.80-2.93(2H, m), 3.48-3.56(2H, m), 3.93 (3H, s), 4.29-4.36(2H, m), 7.12(1H, d, J = 3.6 Hz), 7.52(1H, d, J = 8.9 Hz), 8.04(1H, d, J = 3.6 Hz), 8.40(1H, d, J = 2.2 Hz), 8.50(1H, dd, J = 2.2, 8.7 Hz), 8.90(1H, br); ESI+: 486 |
| 74 | 8 | NMR1: 1.20-1.32(2H, m), 1.60-1.81(5H, m), 2.72-2.90(3H, m), 3.08-3.67(13H, m), 3.82-3.88(2H, m), 4.29-4.35(2H, m), 5.38(2H, s), 7.15(1H, d, J = 3.6 Hz), 7.52(1H, d, J = 9.0 Hz), 7.96(1H, d, J = 3.6 Hz), 8.39(1H, d, J = 2.0 Hz), 8.48(1H, dd, J = 2.0, 8.9 Hz); ESI+: 571 |
| 75 | 8 | NMR1: 1.00-1.40(2H, m), 1.52-2.10(6H, m), 2.65-2.76(1H, m), 2.95-3.43(15H, m), 3.54-3.66(3H, m), 3.81-3.90(2H, m), 4.00-4.11(1H, m), 4.25-4.38(3H, m), 5.30-5.50(2H, m), 7.14(1H, d, J = 3.6 Hz), 7.52(1H, d, J = 8.8 Hz), 7.96(1H, d, J = 3.6 Hz), 8.39(1H, d, J = 1.6 Hz), 8.48(1H, dd, J = 1.6, 8.8 Hz); ESI+: 625 |
| 76 | 10 | NMR1: 1.35-1.45 (5H, m), 1.74-1.93(5H, m), 2.78-2.90(2H, m), 3.23-3.41(2H, m), 4.31(2H, t, J = 6 Hz), 4.39(2H, q, J = 7.2 Hz), 7.12(1H, d, J = 3.6 Hz), 7.50 (1H, d, J = 8.8 Hz), 8.14(1H, d, J = 3.6 Hz), 8.38(1H, d, J = 2.4 Hz), 8.44-8.55(2H, m), 8.69-8.80(1H, br); ESI+: 444 |
| 77 | 6 | NMR1: 0.81-0.89(1H, m), 0.97-1.32(4H, m), 1.59-1.83(7H, m), 1.90-2.07(2H, m), 2.12-2.23(4H, m), 2.83-3.01(3H, m), 3.02-3.16(1H, m), 3.51-3.58(1H, m), 3.59-3.73(2H, m), 3.76-3.86(1H, m), 4.11-4.46(6H, m), 7.56(1H, d, J = 9.0 Hz), 9.00-9.07(2H, m), 9.15-9.19(1H, m); ESI+: 612 |
| 78 | 2 | NMR1: 1.32-1.47(2H, m), 1.74-1.85(3H, m), 1.85-1.97(4H, m), 2.11-2.25(2H, m), 2.78-2.92(2H, m), 3.22-3.38(2H, m), 3.56-3.67(2H, m), 3.98-4.08(1H, m), 4.27-4.35(2H, m), 4.97-5.08(1H, m), 7.16(1H, d, J = 3.7 Hz), 7.50(1H, d, J = 8.9 Hz), 8.24-8.42(3H, m), 8.48(1H, dd, J = 2.2, 8.8 Hz), 8.56-8.68(1H, br); ESI+: 500 |
| 79 | 6 | NMR1: 0.81-1.34(5H, m), 1.58-1.86(7H, m)1.90-2.09(2H, m), 2.11-2.25(4H, m), 2.84-3.01(3H, m), 3.03-3.18(1H, m), 3.51-3.59(1H, m), 3.59-3.73(2H, m), 3.76-3.87(1H, m), 4.10-4.26(1H, m), 4.29-4.45(3H, m), 4.55-4.67(2H, m), 9.08(1H, s), 9.32(1H, d, J = 1.7 Hz), 9.74(1H, d, J = 1.7 Hz); ESI+: 613 |
| 80 | 10 | NMR1: 1.21-1.50(6H, m), 1.70-1.93(5H, m), 2.09-2.25(1H, m), 2.76-2.91(2H, m) 3.17-3.31(4H, m), 3.78-3.88(2H, m), 4.05-4.43(2H, m), 4.56-4.65(2H, m), 7.25(1H, d, J = 3.6 Hz) 8.13(1H, d, J = 3.6 Hz) 8.54(1H, br), 8.71(1H, d, J = 2.2 Hz), 8.76(1H, br), 9.24(1H, d, J = 2.2 Hz); ESI+: 515 |

TABLE 59

| Ex | Syn | DAT |
|---|---|---|
| 81 | 13 | NMR1: 1.19-1.59(9H, m), 1.66-2.00(5H, m), 2.10-2.24(1H, m), 2.76-2.90(2H, m), 3.00-3.29(4H, m), 3.40-3.51(2H, m), 3.79-3.88(2H, m), 4.28(2H, d, J = 7.2 Hz), 4.61(2H, t, J = 6.0 Hz), 7.25(1H, d, J = 3.6 Hz), 8.13(1H, d, J = 3.6 Hz), 8.72(1H, d, J = 2.2 Hz), 9.24(1H, d, J = 2.2 Hz), 9.67(1H, br); ESI+: 543 |
| 82 | 10 | NMR1: 3.25-3.41(1H, m), 3.84-3.97(5H, m), 3.99-4.12(2H, m), 4.44(2H, d, J = 6.2 Hz), 7.13(1H, d, J = 3.6 Hz), 7.51(1H, d, J = 8.9 Hz), 8.07(1H, d, J = 3.6 Hz), 8.41(1H, d, J = 2.1 Hz), 8.52(1H, dd, J = 2.1, 8.9 Hz), 8.77-9.11(2H, m); ESI+: 388 |
| 83 | 10 | NMR1: 1.33-1.47(1H, m), 1.62-1.77(1H, m), 1.82-1.95(2H, m), 2.25-2.39(1H, m), 2.72-2.86(2H, m), 3.23-3.47(2H, m), 3.93(3H, s), 4.11-4.20(1H, m), 4.22-4.30(1H, m), 7.12(1H, d, J = 3.6 Hz), 7.49(1H, d, J = 8.8 Hz), 8.06(1H, d, J = 3.6 Hz), 8.40(1H, d, J = 2.0 Hz), 8.50(1H, dd, J = 2.0, 8.8 Hz), 8.57-8.86(2H, m); ESI+: 416 |
| 84 | 10 | NMR1: 1.57-1.70(1H, m), 1.87-2.03(2H, m), 2.07-2.19(1H, m), 2.34-2.47(1H, m), 2.77-2.88(2H, m), 3.05-3.17(1H, m), 3.19-3.52(2H, m), 3.93(3H, s), 4.26-4.36(2H, m), 7.12(1H, d, J = 3.6 Hz), 7.51(1H, d, J = 8.8 Hz), 8.06(1H, d, J = 3.6 Hz), 8.40(1H, d, J = 2.0 Hz), 8.50(1H, dd, J = 2.0, 8.8 Hz), 8.75-9.01(2H, m); ESI+: 416 |
| 85 | 10 | NMR1: 1.38-1.52(2H, m), 1.58-1.69(1H, m), 1.77-1.98(6H, m), 2.80-2.94(3H, m), 3.22-3.32(2H, m), 3.51(1H, dd, J = 5.3, 8.7 Hz), 3.60-3.68(2H, m), 3.78-3.86(1H, m), 4.28-4.41(4H, m), 7.25(1H, d, J = 3.6 Hz), 7.49(1H, d, J = 8.8 Hz), 8.17(1H, d, J = 3.6 Hz), 8.40-8.52(2H, m), 8.52-8.90(2H, m); ESI+: 457 |

TABLE 59-continued

| Ex | Syn | DAT |
|---|---|---|
| 86 | 10 | NMR1: 1.45-1.69(3H, m), 1.88-2.00(3H, m), 2.10-2.23(1H, m), 2.81-3.00(3H, m), 3.31-3.38(2H, m), 3.53(1H, dd, J = 5.3, 8.7 Hz), 3.60-3.68(2H, m), 3.78-3.86(1H, m), 4.16(2H, d, J = 6.0 Hz), 4.30-4.42(2H, m), 7.13(1H, d, J = 3.6 Hz), 7.51(1H, d, J = 8.8 Hz), 8.16(1H, d, J = 3.6 Hz), 8.39(1H, d, J = 2.0 Hz), 8.46-8.51(1H, m), 8.51-8.80(2H, m); ESI+: 486 |
| 87 | 11 | NMR1: 0.98(3H, t, J = 7.2 Hz), 1.16-1.30(2H, m), 1.44-1.97(9H, m), 2.29(2H, q, J = 7.2 Hz), 2.78-2.93(3H, m), 3.51(1H, dd, J = 5.3, 8.7 Hz), 3.60-3.69(2H, m), 3.78-3.86(1H, m), 4.28-4.39(4H, m), 7.25(1H, d, J = 3.6 Hz), 7.49(1H, d, J = 9.3 Hz), 8.16(1H, d, J = 3.6 Hz), 8.45-8.51(2H, m); ESI+: 485 |
| 88 | 12 | NMR1: 1.23(3H, t, J = 7.3 Hz), 1.40-1.67(3H, m), 1.68-2.06(8H, m), 2.76-2.92(2H, m), 3.02-3.12(2H, m), 3.42-3.52(2H, m), 3.60-3.68(1H, m), 3.75-3.83(1H, m), 4.20-4.49(5H, m), 7.12(1H, d, J = 3.6 Hz), 7.51(1H, d, J = 8.9 Hz), 8.06(1H, d, J = 3.6 Hz), 8.39(1H, d, J = 2.1 Hz), 8.49(1H, dd, J = 2.1, 8.7 Hz), 9.33-9.60(1H, br); ESI+: 528 |
| 89 | 11 | NMR1: 0.87(3H, t, J = 7.2 Hz), 2.41(2H, q, J = 7.2 Hz), 2.80-2.92(1H, m), 2.95-3.05(2H, m), 3.25-3.33(2H, m), 3.93(3H, s), 4.34(2H, d, J = 6.1 Hz), 7.12(1H, d, J = 3.6 Hz), 7.50(1H, d, J = 8.9 Hz), 8.05(1H, d, J = 3.6 Hz), 8.39(1H, d, J = 2.1 Hz), 8.47(1H, dd, J = 2.1, 8.9 Hz); ESI+: 416 |
| 90 | 11 | NMR1: 1.00(3H, t, J = 7.2 Hz), 1.09-1.29(1H, m), 1.43-1.57(1H, m), 1.62-1.72(1H, m), 1.72-1.81(1H, m), 1.81-2.00(2H, m), 2.00-2.12(1H, m), 2.23-2.41(2H, m), 2.66-2.80(1H, m), 2.86-2.99(1H, m), 3.92(3H, s), 4.05-4.21(2H, m), 7.11(1H, d, J = 3.6 Hz), 7.47(1H, d, J = 8.8 Hz), 8.04(1H, d, J = 3.6 Hz), 8.37(1H, d, J = 2.0 Hz), 8.46(1H, dd, J = 2.0, 8.8 Hz); ESI+: 444 |

TABLE 60

| Ex | Syn | DAT |
|---|---|---|
| 91 | 11 | NMR1: 1.01(3H, t, J = 7.2 Hz), 1.36-1.49(1H, m), 1.77-2.01(3H, m), 2.10-2.17(1H, m), 2.21-2.45(4H, m), 2.48-2.58(1H, m), 2.67-2.76(1H, m), 3.92(3H, s), 4.21-4.29(2H, m), 7.11(1H, d, J = 3.6 Hz), 7.48(1H, d, J = 8.8 Hz), 8.04(1H, d, J = 3.6 Hz), 8.37(1H, d, J = 2.0 Hz), 8.46(1H, dd, J = 2.0, 8.8 Hz); ESI+: 444 |
| 92 | 11 | NMR1: 0.96(3H, t, J = 7.2 Hz), 1.37-1.49(2H, m), 1.76-1.86(2H, m), 1.94-2.06(2H, m), 2.26(2H, q, J = 7.2 Hz), 2.58-2.70(2H, m), 3.34-3.45(1H, m), 3.76-3.83(2H, m), 3.92(3H, s), 4.33-4.40(2H, m), 7.11(1H, d, J = 3.6 Hz), 7.51(1H, d, J = 8.8 Hz), 8.04(1H, d, J = 3.6 Hz), 8.38(1H, d, J = 2.1 Hz), 8.46(1H, dd, J = 2.1, 8.8 Hz); ESI+: 474 |
| 93 | 6 | NMR1: 1.64-1.83(3H, m), 1.91-2.07(1H, m), 2.09-2.19(1H, m), 2.21-2.25(3H, m), 2.73-2.83(1H, m), 2.91-3.00(1H, m), 3.04-3.17(1H, m), 3.73-3.85(1H, m), 3.87-4.03(4H, m), 4.09-4.18(1H, m), 4.30-4.44(3H, m), 7.12(1H, d, J = 3.6 Hz), 7.51(1H, d, J = 8.9 Hz), 8.05(1H, d, J = 3.6 Hz), 8.29(1H, d, J = 2.0 Hz), 8.49(1H, dd, J = 2.0, 8.9 Hz); ESI+: 499 |
| 94 | 6 | NMR1: 1.31-1.52(2H, m), 1.58-2.26(11H, m), 2.59-2.77(1H, m), 2.89-3.19(3H, m), 3.93(3H, s), 4.00-4.31(4H, m), 7.11(1H, d, J = 3.5 Hz), 7.44-7.55(1H, m), 8.05(1H, d, J = 3.5 Hz), 8.37-8.43(1H, m), 8.44-8.53(1H, m); ESI+: 527 |
| 95 | 6 | NMR1: 1.48-1.79(4H, m), 1.86-2.42(9H, m), 2.91-3.07(2H, m), 3.11-3.85(4H, m), 3.93(3H, s), 4.27-4.36(2H, m), 7.09-7.15(1H, m), 7.47-7.55(1H, m), 8.02-8.07(1H, m), 8.36-8.41(1H, m), 8.45-8.52(1H, m); ESI+: 527 |
| 96 | 3 | NMR1: 1.12-1.29(1H, m), 1.42-1.57(1H, m), 1.60-1.80(2H, m), 1.98-2.19(3H, m), 2.58-2.88(5H, m), 3.01(3H, s), 3.03-3.19(2H, m), 3.92(3H, s), 4.08-4.20(2H, m), 7.11(1H, d, J = 3.5 Hz), 7.47(1H, d, J = 8.8 Hz), 8.04(1H, d, J = 3.5 Hz), 8.37(1H, d, J = 1.4 Hz), 8.46(1H, dd, J = 1.4, 8.8 Hz); ESI+: 501 |
| 97 | 12 | NMR1: 1.08-1.30(6H, m), 1.64-1.97(4H, m), 2.99-3.20(4H, m), 3.31-3.48(2H, m), 3.93(3H, s), 3.98-4.01(1H, m), 4.24-4.29(1H, m), 7.11(1H, d, J = 3.6 Hz), 7.47-7.56(1H, m), 8.06(1H, d, J = 3.6 Hz), 8.38-8.42(1H, m), 8.46-8.56(1H, m), 9.59-9.89(1H, m); ESI+: 458 |
| 98# | 9 | NMR1: 2.14(6H, s), 2.40(2H, t, J = 5.8 Hz), 3.48(2H, q, J = 6.0 Hz), 3.53(2H, t, J = 5.8 Hz), 3.63(2H, t, J = 6.0 Hz), 3.90(3H, s), 5.93-5.99(1H, m), 7.08(1H, d, J = 3.6 Hz), 7.11(1H, d, J = 3.6 Hz), 7.97(1H, d, J = 3.6 Hz), 8.28-8.34(2H, m); ESI+: 433 |
| 99# | 9 | NMR1: 1.96-2.06(2H, m), 2.25(3H, s), 3.26-3.37(2H, m), 3.90(3H, s), 3.96(2H, t, J = 7.1 Hz), 6.25-6.35(1H, m), 6.74(1H, d, J = 1.2 Hz), 6.96-7.01(1H, m), 7.05-7.10(2H, m), 7.96(1H, d, J = 3.5 Hz), 8.26-8.32(2H, m); ESI+: 440 |
| 100# | 9 | NMR1: 1.86-1.96(2H, m), 2.17-2.25(2H, m), 3.38-3.49(6H, m), 3.90(3H, s), 6.25-6.31(1H, br), 7.05-7.11(2H, m), 7.97(1H, d, J = 3.6 Hz), 8.27-8.36(2H, m); ESI+: 429 |

TABLE 60-continued

| Ex | Syn | DAT |
|---|---|---|
| 101 | 2 | NMR1: 1.33-1.47(2H, m), 1.74-1.94(5H, m), 2.16-2.26(1H, m), 2.53-2.64(1H, m), 2.77-2.90(2H, m), 3.22-3.32(2H, m), 3.83-3.92(1H, m), 3.92-4.04(2H, m), 4.10-4.19(1H, m), 4.26-4.36(2H, m), 5.54-5.62(1H, m), 7.16(1H, d, J = 3.7 Hz), 7.51(1H, d, J = 9.0 Hz), 8.06(1H, d, J = 3.8 Hz), 8.38(1H, d, J = 2.2 Hz), 8.40-8.52(2H, m), 8.63-8.78(1H, m); ESI+: 486 |

TABLE 61

| Ex | Syn | DAT |
|---|---|---|
| 102 | PSyn24 + 11 | NMR1: 0.98(3H, t, J = 7.2 Hz), 1.14-1.27(2H, m), 1.45-1.55(1H, m), 1.65-1.85(6H, m), 2.28(2H, q, J = 7.2 Hz), 2.81-2.88(2H, m), 4.29(2H, t, J = 6.8 Hz), 5.03(2H, s), 7.12(1H, d, J = 3.6 Hz), 7.35(1H, br-s), 7.51(1H, d, J = 9.2 Hz), 7.76(1H, br-s), 8.02(1H, d, J = 3.6 Hz), 8.38(1H, d, J = 2.4 Hz), 8.47(1H, dd, J = 2.4, 9.2 Hz); ES1+: 501 |
| 103 | 103 | NMR1: 1.08(3H, t, J = 7.2 Hz), 1.29-1.40(2H, m), 1.44(3H, t, J = 7.6 Hz), 1.58-1.68(1H, m), 1.72-1.84(4H, m), 2.22-2.36(2H, m), 2.60-2.69(2H, m), 3.07-3.16(2H, m), 4.30(2H, t, J = 6.4 Hz), 4.39(2H, q, J = 7.2 Hz), 6.54(2H, s), 7.13(1H, d, J = 3.6 Hz), 7.50(1H, d, J = 8.8 Hz), 8.13(1H, d, J = 3.6 Hz), 8.38(1H, d, J = 2.4 Hz), 8.47 (1H, dd, J = 2.4, 8.8 Hz); ESI+: 472 |
| 104 | 6 | NMR1: 1.00-1.25(2H, m), 1.57-1.85(9H, m), 1.86-1.97(1H, m), 1.98-2.10(1H, m), 2.11-2.24(4H, m), 2.50-2.62(1H, m), 2.80-3.18(4H, m), 3.51(1H, dd, J = 5.3, 8.7 Hz), 3.60-3.69(2H, m), 3.78-3.86(1H, m), 4.10-4.46(6H, m), 7.25(1H, d, J = 3.6 Hz), 7.50(1H, d, J = 9.3 Hz), 8.16(1H, d, J = 3.6 Hz), 8.45-8.51(2H, m); ESI+: 568 |
| 105 | 6 | NMR1: 1.11-1.40(2H, m), 1.58-2.21(10H, m), 2.21(3H, s), 2.52-2.65(1H, m), 2.80-3.21(4H, m), 3.51(1H, dd, J = 5.3, 8.7 Hz), 3.60-3.69(2H, m), 3.78-3.86(1H, m), 4.09-4.52(6H, m), 7.14(1H, d, J = 3.6 Hz), 7.48(1H, d, J = 8.9 Hz), 8.15(1H, d, J = 3.6 Hz), 8.38(1H, d, J = 2.2 Hz), 8.47(1H, dd, J = 2.2, 8.9 Hz); ESI+: 597 |
| 106 | PSyn26 + 103 | NMR1: 1.08(3H, t, J = 7.2 Hz), 1.35-1.55(2H, m), 1.59-1.68(1H, m), 1.76-1.99(4H, m), 2.20-2.35(2H, m), 2.55-2.64(2H, m), 2.80-2.93(1H, m), 3.08-3.16(2H, m), 3.51(1H, dd, J = 5.3, 8.7 Hz), 3.60-3.69(2H, m), 3.78-3.86(1H, m), 4.10-4.18(2H, m), 4.30-4.41(2H, m), 6.55(2H, s), 7.13(1H, d, J = 3.6 Hz), 7.49(1H, d, J = 8.9 Hz), 8.15(1H, d, J = 3.6 Hz), 8.38(1H, d, J = 2.4 Hz), 8.47(1H, dd, J = 2.4, 8.9 Hz); ESI+: 514 |
| 107 | 10 | NMR1: 1.32-1.47(2H, m), 1.71-1.94(5H, m), 2.77-2.91(2H, m), 3.22-3.76(10H, m), 4.57-4.66(2H, m), 5.41(2H, s), 7.25(1H, d, J = 3.6 Hz), 7.99(1H, d, J = 3.6 Hz), 8.38(1H, br), 8.63(1H, br), 8.74(1H, d, J = 2.2 Hz), 9.26(1H, d, J = 2.2 Hz); ESI+: 544 |
| 108 | 16 | NMR1: 1.46-1.67(2H, m), 1.70-1.86(4H, m), 1.86-2.05(4H, m), 2.86-3.00(2H, m), 3.08-3.17(2H, m), 3.19-3.35(1H, m), 3.46-3.56(2H, m), 3.60-3.69(1H, m), 3.71-3.83(3H, m), 4.20-4.49(5H, m), 5.20-5.40(1H, br), 7.12(1H, d, J = 3.6 Hz), 7.49-7.55(1H, m), 8.06(1H, d, J = 3.7 Hz), 8.39(1H, d, J = 2.1 Hz), 8.49(1H, dd, J = 2.2, 8.7 Hz), 9.31-9.54(1H, br); ESI+: 544 |
| 109 | 13 | NMR1: 1.23(3H, t, J = 7.3 Hz), 1.43-1.59(2H, m), 1.66-2.01(5H, m), 2.77-2.91(2H, m), 3.00-3.24(2H, m), 3.41-3.52(4H, m), 3.57-3.77(6H, m), 4.62(2H, t, J = 6.0 Hz), 5.42(2H, s), 7.25(1H, d, J = 3.7 Hz), 8.00(1H, d, J = 3.7 Hz), 8.74(1H, d, J = 2.2 Hz), 9.26(1H, d, J = 2.2 Hz),9.65(1H, br); ESI+: 572 |
| 110 | 13 | NMR1: 1.24(3H, t, J = 7.3 Hz), 1.45-1.61(2H, m), 1.66-2.01(5H, m), 2.76-2.90(2H, m), 3.01-3.18(2H, m), 3.42-3.52(2H, m), 3.74-3.85 (2H, m), 4.28-4.36(2H, m), 4.41(2H, t, J = 5.5 Hz), 5.00(1H, br), 7.11(1H, d, J = 3.7 Hz), 7.52(1H, d, J = 8.8 Hz), 8.08(1H, d, J = 3.7 Hz), 8.39(1H, d, J = 2.2 Hz), 8.49(1H, dd, J = 2.2, 8.8 Hz), 9.83(1H, br); ESI+: 488 |
| 111 | 11 | NMR1: 0.95(6H, d, J = 6.6 Hz), 1.14-1.29(2H, m), 1.42-1.56(1H, m), 1.58-1.81(5H, m), 1.86-1.97(1H, m), 2.01-2.17(2H, m), 2.59-2.93(4H, m), 3.51(1H, dd, J = 5.3, 8.7 Hz), 3.60-3.69(2H, m), 3.78-3.86(1H, m), 4.27-4.40(4H, m), 7.25(1H, d, J = 3.7 Hz), 7.49(1H, d, J = 9.3 Hz), 8.16(1H, d, J = 3.7 Hz), 8.44-8.52(2H, m); ESI+: 499 |

TABLE 62

| Ex | Syn | DAT |
|---|---|---|
| 112 | 11 | NMR1: 1.14-1.29(2H, m), 1.45-1.80(6H, m), 1.86-1.97(1H, m), 2.37-2.46(2H, m), 2.80-2.92(3H, m), 2.93-3.11(1H, m), 3.52(1H, dd, J = 5.3, 8.7 Hz), 3.58-3.69(2H, m), 3.78-3.86(1H, m), 4.27-4.40(4H, m), 4.50-4.55(2H, m), 4.61-4.67(2H, m), 7.25(1H, d, J = 3.6 Hz), 7.49(1H, d, J = 9.3 Hz), 8.16(1H, d, J = 3.6 Hz), 8.44-8.50(2H, m); ESI+: 535 |

TABLE 62-continued

| Ex | Syn | DAT |
|---|---|---|
| 113 | 10 | NMR1: 1.32-1.49(2H, m), 1.68-1.94(5H, m), 2.75-2.92(2H, m), 3.21-3.33(2H, m), 3.94(3H, s), 4.30-4.43(2H, m), 8.40-8.62(1H, br), 8.66-8.82(1H, br), 8.86-8.94(1H, m), 8.95-9.02(2H, m); ESI+: 449 |
| 114 | 114 | NMR1: 1.08(3H, t, J = 7.2 Hz), 1.27-1.41(2H, m), 1.56-1.68(1H, m), 1.71-1.84(4H, m), 2.18-2.34(2H, m), 2.56-2.68(2H, m), 2.80-3.90(2H, m), 4.26-4.36(2H, m), 4.99-5.10(4H, m), 5.98-6.08(1H, m), 6.54(2H, s), 7.26(1H, d, J = 3.8 Hz), 7.51(1H, d, J = 9.0 Hz), 8.38(1H, d, J = 2.2 Hz), 8.45-8.53(2H, m); ESI+: 500 |
| 115 | 115 | NMR1: 0.99-1.29(2H, m), 1.63-1.88(8H, m), 2.10-2.24(1H, m), 2.30-2.52(4H, m), 2.52-2.64(1H, m), 2.77-3.86(3H, m), 3.96-4.13(1H, m), 4.26-4.44(3H, m), 4.99-5.10(4H, m), 5.99-6.08(1H, m), 6.56(2H, s), 7.26(1H, d, J = 3.8 Hz), 7.52(1H, d, J = 8.9 Hz), 8.38(1H, d, J = 2.2 Hz), 8.45-8.53(2H, m); ESI+: 583 |
| 116 | 10 | NMR1: 1.34-1.50(2H, m), 1.72-1.96(5H, m), 2.78-2.91 (2H, m), 3.21-3.32(2H, m), 3.94(3H, s), 4.56-4.65(2H, m), 7.23(1H, d, J = 3.6 Hz), 8.08(1H, d, J = 3.6 Hz), 8.48(1H, br), 8.66-8.79(2H, m), 9.22-9.25(1H, m); ESI+: 431 |
| 117 | 6 | NMR1: 0.96-1.26(2H, m), 1.49-1.66(1H, m), 1.66-1.84(5H, m), 2.18(3H, s), 2.21-2.40(2H, m), 2.44-2.62(1H, m), 2.78-3.19(3H, m), 3.92(3H, s), 4.10-4.22(1H, m), 4.25-4.49(4H, m), 4.75-4.87(1H, m), 7.56(1H, d, J = 8.9 Hz), 8.91(1H, s), 9.05(1H, dd, J = 2.0, 8.9 Hz), 9.17(1H, d, J = 2.0 Hz); ESI+: 558 |
| 118 | 6 | NMR1: 0.95-1.25(2H, m), 1.67-1.83(5H, m), 1.84-1.99(2H, m), 2.18-2.23(3H, m), 2.23-2.35(1H, m), 2.36-2.45(1H, m), 2.46-2.59(2H, m), 2.64-2.78(1H, m), 2.90-3.01(1H, m), 3.14-3.25(1H, m), 3.85-3.96(4H, m), 4.24-4.42(3H, m), 7.56(1H, d, J = 8.8 Hz), 8.91(1H, s), 9.05(1H, dd, J = 2.4, 8.8 Hz), 9.16(1H, d, J = 2.4 Hz); ESI+: 542 |
| 119 | 6 | NMR1: 0.94-1.21(2H, m), 1.46-1.65(4H, m), 1.67-1.82(5H, m), 1.82-1.95(2H, m), 2.13 (3H, s), 2.42-2.58(2H, m), 2.75(2H, d, J = 11.6 Hz), 2.98(1H, t, J = 11.6 Hz), 3.86-3.98(4H, m), 4.27-4.35(2H, m), 4.35-4.46(1H, m), 7.56(1H, d, J = 9.0 Hz), 8.92(1H, s), 9.06(1H, dd, J = 2.1, 9.0 Hz), 9.17(1H, d, J = 2.1 Hz); ESI+: 556 |
| 120 | 3 | NMR1: 1.13-1.29(2H, m), 1.43-1.62(2H, m), 1.63-1.77(5H, m), 1.78-2.00(4H, m), 2.73-2.84(2H, m), 3.00-3.22(4H, m), 3.32-3.42(1H, m), 3.68-3.81(2H, m), 3.92(3H, s), 4.24-4.35(2H, m), 7.55(1H, d, J = 9.0 Hz), 8.91(1H, s), 9.04(1H, dd, J = 2.0, 9.0 Hz), 9.16(1H, d, J = 2.0 Hz); ESI+: 581 |
| 121 | 3 | NMR1: 1.16-1.30(2H, m), 1.42-1.56(1H, m), 1.64-1.79(4H, m), 1.94-2.07(2H, m), 2.28-2.53(2H, m), 2.75-2.87(2H, m), 3.03-3.08(1H, m), 3.09-3.13(1H, m), 3.51(1H, t, J = 7.6 Hz), 3.69(1H, t, J = 13.2 Hz), 3.79(1H, t, J = 7.6 Hz), 3.92(3H, s), 4.02(1H, t, J = 13.2 Hz), 4.30(2H, t, J = 6.4 Hz), 7.55(1H, d, J = 9.0 Hz), 8.91(1H, s), 9.05(1H, dd, J = 2.1, 9.0 Hz), 9.16(1H, d, J = 2.1 Hz); ESI+: 578 |

TABLE 63

| Ex | Syn | DAT |
|---|---|---|
| 122 | 3 | NMR1: 1.14-1.30(2H, m), 1.42-1.58(1H, m), 1.62-1.79(4H, m), 1.86-2.26(4H, m), 2.77-2.91(2H, m), 3.03-3.07(1H, m), 3.07-3.12(1H, m), 3.24-3.91(4H, m), 3.92(3H, s), 4.23-4.34(2H, m), 5.17-5.49(1H, m), 7.56(1H, d, J = 8.8 Hz), 8.91(1H, s), 9.05(1H, dd, J = 2.0, 8.8 Hz), 9.17(1H, d, J = 2.0 Hz); ESI+: 560 |
| 123 | PSyn3 | ESI+: 502 |
| 124 | PSyn26 | ESI+: 528 |
| 125 | 3 | ESI+: 585 |
| 126 | 3 | ESI+: 544 |
| 127 | PSyn24 | ESI+: 501 |
| 128 | PSyn24 | ESI+: 502 |
| 129 | PSyn26 | ESI+: 543 |
| 130 | PSyn26 | ESI+: 472 |
| 131 | PSyn26 | ESI+: 572 |
| 132 | PSyn24 | ESI+: 460 |
| 133 | PSyn26 | ESI+: 488 |

TABLE 63-continued

| Ex | Syn | DAT |
|---|---|---|
| 134 | 134 | NMR1: 1.23(3H, t, J = 7.3 Hz), 1.45-1.60(2H, m), 1.65-1.84(3H, m), 1.85-2.01(2H, m), 2.75-2.90(2H, m), 2.99-3.24(2H, m), 3.40-3.50(2H, m), 3.94(3H, s), 4.62(2H, t, J = 6.1 Hz), 8.97(1H, s), 9.33(1H, d, J = 2.0 Hz), 9.70-9.96(2H, m); ESI+: 460 |
| 135 | 135 | NMR2: 1.15(6H, s), 1.24-1.41(2H, m), 1.61-1.70(2H, m), 1.80-2.03(4H, m), 2.09-2.24(1H, m), 2.31(2H, s), 2.32-2.42(2H, m), 2.44-2.54(1H, m), 2.56-2.67(1H, m), 2.92-3.03(2H, m), 3.04-3.34(1H, m), 3.93-4.06(4H, m), 4.29-4.50(2H, m), 4.66-4.78(1H, m), 6.90(1H, d, J = 3.6 Hz), 7.52(1H, d, J = 3.6 Hz), 8.72(1H, d, J = 2.1 Hz), 9.10(1H, d, J = 2.1 Hz); ESI+: 600 |
| 136 | 136 | NMR1: 1.19-1.30(2H, m), 1.40-1.52(1H, m), 1.67-1.77(4H, m), 1.84-1.99(2H, m), 2.20(3H, s), 2.77-2.85(2H, m), 3.94(3H, s), 4.60(2H, t, J = 6.6 Hz), 8.96(1H, s), 9.32(1H, d, J = 2.1 Hz), 9.75(1H, d, J = 2.1 Hz); ESI+: 446 |
| 137 | 6 | NMR1: 0.96-1.20(2H, m), 1.58-1.82(8H, m), 1.96-2.08(1H, m), 2.10-2.23(4H, m), 2.43-2.59(1H, m), 2.87-3.01(2H, m), 3.02-3.15(1H, m), 3.94(3H, s), 4.10-4.26(1H, m), 4.30-4.45(1H, m), 4.62(2H, t, J = 6.1 Hz), 8.96(1H, s), 9.33(1H, d, J = 2.1 Hz), 9.76(1H, d, J = 2.1 Hz); ESI+: 543 |
| 138 | 10 | ESI+: 529 |
| 139 | 11 | ESI+: 474 |
| 140 | 11 | NMR1: 0.81-1.30(8H, m), 1.53-1.84(9H, m), 1.95-2.06(1H, m), 2.41-2.54(1H, m), 2.70-2.84(1H, m), 2.87-3.00(2H, m), 3.55-3.68(1H, m), 3.94(3H, s), 4.20-4.44(2H, m), 4.62(2H, t, J = 6.1 Hz), 8.96(1H, s), 9.32(1H, d, J = 2.1 Hz), 9.75(1H, d, J = 2.1 Hz); ESI+: 571 |
| 141 | 11 | NMR1: 1.10-1.25(2H, m), 1.37-1.50(1H, m), 1.53-1.80(10H, m), 1.88-1.98(2H, m), 2.56-2.66(1H, m), 2.70-2.80(2H, m), 3.94(3H, s), 4.59(2H, t, J = 6.5 Hz), 8.96(1H, s), 9.31(1H, d, J = 2.1 Hz), 9.74(1H, d, J = 2.1 Hz); ESI+: 486 |
| 142 | 1 | ESI+: 472 |

TABLE 64

| Ex | Syn | DAT |
|---|---|---|
| 143 | 143 | ESI+: 544 |
| 144 | 3 | ESI+: 488 |
| 145 | 11 | ESI+: 510 |
| 146 | 1 | ESI+: 488 |
| 147 | 10 | ESI+: 447 |
| 148 | 10 | ESI+: 433 |
| 149 | 6 | ESI+: 558 |
| 150 | 6 | ESI+: 544 |
| 151 | 3 | ESI+: 516 |
| 152 | 13 | NMR1: 1.53-2.00(7H, m), 2.88-3.04(8H, m), 3.19-3.54(2H, m), 3.94(3H, s), 4.20-4.31(2H, m), 4.57-4.65(2H, m), 7.23(1H, d, J = 3.6 Hz), 8.09(1H, d, J = 3.6 Hz), 8.72(1H, d, J = 2.0 Hz), 9.24(1H, d, J = 2.0 Hz), 9.44-9.55(1H, br); ESI+: 516 |
| 153 | 10 | ESI+: 417 |
| 154 | 10 | ESI+: 514 |
| 155 | 135 | ESI+: 489 |
| 156 | 11 | ESI+: 556 |
| 157 | 6 | ESI+: 544 |
| 158 | 6 | NMR2: 1.71-2.29(7H, m), 2.31-2.36(3H, m), 2.91-3.02(1H, m), 3.11-3.19(1H, m), 3.51-3.78(4H, m), 3.80-3.94(2H, m), 3.98(3H, s), 4.17-4.30(1H, m), 4.62-4.73(2H, m), 6.89-6.93(1H, m), 7.50-7.54(1H, m), 8.73(1H, s), 9.09-9.14(1H, m); ESI+: 544 |
| 159 | 10 | ESI+: 528 |
| 160 | 11 | ESI+: 612 |

INDUSTRIAL APPLICABILITY

The compound of the formula (I) or a salt thereof has a cathepsin S inhibitory effect, and can be used an agent for preventing and/or treating autoimmune disease, allergic disease, graft rejection of an organ, bone marrow or tissue, systemic lupus erythematosus, lupus nephritis or the like.

The invention claimed is:

1. A compound of formula (I) or a salt thereof:

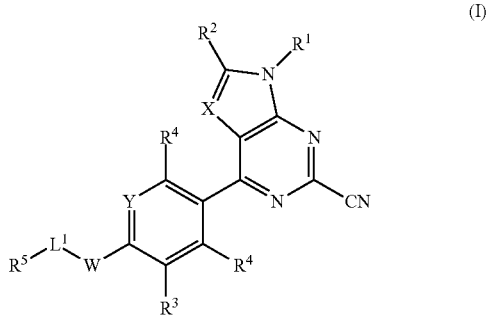

wherein
X is CH or N;
Y is CH, C-halogen, or N;
W is —O— or —S(O)$_n$—;
$L^1$ is a bond, -lower alkylene-, —O-lower alkylene-, —NH-lower alkylene-, or —C(O)-lower alkylene-;
$R^1$ is
(i) lower alkyl which is optionally substituted with one or more substituents selected from the group consisting of a halogen, —OH, —O-lower alkyl, —NH$_2$, —NH-(lower alkyl), —N(lower alkyl)$_2$, —C(O)—NH$_2$, —C(O)—NH-lower alkyl, —C(O)—N(lower alkyl)$_2$, —C(O)—NH-nonaromatic heterocycle which is optionally substituted, —C(O)—N(lower alkyl))-nonaromatic heterocycle which is optionally substituted, a nonaromatic heterocycle which is optionally substituted, and —C(O)-nonaromatic heterocycle which is optionally substituted;
(ii) nonaromatic heterocycle which is optionally substituted; or
(iii) H;
$R^2$ is
(1) lower alkyl which is optionally substituted with a halogen,
(2) a halogen, or
(3) H;
$R^3$ is
(1) lower alkyl which is optionally substituted with a halogen,
(2) a halogen, or
(3) —CN;
each $R^4$ is independently
(1) lower alkyl which is optionally substituted with a halogen,
(2) —OH,
(3) —CN, or
(4) H;
$R^5$ is
(1) lower alkyl which is optionally substituted with a substituent selected from the group consisting of —OH, a halogen, —NH$_2$, —NH-(lower alkyl), and —N(lower alkyl)$_2$,
(2) —O-(lower alkyl which is optionally substituted with a halogen),
(3) $C_{3-8}$ cycloalkyl which is optionally substituted,
(4) an aromatic heterocycle which is optionally substituted, or
(5) a nonaromatic heterocycle which is optionally substituted; and
n is an integer of from 0 to 2.

2. The compound or salt thereof according to claim 1, wherein X is N;
$R^1$ is lower alkyl which is optionally substituted with one or more substituents selected from the group consisting of a halogen, —OH, —O-lower alkyl, and a nonaromatic heterocycle;
wherein nonaromatic heterocycle substituent is optionally substituted with lower alkyl;
$R^5$ is a nonaromatic heterocycle which is optionally substituted with on or more substituents selected from the Group D2;
Group D2 is
(1) a halogen;
(2) cycloalkyl which is optionally substituted with lower alkyl;
(3) an aromatic heterocycle which is optionally substituted with lower alkyl;
(4) a nonaromatic heterocycle which is optionally substituted with lower alkyl;
(5) —OH, —CN, or —NO$_2$;
(6) —C(O)—N(R$^0$)$_2$;
(7) —C(O)—N(lower alkyl)-nonaromatic heterocycle;
(8) —C(O)-lower alkylene-OH;
(9) —C(O)-(lower alkyl which is optionally substituted with one or more substituents selected from Z$^2$ or nonaromatic heterocycle which is optionally substituted with one or more substituents selected from the group consisting of a halogen, —OH, —CN, —O-lower alkyl, cycloalkyl, and a nonaromatic heterocycle);
(10) —C(O)-lower alkylene-(lower alkyl which is optionally substituted with one or more substituents selected from Z$^2$ or nonaromatic heterocycle which is optionally substituted with one or more substituents selected from the group consisting of a halogen, —OH, —CN, —O-lower alkyl, cycloalkyl, and a nonaromatic heterocycle); and
(11) lower alkyl or —O-lower alkyl which are optionally substituted with one or more substituents selected from the group consisting of substituents according to (1) to (8);
each $R^0$ is independently H or lower alkyl; and
Group $Z^2$ is —OH, —O-lower alkyl and a halogen.

3. The compound or salt thereof according to claim 2, wherein W is —O— or —S—;
$L^1$ is -lower alkylene-, —O-lower alkylene-, —NH-lower alkylene-, or —C(O)-lower alkylene-;
$R^1$ is lower alkyl optionally substituted with tetrahydrofuranyl;
$R^2$ is H;
$R^3$ is a halogeno-lower alkyl or —CN;
$R^4$ is H; and
$R^5$ is a nitrogen-containing heterocycloalkyl which is optionally substituted with a substituent selected from the Group D2.

4. The compound or salt thereof according to claim 3, wherein W is —O—.

5. The compound or salt thereof according to claim 4, wherein $R^5$ is azetidinyl, pyrrolidinyl, piperidinyl, or octahydroindolizinyl, each optionally substituted with a substituent of the Group D2.

6. The compound or salt thereof according to claim 1, which is selected from the following group consisting of:
   9-methyl-6-{6-[2-(piperidin-4-yl)ethoxy]-5-(trifluoromethyl)pyridin-3-yl}-9H-purine-2-carbonitrile;
   6-{6-[2-(1-ethylpiperidin-4-yl)ethoxy]-5-(trifluoromethyl)pyridin-3-yl}-9-methyl-9H-purine-2-carbonitrile;
   9-methyl-6-[6-{2-[1-(1-methyl-L-prolyl)piperidin-4-yl]ethoxy}-5-(trifluoromethyl)pyridin-3-yl]-9H-purine-2-carbonitrile;
   6-{4-[2-(1-ethylpiperidin-4-yl)ethoxy]-3-(trifluoromethyl)phenyl}-9-(tetrahydrofuran-3-ylmethyl)-9H-purine-2-carbonitrile; and
   6-{6-[2-(1-cyclobutylpiperidin-4-yl)ethoxy]-5-(trifluoromethyl)pyridin-3-yl}-9-methyl-9H-purine-2-carbonitrile,
   or a salt thereof.

7. A pharmaceutical composition, comprising a compound or salt thereof according to claim 1 and a pharmaceutically acceptable excipient.

8. The compound or a salt thereof according to claim 1, which is 6-{6-[2-(1-ethylpiperidin-4-yl)ethoxy]-5-(trifluoromethyl)pyridin-3-yl}-9-methyl-9H-purine-2-carbonitrile, or a salt thereof.

9. The compound or a salt thereof according to claim 1, which is 4-{6-[2-(1-ethylpiperidin-4-yl)ethoxy]-5-(trifluoromethyl)pyridin-3-yl}-7-methyl-7H-pyrrolo[2,3-d]pyrimidine-2-carbonitrile, or a salt thereof.

\* \* \* \* \*